United States Patent
Perry et al.

(12) 
(10) Patent No.: US 11,116,722 B2
(45) Date of Patent: Sep. 14, 2021

(54) ANTIFUNGAL DRY POWDERS

(71) Applicant: PULMATRIX OPERATING COMPANY, INC., Lexington, MA (US)

(72) Inventors: Jason M. Perry, Cambridge, MA (US); Jean C. Sung, Cambridge, MA (US); David L. Hava, Natick, MA (US); Robert Clifford Saunders, Arlington, MA (US); Hillary S. Bergson, Wilmington, MA (US); Andrew Emmet O'Connor, Somerville, MA (US)

(73) Assignee: Pulmatrix Operating Company, Inc., Lexington, MA (US)

( * ) Notice: Subject to any disclaimer, the term of this patent is extended or adjusted under 35 U.S.C. 154(b) by 0 days.

(21) Appl. No.: 16/341,152

(22) PCT Filed: Oct. 13, 2017

(86) PCT No.: PCT/US2017/056497
§ 371 (c)(1),
(2) Date: Apr. 11, 2019

(87) PCT Pub. No.: WO2018/071757
PCT Pub. Date: Apr. 19, 2018

(65) Prior Publication Data
US 2020/0129428 A1    Apr. 30, 2020

Related U.S. Application Data

(60) Provisional application No. 62/408,376, filed on Oct. 14, 2016.

(51) Int. Cl.
*A61P 31/10* (2006.01)
*A61K 9/14* (2006.01)
(Continued)

(52) U.S. Cl.
CPC ............ *A61K 9/0075* (2013.01); *A61K 9/145* (2013.01); *A61K 31/496* (2013.01); *A61K 47/02* (2013.01);
(Continued)

(58) Field of Classification Search
None
See application file for complete search history.

(56) References Cited

U.S. PATENT DOCUMENTS 4,097,620 A    6/1978  Lu
7,284,552 B2  10/2007  Citterio
(Continued)

FOREIGN PATENT DOCUMENTS

CN    104398497 A  *  3/2015
WO    02/054868 A2    7/2002
(Continued)

OTHER PUBLICATIONS

English Translation of CN 104398497 A. Obtained from Google Translate at https://patents.google.com/patent/CN104398497A/en?oq=itraconazole+dry+powder+inhaler on Feb. 27, 2020. Originally published in Chinese on Mar. 11, 2015. 10 printed pages (Year: 2015).*

(Continued)

*Primary Examiner* — Isaac Shomer
(74) *Attorney, Agent, or Firm* — Hogan Lovells US LLP

(57) ABSTRACT

The invention relates to dry powder formulations comprising respirable dry particles that contain 1) an antifungal agent in crystalline particulate form, 2) a stabilizer, and 3) one or more excipients.

25 Claims, 24 Drawing Sheets

(51) Int. Cl.

| | | |
|---|---|---|
| A61K 31/496 | (2006.01) | |
| A61K 47/18 | (2017.01) | |
| A61K 47/02 | (2006.01) | |
| A61K 47/14 | (2017.01) | |
| A61K 47/26 | (2006.01) | |
| A61K 9/00 | (2006.01) | |

(52) U.S. Cl.
CPC .............. *A61K 47/14* (2013.01); *A61K 47/183* (2013.01); *A61K 47/26* (2013.01); *A61P 31/10* (2018.01)

(56) References Cited

U.S. PATENT DOCUMENTS

| | | | |
|---|---|---|---|
| 7,862,834 | B2 | 1/2011 | Vehring et al. |
| 8,404,217 | B2 | 3/2013 | Tarara et al. |
| 8,513,204 | B2 | 8/2013 | Malcolmson et al. |
| 8,668,934 | B2 | 3/2014 | Vehring et al. |
| 9,061,027 | B2 | 6/2015 | Hitt et al. |
| 9,138,407 | B2 | 9/2015 | Caponetti et al. |
| 9,907,812 | B2 | 3/2018 | Bapat et al. |
| 2002/0062028 | A1* | 5/2002 | Chen ................... C07F 9/6518 548/117 |
| 2002/0177562 | A1* | 11/2002 | Weickert ............. A61K 9/0075 514/27 |
| 2004/0176391 | A1 | 9/2004 | Weers et al. |
| 2005/0048127 | A1 | 3/2005 | Brown et al. |
| 2007/0281011 | A1* | 12/2007 | Jenkins ................... A61K 9/14 424/464 |
| 2007/0287675 | A1 | 12/2007 | Hitt et al. |
| 2010/0172993 | A1 | 7/2010 | Singh et al. |
| 2010/0221343 | A1 | 9/2010 | Johnston et al. |
| 2011/0142914 | A1 | 6/2011 | Persaud et al. |
| 2011/0190245 | A1 | 8/2011 | Rundfeldt et al. |
| 2012/0058151 | A1 | 3/2012 | Gonzalez Ferreiro et al. |
| 2012/0128728 | A1 | 5/2012 | Malcolmson et al. |
| 2015/0017244 | A1* | 1/2015 | Deboeck .............. A61K 31/496 424/489 |
| 2015/0366890 | A1 | 12/2015 | Collins et al. |
| 2016/0199598 | A1* | 7/2016 | Curtis ................ A61M 15/0008 128/203.15 |
| 2018/0369513 | A1 | 12/2018 | Hannon et al. |

FOREIGN PATENT DOCUMENTS

| | | | | |
|---|---|---|---|---|
| WO | 2004060903 | A3 | 7/2004 | |
| WO | 2014106727 | A1 | 7/2004 | |
| WO | 2012030664 | A1 | 3/2012 | |
| WO | 2013132457 | A2 | 12/2013 | |
| WO | WO-2014165303 | A1 * | 10/2014 | ............. A61K 31/57 |

OTHER PUBLICATIONS

C Duret, N Wauthoz, T Sebti, F Vanderbist, K Amighi. "New inhalation-optimized itraconazole nanoparticle-based dry powders for the treatment of invasive pulmonary aspergillosis." International Journal of Nanomedicine, vol. 7, 2012, pp. 5475-5489, published Oct. 17, 2012. (Year: 2012).*

IM El-Sherbiny, NM El-Baz, MH Yacoub. "Inhaled nano- and microparticles for drug delivery." Global Cardiology Science & Practice, vol. 2, 2015, pp. 1-14. (Year: 2015).*

C Duret, N Wauthoz, T Sebti, F Vanderbist, K Amighi. "New inhalation-optimized itraconazole nanoparticle-based dry powders for the treatment of invasive pulmonary aspergillosis." International Journal of Nanomedicine, 2012:7, pp. 5475-5489, published Oct. 17, 2012. (Year: 2012).*

Y Wang, K Kho, WS Cheow, K Hadinoto. "A comparison between spray drying and spray freeze drying for dry powder inhaler formulation of drug-loaded lipid-polymer hybrid nanoparticles." International Journal of Pharmaceutics, vol. 424, 2012, pp. 98-106. (Year: 2012).*

CP Lawlor, MK Tauber, JT Brogan, L Zhu, DF Currie, BG Trautman, JC Sung. "Levofloxacin Dry Powders Engineered for Efficient Pulmonary Delivery and Stability." Respiratory Drug Delivery, 2014, pp. 549-552. (Year: 2014).*

María P. Fernández-Ronco, Matteo Salvalaglio, Johannes Kluge, and Marco Mazzotti. "Study of the Preparation of Amorphous Itraconazole Formulations." Crystal Growth & Design, vol. 15, 2015, pp. 2686-2694. (Year: 2015).*

Christophe Duret, Nathalie Wauthoz, Thami Sebti, Francis Vanderbist, Karim Amighi. "New Respirable and Fast Dissolving Itraconazole Dry Powder Composition for the Treatment of Invasive Pulmonary Aspergillosis." Pharmaceutical Research, vol. 29, 2012, pp. 2845-2859. (Year: 2012).*

Christophe Duret, et al. "Pharmacokinetic evaluation in mice of amorphous itraconazole-based dry powder formulations for inhalation with high bioavailability and extended lung retention." European Journal of Pharmaceutics and Biopharmaceutics 86 (2014) 46-54. (Year: 2014).*

Capsule Connection. https://capsuleconnection.com/capsule-sizing-info/accessed Jan. 19, 2021, pp. 1-2. (Year: 2021).*

Pharma State Blog. "Dissolution Apparatus and its Type." https://pharmastate.blog/dissolution-apparatus-and-its-type/ accessed Jan. 29, 2021, pp. 1-21. (Year: 2021).*

Sanjay G. Revankar. "Antifungal Drugs." Merck Manual Professional Version, https://www.merckmanuals.com/professional/infectious-diseases/fungi/antifungal-drugs# accessed Jan. 31, 2021, originally published Jul. 2019, pp. 1-8. (Year: 2019).*

International Search Report issued for the European Patent Office for International Application No. PCT/US2017/056497, dated Mar. 23, 2018, 3 pages.

Yang, et al. "Comparison of Bioavailability of Amorphous Versus Crystalline Itraconazole Nanoparticles Via Pulmonary Administration in Rats", European Journal of Pharmaceutics and Biopharmaceutics 75 (2010) 33-41.

Conte, et al. "Intrapulmonary Pharmacokinetics and Pharmacodynamics of Itraconazole and 14-Hydroxyitraconazole at Steady State", Antimicrobial Agents and Chemotherapy, Oct. 2004, p. 3823-3827 vol. 48, No. 10, 3823-3827 (2004).

Conway, et al. "Pharmacokinetics and Safety of Itraconazole in Patients with Cystic Fibrosis", J Antimicrobial Chemotherapy (2004) 53, 841-847.

Duret, et al. "Pharmacokinetic Evaluation in Mice of Amorphous Itraconazole-Based Dry Powder Formulations for Inhalation with High Bioavailability and Extended Lung Retention", European Journal of Pharmaceutics and Biopharmaceutics, 86 (2014) 46-54.

Kumar, et al., "In Vitro and In Vivo Performance of Different Sized Spray-Dried Crystalline Itraconazole", Journal of Pharmaceutical Sciences 104 (2015) 3018-3028.

Pardeike, et al., "Development of an Itraconazole-loaded nanostructured lipid carrier (NLC) formulation for pulmonary application", International Journal of Pharmaceutics 419 (2011) 329-338.

Rundfeldt, et al. "Inhalable Highly Concentrated Itraconazole Nanosuspension for the Treatment of Bronchopulmonary Aspergillosis", European Journal of Pharmaceutics and Biopharmaceutics 83 (2013) 44-53.

Sermet-Gaudelus, et al. "Sputum Itraconazole Concentrations in Cystic Fibrosis Patients", Antimicrobial Agents Chemotherapy, (2001), 45(6): 10.1128/AAC.45.6.1937-1938.2001.

Stevens, et al. "A Randomized Trial of Itraconazole in Allergic Bronchopulmonary Aspergillosis", The New England Journal of Medicine, 342: 756-762, Mar. 16, 2000.

Tolman, et al. "Inhaled Voriconazole for Prevention of Invasive Pulmonary Aspergillosis", Antimicrobial Agents and Chemotherapy, Jun. 2009, p. 2613-2615.

Tolman, et al. "Characterization and Pharmacokinetic Analysis of Aerosolized Aqueous Voriconazole Solution", European Journal of Pharmaceutics and Biopharmaceutics 72 (2009) 199-205.

Wark, et al. "Anti-inflammatory Effect of Itraconazole in Stable Allergic Bronchopulmonary Aspergillosis: A Randomized Controlled Trial", J Allergy Clin Immunol, vol. 111, No. 5 (2003).

Duret, et al. "New Respirable and Fast Dissolving Itraconazole Dry Powder Composition for the Treatment of Invasive Pulmonary Aspergillosis", Pharm Res (2012) 29:2845-2859.

(56) References Cited

OTHER PUBLICATIONS

RS01 inhaler online catalog, Berry Bramblage, https://catalogue.rpc-bramlage.com/en/portals/berrybramlage/assets/12709911/rs01-mod-7/packtags/203000000/health/ (accessed online Apr. 12, 2021).

* cited by examiner

ANTIFUNGAL DRY POWDERS

RELATED APPLICATIONS

This application claims the benefit of U.S. Patent Application No. 62/408,376, filed on Oct. 14, 2016, the entire contents of which are incorporated herein by reference.

BACKGROUND

Pulmonary fungal infections by *Aspergillus* spp. and other fungi are a growing concern in patients with decreased respiratory function, such as cystic fibrosis (CF) patients. For example, patients can have chronic pulmonary fungal infection or Allergic Bronchopulmonary Aspergillosis (ABPA), a severe inflammatory condition that is typically treated with a long course of oral steroids. A number of antifungal agents are known including triazoles (e.g., itraconazole), polyenes (e.g., amphotericin B), and echinocandins. Antifungal agents typically have low aqueous solubility and poor oral bioavailability and obtaining pharmaceutical formulations that can be administered to provide safe and therapeutic levels of antifungal agents has been challenging. Antifungal agents are typically administered as oral or intravenous (IV) formulations as treatments for fungal infections, including pulmonary infection and ABPA. However, such formulations are limited by poor oral bioavailability, adverse side effects and toxicity, and extensive drug-drug interactions. Alternative approaches, such as delivery to the airway by inhalation, which theoretically could reduce systemic side effects also present challenges. Notably, it is well-known that agents with poor aqueous solubility produce local lung toxicity (e.g., local inflammation, granuloma) when inhaled. The conventional approach to address local toxicity of poorly soluble agents is to formulate the agent to increase its rate of dissolution, for example using amorphous formulations.

The chemical structure of itraconazole is described in U.S. Pat. No. 4,916,134. Itraconazole is a triazole antifungal agent providing therapeutic benefits (e.g., in the treatment of fungal infections), and is the active ingredient in SPORANOX® (itraconazole; Janssen Pharmaceuticals) which may be delivered orally or intravenously. Itraconazole can be synthesized using a variety of methods that are well known in the art.

A need exists for new formulations of antifungal agents that can safely be administered to treat fungal infections.

SUMMARY OF THE INVENTION

The invention relates to dry powder formulations comprising homogenous respirable dry particles that contain 1) an antifungal agent in crystalline particulate form, 2) a stabilizer, and optionally 3) one or more excipients. In one particular aspect, the antifungal agent in crystalline particulate form is not a polyene antifungal agent. In another particular aspect, the invention relates to 1) a triazole antifungal agent in crystalline particulate form, 2) a stabilizer, and optionally 3) one or more excipients. In a more particular aspect, the triazole antifungal agent is itraconazole.

In all aspects of the inventions, the antifungal agent in crystalline particulate form is in the form of a sub-particle of about 50 nm to about 5,000 nm (Dv50). In one embodiment the sub-particle is about 50 nm to about 800 nm (Dv50). In one embodiment the sub-particle is about 50 nm to about 300 nm (Dv50). In one embodiment, the sub-particle is about 50 to about 200 nm (Dv50). In one embodiment, the sub-particle is about 100 nm to about 300 nm (Dv50). The antifungal agent is present in an amount of about 1% to about 95% by weight. The antifungal agent is present in an amount of about 40% to about 90% by weight. The antifungal agent is present in an amount of about 55% to about 85% by weight. The antifungal agent is present in an amount of about 55% to about 75% by weight. The antifungal agent is present in an amount of about 65% to about 85% by weight. The antifungal agent is present in an amount of about 40% to about 60% by weight. Preferably, the antifungal agent is at least about 50% crystalline. The ratio of antifungal agent:stabilizer (wt:wt) is from about 1:1 to 50:1. The ratio of antifungal agent: stabilizer may be greater than or equal to 10:1, about 10:1, or about 20:1. The ratio of antifungal agent:stabilizer may be about 5:1 to about 20:1, about 7:1 to about 15:1, or about 9:1 to about 11:1. The stabilizer is present in an amount of about 0.05% to about 45% by weight. The stabilizer can be present in an amount of about 4% to about 10% by weight. The one or more excipients are present in an amount of about 10% to about 99% by weight. The one or more excipient may be present in an amount of about 5% to about 50% by weight. The excipient can be a sodium salt.

In some embodiments, the one or more excipients can comprise a monovalent metal cation salt, a divalent metal cation salt, an amino acid, a sugar alcohol, or combinations thereof. The one or more excipients can comprise a sodium salt and an amino acid, such as sodium chloride or sodium sulfate, and leucine. The one or more excipients can comprise a magnesium salt and an amino acid, such as magnesium lactate and leucine.

In some embodiments, the stabilizer can be polysorbate 80 or oleic acid or a salt thereof. The stabilizer can be polysorbate 80 and be present in an amount of 10 wt % or less. The stabilizer can be polysorbate 80 and be present in an amount of 7 wt % or less. The stabilizer can be polysorbate 80 and be present in an amount of 3 wt % or less. The stabilizer can be oleic acid and be present in an amount of 10 wt % or less. The stabilizer can be oleic acid and be present in an amount of 7 wt % or less. The stabilizer can be oleic acid and be present in an amount of 3 wt % or less.

In some embodiments, the respirable dry particles can have a volume median geometric diameter (VMGD) of about 10 microns or less, about 5 microns or less. In some embodiments, the respirable dry particles can have a tap density of 0.2 g/cc or greater. The respirable dry particles can have a tap density of between 0.2 g/cc and 1.0 g/cc.

In some embodiments, the dry powder has a MMAD of between about 1 micron and about 5 microns. The dry particles can have a ¼ bar dispersiblilty ratio (¼ bar) of less than about 1.5 as measured by laser diffraction. The dry particles can have a 0.5/4 bar dispersibility ratio (0.5/4) bar of about 1.5 or less as measured by laser diffraction. The dry powder can have a FPF of the total dose less than 5 microns of about 25% or more.

The invention also relates to methods of treating fungal infections by administering the dry powders described herein to a subject in need thereof by inhalation. The invention also relates to methods of treating cystic fibrosis by administering the dry powders described herein to a subject in need thereof by inhalation. The invention also relates to methods of treating asthma by administering the dry powders described herein to a subject in need thereof by inhalation. The invention also relates to methods of treating aspergillosis by administering the dry powders described herein to a subject in need thereof by inhalation. The invention also relates to methods of treating allergic bronchopulmonary aspergillosis (ABPA) by administering the dry powders described herein to a subject in need thereof by inhalation. The invention also relates to methods of treating or reducing the severity of an acute exacerbation of a respiratory disease by administering the dry powders described herein to a subject in need thereof by inhalation. The invention also relates to dry powders described herein for use in treating fungal infections. The invention also relates to dry powders described herein for use in treating aspergillosis. The invention also relates to dry powders described herein for use in treating allergic bronchopulmonary aspergillosis (ABPA). The invention also relates to dry powders described herein for use in treating an acute exacerbation of a respiratory disease in an individual.

The dry powder can be delivered to the partient with a capsule-based passive dry powder inhaler.

The invention also relates to a dry powder produced by a process comprising spray drying a surfactant-stabilized suspension with optional excipients, wherein dry particles that are compositionally homogenous are produced.

DETAILED DESCRIPTION OF THE INVENTION

Figure 1:
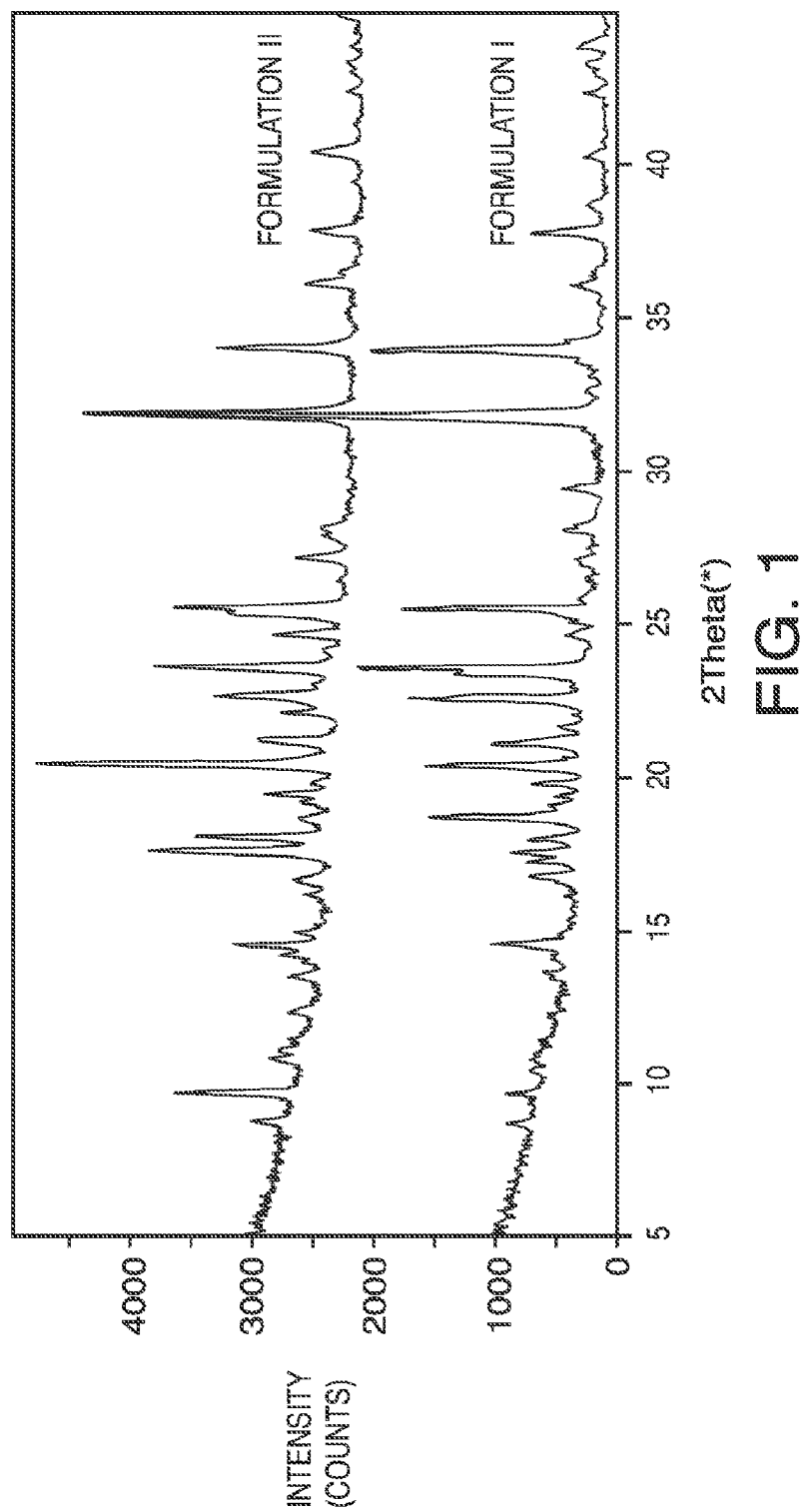
FIG. 1: Particle X-Ray Diffraction plot for Formulations I and II.

This disclosure relates to respirable dry powders that contain an antifungal agent in crystalline particulate form. The inventors have discovered that dry powder formulations that contain antifungal agents, such as itraconazole, in amorphous form have shorter lung residence times, reduced lung to plasma exposure ratios and undesirable toxic effects on lung tissue when inhaled at therapeutic doses. Without wishing to be bound by any particular theory, it is believed that the crystalline forms (e.g., nanocrystalline forms) of the material have a slower dissolution rate in the lung, providing more continuous exposure over a 24 hour period after administration and minimizing systemic exposure. In addition, the observed local toxicity in lung tissue without amorphous dosing is not related to the total exposure of the lung tissue to the drug, in terms of total dose or duration of exposure. Itraconazole has no known activity against human or animal lung cells and so increasing local concentration has no local pharmacological activity to explain the local toxicity. Instead, the toxicity of the amorphous form appears related to the increased solubility secondary to the amorphous nature of the itraconazole, resulting in supersaturation of the drug in the interstitial space and the resultant recrystallization in the tissue leading to local, granulomatous inflammation. Surprisingly, the inventors discovered that dry powders that contain antifungal agents in crystalline particulate form are less toxic to lung tissue. This was surprising because the crystalline particulate antifungal agents have a lower dissolution rate in comparison to the amorphous forms, and remain in the lung longer than a corresponding dose of the antifungal agent in amorphous form.

The crystallinity of the antifungal agent, as well as the size of the antifungal crystalline particles, appears to be important for effective therapy and for reduced toxicity in the lung. Without wishing to be bound by any particular theory, it is believed that crystalline particles of the antifungal agent will dissolve in the airway lining fluid more rapidly than larger crystalline particles—in part due to the larger total amount of surface area. It is also believed that crystalline antifungal agent will dissolve more slowly in the airway lining fluid than the amorphous antifungal agent. Accordingly, the dry powders described herein can be formulated using antifungal agents in crystalline particulate form that provide for a desired degree of crystallinity and particle size, and can be tailored to achieve desired pharmacokinetic properties while avoiding unacceptable toxicity in the lungs.

The respirable dry powders of this disclosure include homogenous respirable dry particles that contain 1) an antifungal agent in crystalline particulate form, 2) a stabilizer, and optionally 3) one or more excipients. Accordingly, the dry powders are characterized by respirable dry particles that contain a stabilizer, optionally one or more excipients, and a sub-particle (particle that is smaller than the respirable dry particle) that contains crystalline antifungal agent. Such respirable dry particles can be prepared using any suitable method, such as by preparing a feedstock in which an antifungal agent in crystalline particulate form is suspended in an aqueous solution of excipients, and spray drying the feedstock.

The dry powders may be administered to a patient by inhalation, such as oral inhalation. To achieve oral inhalation, a dry powder inhaler may be used, such as a passive dry powder inhaler. The dry powder formulations can be used to treat or prevent fungal infections in a patient, such as *aspergillus* infections. Patients that would benefit from the dry powders are, for example, those who suffer from cystic fibrosis, asthma, and/or who are at high risk of developing fungal infections due to being severely immunocompromised. An inhaled formulation of antifungal agent (e.g., itraconazole) minimizes many of the downsides of oral or intravenous (IV) formulations in treating these patients.

Definitions

As used herein, the term "about" refers to a relative range of plus or minus 5% of a stated value, e.g., "about 20 mg" would be "20 mg plus or minus 1 mg".

As used herein, the terms "administration" or "administering" of respirable dry particles refers to introducing respirable dry particles to the respiratory tract of a subject.

As used herein, the term "amorphous" indicates lack of significant crystallinity when analyzed via powder X-ray diffraction (XRD).

The term "capsule emitted powder mass" or "CEPM" as used herein refers to the amount of dry powder formulation emitted from a capsule or dose unit container during an inhalation maneuver. CEPM is measured gravimetrically, typically by weighing a capsule before and after the inhalation maneuver to determine the mass of powder formulation removed. CEPM can be expressed either as the mass of powder removed, in milligrams, or as a percentage of the initial filled powder mass in the capsule prior to the inhalation maneuver.

The term "crystalline particulate form" as used herein refers to an antifungal agent (including pharmaceutically acceptable forms thereof including salts, hydrates, enantiomers as the like), that is in the form of a particle (i.e., sub-particle that is smaller than the respirable dry particles that comprise the dry powders disclosed herein) and in which the antifungal agent is at least about 50% crystalline. The percent crystallinity of an antifungal agent refers to the percentage of the compound that is in crystalline form relative to the total amount of compound present in the sub-particle. If desired, the antifungal agent can be at least about 60%, at least about 70%, at least about 80%, at least about 90%, at least about 95%, or about 100% crystalline. An antifungal agent in crystalline particulate form is in the form of a particle that is about 50 nanometers (nm) to about 5,000 nm volume median diameter (Dv50), preferably 80 nm to 1750 nm Dv50, or preferably 50 nm to 800 nm Dv50.

The term "dispersible" is a term of art that describes the characteristic of a dry powder or respirable dry particles to be dispelled into a respirable aerosol. Dispersibility of a dry powder or respirable dry particles is expressed herein, in one aspect, as the quotient of the volumetric median geometric diameter (VMGD) measured at a dispersion (i.e., regulator) pressure of 1 bar divided by the VMGD measured at a dispersion (i.e., regulator) pressure of 4 bar, or VMGD at 0.5 bar divided by the VMGD at 4 bar as measured by laser diffraction, such as with a HELOS/RODOS. These quotients are referred to herein as "1 bar/4 bar dispersibility ratio" and "0.5 bar/4 bar dispersibility ratio", respectively, and dispersibility correlates with a low quotient. For example, 1 bar/4 bar dispersibility ratio refers to the VMGD of a dry powder or respirable dry particles emitted from the orifice of a RODOS dry powder disperser (or equivalent technique) at about 1 bar, as measured by a HELOS or other laser diffraction system, divided by the VMGD of the same dry powder or respirable dry particles measured at 4 bar by HELOS/RODOS. Thus, a highly dispersible dry powder or respirable dry particles will have a 1 bar/4 bar dispersibility ratio or 0.5 bar/4 bar dispersibility ratio that is close to 1.0. Highly dispersible powders have a low tendency to agglomerate, aggregate or clump together and/or, if agglomerated, aggregated or clumped together, are easily dispersed or de-agglomerated as they emit from an inhaler and are breathed in by a subject. In another aspect, dispersibility is assessed by measuring the particle size emitted from an inhaler as a function of flowrate. As the flow rate through the inhaler decreases, the amount of energy in the airflow available to be transferred to the powder to disperse it decreases. A highly dispersible powder will have a size distribution such as is characterized aerodynamically by its mass median aerodynamic diameter (MMAD) or geometrically by its VMGD that does not substantially increase over a range of flow rates typical of inhalation by humans, such as about 15 to about 60 liters per minute (LPM), about 20 to about 60 LPM, or about 30 LPM to about 60 LPM. A highly dispersible powder will also have an emitted powder mass or dose, or a capsule emitted powder mass or dose, of about 80% or greater even at the lower inhalation flow rates. VMGD may also be called the volume median diameter (VMD), x50, or Dv50.

The term "dry particles" as used herein refers to respirable particles that may contain up to about 15% total of water and/or another solvent. Preferably, the dry particles contain water and/or another solvent up to about 10% total, up to about 5% total, up to about 1% total, or between 0.01% and 1% total, by weight of the dry particles, or can be substantially free of water and/or other solvent.

The term "dry powder" as used herein refers to compositions that comprise respirable dry particles. A dry powder may contain up to about 15% total of water and/or another solvent. Preferably the dry powder contain water and/or another solvent up to about 10% total, up to about 5% total, up to about 1% total, or between 0.01% and 1% total, by weight of the dry powder, or can be substantially free of water and/or other solvent. In one aspect, the dry powder is a respirable dry powder.

The term "effective amount," as used herein, refers to the amount of agent needed to achieve the desired effect; such as treating a fungal infection, e.g., an *aspergillus* infection, in the respiratory tract of a patient, e.g., a Cystic Fibrosis (CF) patient, an asthma patient and an immunocompromised patient; treating allergic bronchopulmonary aspergillosis (ABPA); and treating or reducing the incidence or severity of an acute exacerbation of a respiratory disease. The actual effective amount for a particular use can vary according to the particular dry powder or respirable dry particle, the mode of administration, and the age, weight, general health of the subject, and severity of the symptoms or condition being treated. Suitable amounts of dry powders and dry particles to be administered, and dosage schedules for a particular patient can be determined by a clinician of ordinary skill based on these and other considerations.

As used herein, the term "emitted dose" or "ED" refers to an indication of the delivery of a drug formulation from a suitable inhaler device after a firing or dispersion event. More specifically, for dry powder formulations, the ED is a measure of the percentage of powder that is drawn out of a unit dose package and that exits the mouthpiece of an inhaler device. The ED is defined as the ratio of the dose delivered by an inhaler device to the nominal dose (i.e., the mass of powder per unit dose placed into a suitable inhaler device prior to firing). The ED is an experimentally-measured parameter, and can be determined using the method of USP Section 601 Aerosols, Metered-Dose Inhalers and Dry Powder Inhalers, Delivered-Dose Uniformity, Sampling the Delivered Dose from Dry Powder Inhalers, United States Pharmacopeia convention, Rockville, Md., 13$^{th}$ Revision, 222-225, 2007. This method utilizes an in vitro device set up to mimic patient dosing.

The term "nominal dose" as used herein refers to an individual dose greater than or equal to 1 mg of antifungal agent. The nominal dose is the total dose inhaled/administered with one capsule, blister, or ampule.

The terms "FPF (<X)," "FPF (<X microns)," and "fine particle fraction of less than X microns" as used herein, wherein X equals, for example, 3.4 microns, 4.4 microns, 5.0 microns or 5.6 microns, refer to the fraction of a sample of dry particles that have an aerodynamic diameter of less than X microns. For example, FPF (<X) can be determined by dividing the mass of respirable dry particles deposited on stage two and on the final collection filter of a two-stage collapsed Andersen Cascade Impactor (ACI) by the mass of respirable dry particles weighed into a capsule for delivery to the instrument. This parameter may also be identified as "FPF_TD(<X)," where TD means total dose. A similar measurement can be conducted using an eight-stage ACI. An eight-stage ACI cutoffs are different at the standard 60 L/min flowrate, but the FPF_TD(<X) can be extrapolated from the eight-stage complete data set. The eight-stage ACI result can also be calculated by the USP method of using the dose collected in the ACI instead of what was in the capsule to determine FPF. Similarly, a seven-stage next generation impactor (NGD can be used.

The terms "FPD (<X)", 'FPD<X microns", FPD(<X microns)" and "fine particle dose of less than X microns" as used herein, wherein X equals, for example, 3.4 microns, 4.4 microns, 5.0 microns or 5.6 microns, refer to the mass of a therapeutic agent delivered by respirable dry particles that have an aerodynamic diameter of less than X micrometers. FPD<X microns can be determined by using an eight-stage ACI at the standard 60 L/min flowrate and summing the mass deposited on the final collection filter, and either directly calculating or extrapolating the FPD value.

The term "respirable" as used herein refers to dry particles or dry powders that are suitable for delivery to the respiratory tract (e.g., pulmonary delivery) in a subject by inhalation. Respirable dry powders or dry particles have a mass median aerodynamic diameter (MMAD) of less than about 10 microns, preferably about 5 microns or less.

As used herein, the term "respiratory tract" includes the upper respiratory tract (e.g., nasal passages, nasal cavity, throat, and pharynx), respiratory airways (e.g., larynx, trachea, bronchi, and bronchioles) and lungs (e.g., respiratory bronchioles, alveolar ducts, alveolar sacs, and alveoli).

The term "small" as used herein to describe respirable dry particles refers to particles that have a volume median geometric diameter (VMGD) of about 10 microns or less, preferably about 5 microns or less, or less than 5 microns.

The term "stabilizer" as used herein refers to a compound that improves the physical stability of antifungal agents in crystalline particulate form when suspended in a liquid in which the antifungal agent is poorly soluble (e.g., reduces the aggregation, agglomeration, Ostwald ripening and/or flocculation of the particulates). Suitable stabilizers are surfactants and amphiphilic materials and include Polysorbates (PS; polyoxyethylated sorbitan fatty acid esters), such as PS20, PS40, PS60 and PS80; fatty acids such as lauric acid, palmitic acid, myristic acid, oleic acid and stearic acid; sorbitan fatty acid esters, such as Span20, Span40, Span60, Span80, and Span 85; phospholipds such as dipalmitoylphosphosphatidylcholine (DPPC), 1,2-Dipalmitoyl-sn-glycero-3-phospho-L-serine (DPPS), 1,2-Dipalmitoyl-sn-glycero-3-phosphocholine (DSPC), 1-palmitoyl-2-oleoylphosphatidylcholine (POPC), and 1,2-Dioleoyl-sn-glycero-3-phosphocholine (DOPC); Phosphatidylglycerols (PGs) such as diphosphatidyl glycerol (DPPG), DSPG, DPPG, POPG, etc.; 1,2-Distearoyl-sn-glycero-3-phosphoethanolamine (DSPE); fatty alcohols; benzyl alcohol, polyoxyethylene-9-lauryl ether; glycocholate; surfactin; poloxomers; polyvinylpyrrolidone (PVP); PEG/PPG block co-polymers (Pluronics/Poloxamers); polyoxyethyene chloresteryl ethers; POE alky ethers; tyloxapol; lecithin; and the like. Preferred stabilizers are polysorbates and fatty acids. A particularly preferred stabilizer is PS80. Another preferred stabilizer is oleic acid.

The term "homogenous dry particle" as used herein refers to particles containing crystalline drug (e.g., nano-crystalline drug) which is pre-processed as a surfactant stabilized suspension. The homogenous dry particle is then formed by spray drying the surfactant-stabilized suspension with (optional) excipients, resulting in dry particles that are compositionally homogenous, or more specifically, identical in their composition of surfactant-coated crystalline drug particles and optionally one or more excipients.

Dry Powders and Dry Particles

The invention relates to dry powder formulations comprising respirable dry particles that contain 1) an antifungal agent in crystalline particulate form, 2) a stabilizer, and 3) one or more excipients. Any desired antifungal agents can be included in the formulations described herein. Many antifungal agents are well-known, for example, polyene antifungals, such as amphotericin B; triazole antifungals, such as itraconazole, ketoconazole, fluconazole, voriconazole, and posaconazole; echinocandin antifungals, such as caspofungin, micafungin, and anidulafungin. Other triazole antifungals include clotrimazole, Isavuconazole, and miconazole. Included are a new chemical class of triterpenoid glucan synthase inhibitors, for example, SCY-078. Also included are orotomide antifungals, such as F901318, which inhibits dihydroorotate dehydrogenase.

The crystallinity of the antifungal agent, as well as the size of the antifungal sub-particles, appears to be important for effective therapy and for reduced toxicity in the lung. Without wishing to be bound by any particular theory, it is believed that smaller sub-particles of antifungal agent in crystalline form will dissolve in the airway lining fluid more rapidly than larger particles—in part due to the larger amount of surface area. It is also believed that crystalline antifungal agent will dissolve more slowly in the airway lining fluid than amorphous antifungal agent. Accordingly, the dry powders described herein can be formulated using antifungal agents in crystalline particulate form that provide for a desired degree of crystallinity and sub-particle size, and can be tailored to achieve desired pharmacokinetic properties while avoiding unacceptable toxicity in the lungs.

The respirable dry particles contain about 1% to about 95% antifungal agent by weight (wt %). It is preferred that the respirable dry particle contains an amount of antifungal agent so that a therapeutically effective dose can be administered and maintained without the need to inhale large volumes of dry powder more than three time a day. For example, it is preferred that the respirable dry particles contain about 10% to 75%, about 15% to 75%, about 25% to 75%, about 30% to 70%, about 40% to 60%, about 20%, about 50%, or about 70% antifungal agent by weight (wt %). The respirable dry particles may contain about 75%, about 80%, about 85%, about 90%, or about 95% antifungal agent by weight (wt %). In particular embodiments, the range of antifungal agent in the respirable dry particles is about 40% to about 90%, about 55% to about 85%, about 55% to about 75%, or about 65% to about 85%, by weight (wt %). The amount of antifungal agent present in the respirable dry particles by weight is also referred to as the "drug load."

The antifungal agent is present in the respirable dry particles in crystalline particulate form (e.g., nano-crystalline). More specifically, in the form of a sub-particle that is about 50 nm to about 5,000 nm (Dv50), preferably, with the antifungal agent being at least 50% crystalline. For example, for any desired drug load, the sub-particle size can be about 100 nm, about 300 nm, about 1500 nm, about 80 nm to about 300 nm, about 80 nm to about 250 nm, about 80 nm to about 200 nm, about 100 nm to about 150 nm, about 1200 nm to about 1500 nm, about 1500 nm to about 1750 nm, about 1200 nm to about 1400 nm, or about 1200 nm to about 1350 nm (Dv50). In particular embodiments, the sub-particle is between about 50 nm to about 2500 nm, between about 50 nm and 1000 nm, between about 50 nm and 800 nm, between about 50 nm and 600 nm, between about 50 nm and 500 nm, between about 50 nm and 400 nm, between about 50 nm and 300 nm, between about 50 nm and 200 nm, or between about 100 nm and 300 nm. In addition, for any desired drug load and sub-particle size, the degree of antifungal agent crystallinity can be at least about 50%, at least about 60%, at least about 70%, at least about 80%, at least about 90%, at least about 95%, or about 100% crystalline. Preferably, the antifungal agent is about 100% crystalline.

The antifungal agent in crystalline particulate form can be prepared in any desired sub-particle size using a suitable method, including a stabilizer if desired, such as by wet milling, jet milling or other suitable method.

The respirable dry particles also include a stabilizer. The stabilizer helps maintain the desired size of the antifungal agent in crystalline particulate form during wet milling, in spray drying feedstock, and aids in wetting and dispersing. It is preferred to use as little stabilizer as is needed to obtain the desired dry powder. The amount of stabilizer is typically related to the amount of antifungal agent present in the dry particle and can range from about 1:1 (antifungal agent: stabilizer (wt:wt)) to about 50:1 (wt:wt), with ≥ (greater than or equal to) 10:1 being preferred. For example, the ratio of antifungal agent:stabilizer (wt:wt) in the dry particles can be ≥ (greater than or equal to) 10:1, about 10:1, about 20:1, or about 10:1 to about 20:1. In particular embodiments, the ratio is about 5:1 to about 20:1, about 7:1 to about 15:1, or about 9:1 to about 11:1. In addition, the amount of stabilizer that is present in the dry particles can be in a range of about 0.05% to about 45% by weight (wt %). In particular embodiments, the range is about 1% to about 15%, about 4% to about 10%, or about 5% to about 8% by weight (wt %). It is generally preferred that the respirable dry particles contain less than about 10% stabilizer by weight (wt %), such as 7 wt %, 5 wt % or 1 wt %. Alternatively, the respirable dry particles contain about 5 wt %, about 6 wt %, about 7 wt %, about 7.5 wt %, about 8 wt %, or about 10% stabilizer. It is particularly preferred that respirable dry particles contain less than about 5 wt % stabilizer. A particularly preferred stabilizer for use in the dry powders described herein is polysorbate 80. Another preferred stabilizer is oleic acid (or salt forms thereof). In contrast to the prior art, which uses surfactant to prevent the onset of crystallization in the produced dry powder, the surfactant in the present invention is added to stabilize a colloidal suspension of the crystalline drug in an anti-solvent.

The respirable dry particles also include any suitable and desired amount of one or more excipients. The dry particles can contain a total excipient content of about 10 wt % to about 99 wt %, with about 25 wt % to about 85 wt %, or about 40 wt % to about 55 wt % being more typical. The dry particles can contain a total excipient content of about 1 wt %, about 2 wt %, about 4 wt %, about 6 wt %, about 8 wt %, or less than about 10 wt %. In particular embodiments, the range is about 5% to about 50%, about 15% to about 50%, about 25% to about 50%, about 5% to about 40%, about 5% to about 30%, about 5% to about 20%, or about 5% to about 15%.

Many excipients are well-known in the art and can be included in the dry powders and dry particles described herein. Pharmaceutically acceptable excipients that are particularly preferred for the dry powders and dry particles described herein include monovalent and divalent metal cation salts, carbohydrates, sugar alcohols and amino acids.

Suitable monovalent metal cation salts, include, for example, sodium salts and potassium salts. Suitable sodium salts that can be present in the respirable dry particles of the invention include, for example, sodium chloride, sodium citrate, sodium sulfate, sodium lactate, sodium acetate, sodium bicarbonate, sodium carbonate, sodium stearate, sodium ascorbate, sodium benzoate, sodium biphosphate, sodium phosphate, sodium bisulfite, sodium borate, sodium gluconate, sodium metasilicate and the like.

Suitable potassium salts include, for example, potassium chloride, potassium bromide, potassium iodide, potassium bicarbonate, potassium nitrite, potassium persulfate, potassium sulfite, potassium bisulfite, potassium phosphate, potassium acetate, potassium citrate, potassium glutamate, dipotassium guanylate, potassium gluconate, potassium malate, potassium ascorbate, potassium sorbate, potassium succinate, potassium sodium tartrate and any combination thereof.

Suitable divalent metal cation salts, include magnesium salts and calcium salts. Suitable magnesium salts include, for example, magnesium lactate, magnesium fluoride, magnesium chloride, magnesium bromide, magnesium iodide, magnesium phosphate, magnesium sulfate, magnesium sulfite, magnesium carbonate, magnesium oxide, magnesium nitrate, magnesium borate, magnesium acetate, magnesium citrate, magnesium gluconate, magnesium maleate, magnesium succinate, magnesium malate, magnesium taurate, magnesium orotate, magnesium glycinate, magnesium naphthenate, magnesium acetylacetonate, magnesium formate, magnesium hydroxide, magnesium stearate, magnesium hexafluorsilicate, magnesium salicylate or any combination thereof.

Suitable calcium salts include, for example, calcium chloride, calcium sulfate, calcium lactate, calcium citrate, calcium carbonate, calcium acetate, calcium phosphate, calcium alginate, calcium stearate, calcium sorbate, calcium gluconate and the like.

A preferred sodium salt is sodium sulfate. A preferred sodium salt is sodium chloride. A preferred sodium salt is sodium citrate. A preferred magnesium salt is magnesium lactate.

Carbohydrate excipients that are useful in this regard include the mono- and polysaccharides. Representative monosaccharides include dextrose (anhydrous and the monohydrate; also referred to as glucose and glucose monohydrate), galactose, D-mannose, sorbose and the like. Representative disaccharides include lactose, maltose, sucrose, trehalose and the like. Representative trisaccharides include raffinose and the like. Other carbohydrate excipients including dextran, maltodextrin and cyclodextrins, such as 2-hydroxypropyl-beta-cyclodextrin can be used as desired. Representative sugar alcohols include mannitol, sorbitol and the like. A preferred sugar alcohol is mannitol.

Suitable amino acid excipients include any of the naturally occurring amino acids that form a powder under standard pharmaceutical processing techniques and include the non-polar (hydrophobic) amino acids and polar (uncharged, positively charged and negatively charged) amino acids, such amino acids are of pharmaceutical grade and are generally regarded as safe (GRAS) by the U.S. Food and Drug Administration. Representative examples of non-polar amino acids include alanine, isoleucine, leucine, methionine, phenylalanine, proline, tryptophan and valine. Representative examples of polar, uncharged amino acids include cystine, glycine, glutamine, serine, threonine, and tyrosine. Representative examples of polar, positively charged amino acids include arginine, histidine and lysine. Representative examples of negatively charged amino acids include aspartic acid and glutamic acid. A preferred amino acid is leucine.

The dry particles described herein contain 1) an antifungal agent in crystalline particulate form, 2) a stabilizer, and optionally 3) one or more excipients. In some aspects, the dry particles contain a first excipient that is a monovalent or divalent metal cation salt, and a second excipient that is an amino acid, carbohydrate or sugar alcohol. For example, the first excipient can be a sodium salt or a magnesium salt, and the second excipient can be an amino acid (such as leucine). In more particular examples, the first excipient can be sodium sulfate, sodium chloride or magnesium lactate, and the second excipient can be leucine. Even more particularly, the first excipient can be sodium sulfate and the second excipient can be leucine. In another example, the first excipient can be a sodium salt or a magnesium salt, and the second excipient can be a sugar alcohol (such as mannitol). In more particular examples, the first excipient can be sodium sulfate, sodium chloride or magnesium lactate, and the second excipient can be mannitol. In other examples, the dry particles include an antifungal agent in crystalline particulate form, a stabilizer and one excipient, for example a sodium salt, a magnesium salt or an amino acid (e.g. leucine).

In one aspect, the invention relates to dry powder formulations comprising respirable dry particles comprising 1) an antifungal agent in crystalline particulate form, 2) a stabilizer, and 3) one or more excipients, with the proviso that the antifungal agent is not a polyene antifungal (e.g., amphotericin B).

In one preferred aspect, the invention relates to dry powder formulations comprising respirable dry particles comprising 1) a triazole antifungal agent in crystalline particulate form, 2) a stabilizer, and 3) one or more excipients.

In one aspect, the invention relates to dry powder formulations comprising respirable dry particles comprising about 50% to about 80% of a triazole antifungal agent in crystalline particulate form, about 4% to about 40% of a stabilizer, and about 1% to about 9% of one or more excipients; about 45% to about 85% of a triazole antifungal agent in crystalline particulate form, about 3% to about 15% of a stabilizer, about 3% to about 40% sodium salt, and about 1% to about 9% of one or more amino acids; about 45% to about 85% of a triazole antifungal agent in crystalline particulate form, about 3% to about 15% of a stabilizer, about 3% to about 40% sodium sulfate, and about 1% to about 9% of leucine; where all percentages are weight percentages, and all formulations add up to 100% on a dry basis.

In a particularly preferred aspect, the invention relates to dry powder formulations comprising respirable dry particles comprising 1) itraconazole in crystalline particulate form, 2) a stabilizer, and 3) one or more excipients. In this particularly preferred aspect, the dry powder formulation does not comprise lactose.

In one aspect, the invention relates to a dry powder formulation comprising 50% Itraconazole, 35% sodium sulfate, 10% leucine, and 5% polysorbate 80.

In one aspect, the invention relates to a dry powder formulation comprising 50% Itraconazole, 37% sodium sulfate, 8% leucine, and 5% polysorbate 80.

In another aspect, the invention relates to a dry powder formulation comprising 60% Itraconazole, 26% sodium sulfate, 8% leucine, and 6% polysorbate 80.

In another aspect, the invention relates to a dry powder formulation comprising 70% Itraconazole, 15% sodium, 8% leucine, and 7% polysorbate 80.

In another aspect, the invention relates to a dry powder formulation comprising 75% Itraconazole, 9.5% sodium sulfate, 8% leucine, and 7.5% polysorbate 80.

In another aspect, the invention relates to a dry powder formulation comprising 80% Itraconazole, 4% sodium sulfate, 8% leucine, and 8% polysorbate 80.

In another aspect, the invention relates to a dry powder formulation comprising 80% Itraconazole, 10% sodium sulfate, 2% leucine, and 8% polysorbate 80.

In another aspect, the invention relates to a dry powder formulation comprising 80% Itraconazole, 11% sodium sulfate, 1% leucine, and 8% polysorbate 80. The dry powders and/or respirable dry particles are preferably small, mass dense, and dispersible. To measure volumetric median geometric diameter (VMGD), a laser diffraction system may be used, e.g., a Spraytec system (particle size analysis instrument, Malvern Instruments) and a HELOS/RODOS system (laser diffraction sensor with dry dispensing unit, Sympatec GmbH). The respirable dry particles have a VMGD as measured by laser diffraction at the dispersion pressure setting (also called regulator pressure) of 1.0 bar at a maximum orifice ring pressure using a HELOS/RODOS system of about 10 microns or less, about 5 microns or less, about 4 µm or less, about 3 µm or less, about 1 µm to about 5 µm, about 1 µm to about 4 µm, about 1.5 µm to about 3.5 µm, about 2 µm to about 5 µm, about 2 µm to about 4 µm, or about 2 µm to about 3 µm. Preferably, the VMGD is about 5 microns or less or about 4 µm or less. In one aspect, the dry powders and/or respirable dry particles have a minimum VMGD of about 0.5 microns or about 1.0 micron.

The dry powders and/or respirable dry particles preferably have 1 bar/4 bar dispersibility ratio and/or 0.5 bar/4 bar dispersibility ratio of less than about 2.0 (e.g., about 0.9 to less than about 2), about 1.7 or less (e.g., about 0.9 to about 1.7) about 1.5 or less (e.g., about 0.9 to about 1.5), about 1.4 or less (e.g., about 0.9 to about 1.4), or about 1.3 or less (e.g., about 0.9 to about 1.3), and preferably have a 1 bar/4 bar and/or a 0.5 bar/4 bar of about 1.5 or less (e.g., about 1.0 to about 1.5), and/or about 1.4 or less (e.g., about 1.0 to about 1.4).

The dry powders and/or respirable dry particles preferably have a tap density of at least about 0.2 g/cm$^3$, of at least about 0.25 g/cm$^3$, a tap density of at least about 0.3 g/cm$^3$, of at least about 0.35 g/cm$^3$, a tap density of at least 0.4 g/cm$^3$. For example, the dry powders and/or respirable dry particles have a tap density of greater than 0.4 g/cm$^3$ (e.g., greater than 0.4 g/cm$^3$ to about 1.2 g/cm$^3$), a tap density of at least about 0.45 g/cm$^3$ (e.g., about 0.45 g/cm$^3$ to about 1.2 g/cm$^3$), at least about 0.5 g/cm$^3$ (e.g., about 0.5 g/cm$^3$ to about 1.2 g/cm$^3$), at least about 0.55 g/cm$^3$ (e.g., about 0.55 g/cm$^3$ to about 1.2 g/cm$^3$), at least about 0.6 g/cm$^3$ (e.g., about 0.6 g/cm$^3$ to about 1.2 g/cm$^3$) or at least about 0.6 g/cm$^3$ to about 1.0 g/cm$^3$. Alternatively, the dry powders and/or respirable dry particles preferably have a tap density of about 0.01 g/cm$^3$ to about 0.5 g/cm$^3$, about 0.05 g/cm$^3$ to about 0.5 g/cm$^3$, about 0.1 g/cm$^3$ to about 0.5 g/cm$^3$, about 0.1 g/cm$^3$ to about 0.4 g/cm$^3$, or about 0.1 g/cm$^3$ to about 0.4 g/cm$^3$. Alternatively, the dry powders and/or respirable dry particles have a tap density of about 0.15 g/cm$^3$ to about 1.0 g/cm$^3$.

The dry powders and/or respirable dry particles have a bulk density of at least about 0.1 g/cm$^3$, or at least about 0.8 g/cm$^3$. For example, the dry powders and/or respirable dry particles have a bulk density of about 0.1 g/cm$^3$ to about 0.6 g/cm$^3$, about 0.2 g/cm$^3$ to about 0.7 g/cm$^3$, about 0.3 g/cm$^3$ to about 0.8 g/cm$^3$.

The respirable dry particles, and the dry powders when the dry powders are respirable dry powders, preferably have an MMAD of less than 10 microns, preferably an MMAD of about 5 microns or less, or about 4 microns or less. In one aspect, the respirable dry powders and/or respirable dry particles preferably have a minimum MMAD of about 0.5 microns, or about 1.0 micron. In one aspect, the respirable dry powders and/or respirable dry particles preferably have a minimum MMAD of about 2.0 microns, about 3.0 microns, or about 4.0 microns.

The dry powders and/or respirable dry particles preferably have a FPF of less than about 5.6 microns (FPF<5.6 µm) of the total dose of at least about 35%, preferably at least about 45%, at least about 60%, between about 45% to about 80%, or between about 60% and about 80%.

The dry powders and/or respirable dry particles preferably have a FPF of less than about 3.4 microns (FPF<3.4 µm) of the total dose of at least about 20%, preferably at least about 25%, at least about 30%, at least about 40%, between about 25% and about 60%, or between about 40% and about 60%.

The dry powders and/or respirable dry particles preferably have a total water and/or solvent content of up to about 15% by weight, up to about 10% by weight, up to about 5% by weight, up to about 1%, or between about 0.01% and about 1%, or may be substantially free of water or other solvent.

The dry powders and/or respirable dry particles preferably may be administered with low inhalation energy. In order to relate the dispersion of powder at different inhalation flow rates, volumes, and from inhalers of different resistances, the energy required to perform the inhalation maneuver may be calculated. Inhalation energy can be calculated from the equation $E=R^2Q^2V$ where E is the inhalation energy in Joules, R is the inhaler resistance in kPa$^{1/2}$/LPM, Q is the steady flow rate in L/min and V is the inhaled air volume in L.

Healthy adult populations are predicted to be able to achieve inhalation energies ranging from 2.9 Joules for comfortable inhalations to 22 Joules for maximum inhalations by using values of peak inspiratory flow rate (PIFR) measured by Clarke et al. (Journal of Aerosol Med, 6(2), p. 99-110, 1993) for the flow rate Q from two inhaler resistances of 0.02 and 0.055 kPa$^{1/2}$/LPM, with an inhalation volume of 2 L based on both FDA guidance documents for dry powder inhalers and on the work of Tiddens et al. (Journal of Aerosol Med, 19(4), p. 456-465, 2006) who found adults averaging 2.2 L inhaled volume through a variety of DPIs.

Mild, moderate and severe adult COPD patients are predicted to be able to achieve maximum inhalation energies of 5.1 to 21 Joules, 5.2 to 19 Joules, and 2.3 to 18 Joules respectively. This is again based on using measured PIFR values for the flow rate Q in the equation for inhalation energy. The PIFR achievable for each group is a function of the inhaler resistance that is being inhaled through. The work of Broeders et al. (Eur Respir J, 18, p. 780-783, 2001) was used to predict maximum and minimum achievable PIFR through two dry powder inhalers of resistances 0.021 and 0.032 kPa$^{1/2}$/LPM for each.

Similarly, adult asthmatic patients are predicted to be able to achieve maximum inhalation energies of 7.4 to 21 Joules based on the same assumptions as the COPD population and PIFR data from Broeders et al.

Healthy adults and children, COPD patients, asthmatic patients ages 5 and above, and CF patients, for example, are capable of providing sufficient inhalation energy to empty and disperse the dry powder formulations of the invention.

The dry powders and/or respirable dry particles are preferably characterized by a high emitted dose, such as a CEPM of at least 75%, at least 80%, at least 85%, at least 90%, at least 95%, from a passive dry powder inhaler subject to a total inhalation energy of about 5 Joules, about 3.5 Joules, about 2.4 Joules, about 2 Joules, about 1 Joule, about 0.8 Joules, about 0.5 Joules, or about 0.3 Joules is applied to the dry powder inhaler. The receptacle holding the dry powders and/or respirable dry particles may contain about 5 mg, about 7.5 mg, about 10 mg, about 15 mg, about 20 mg, or about 30 mg. In one aspect, the dry powders and/or respirable dry particles are characterized by a CEPM of 80% or greater and a VMGD of 5 microns or less when emitted from a passive dry powder inhaler having a resistance of about 0.036 sqrt(kPa)/liters per minute under the following conditions: an air flow rate of 30 LPM, run for 3 seconds using a size 3 capsule that contains a total mass of 10 mg. In another aspect, the dry powders and/or respirable dry particles are characterized by a CEPM of 80% or greater and a VMGD of 5 microns or less when emitted from a passive dry powder inhaler having a resistance of about 0.036 sqrt(kPa)/liters per minute under the following conditions: an air flow rate of 20 LPM, run for 3 seconds using a size 3 capsule that contains a total mass of 10 mg. In a further aspect, the dry powders and/or respirable dry particles are characterized by a CEPM of 80% or greater and a VMGD of 5 microns or less when emitted from a passive dry powder inhaler having a resistance of about 0.036 sqrt(kPa)/liters per minute under the following conditions: an air flow rate of 15 LPM, run for 4 seconds using a size 3 capsule that contains a total mass of 10 mg.

The dry powder can fill the unit dose container, or the unit dose container can be at least 2% full, at least 5% full, at least 10% full, at least 20% full, at least 30% full, at least 40% full, at least 50% full, at least 60% full, at least 70% full, at least 80% full, or at least 90% full. The unit dose container can be a capsule (e.g., size 000, 00, OE, 0, 1, 2, 3, and 4, with respective volumetric capacities of 1.37 ml, 950 μl, 770 μl, 680 μl, 480 μl, 360 μl, 270 μl, and 200 μl). The capsule can be at least about 2% full, at least about 5% full, at least about 10% full, at least about 20% full, at least about 30% full, at least about 40% full, or at least about 50% full. The unit dose container can be a blister. The blister can be packaged as a single blister or as part of a set of blisters, for example, 7 blisters, 14 blisters, 28 blisters or 30 blisters. The one or more blister can be preferably at least 30% full, at least 50% full or at least 70% full.

An advantage of the invention is the production of powders that disperse well across a wide range of flow rates and are relatively flowrate independent. The dry powders and/or respirable dry particles of the invention enable the use of a simple, passive DPI for a wide patient population.

In particular aspects, the invention relates to dry powders and/or respirable dry particles that comprise antifungal agent in crystalline particulate form (e.g., particles of about 80 nm to about 1750 nm, such as about 60 nm to about 175 nm, about 150 nm to about 400 nm or about 1200 nm to about 1750 nm), a stabilizer, and optionally one or more excipients. Particular dry powders and respirable dry particles have the following formulations shown in Table 1. The dry powders and/or respirable dry particles described herein are preferably characterized by: 1) a VMGD at 1 bar as measured using a HELOS/RODOS system of about 10 microns or less, preferably about 5 microns or less; 2) a 1 bar/4 bar dispersibility ratio and/or a 0.5 bar/4 bar dispersibility ratio of about 1.5 or less, about 1.4 or less or about 1.3 or less; 3) a MMAD of about 10 microns or less, preferably about 5 microns or less; 4) a FPF<5.6 μm of the total dose of at least about 45% or at least about 60%; and/or 5) a FPF<3.4 μm of the total dose of at least about 25% or at least about 40%. If desired, the dry powders and/or respirable dry particles are further characterized by a tap density of about 0.2 g/cm$^3$ or greater, about 0.3 g/cm$^3$ or greater, about 0.4 g/cm$^3$ or greater, greater than 0.4 g/cm$^3$, about 0.45 g/cm$^3$ or greater or about 0.5 g/cm$^3$ or greater.

TABLE 1

| Formulation | Antifungal (wt %) | Excipients (wt %) | Stabilizer (wt %) | Antifungal subparticle size (left column), and range (right column) (Dv50 nm) | |
|---|---|---|---|---|---|
| A (I) | Itraconazole 20% | Sodium sulfate 39% Mannitol 39% | PS80 2% | 124 | 60-175 |
| B (II) | Itraconazole 50% | Sodium sulfate 22.5% Mannitol 22.5% | PS80 5% | 124 | 60-175 |
| C (III) | Itraconazole 20% | Sodium chloride 62.4% Leucine 15.6% | PS80 2% | 124 | 60-175 |
| D (IV) | Itraconazole 50% | Sodium chloride 36% Leucine 9% | PS80 5% | 124 | 60-175 |
| E (V) | Itraconazole 20% | Magnesium lactate 66.3% Leucine 11.7% | PS80 2% | 124 | 60-175 |
| F (VI) | Itraconazole 50% | Magnesium lactate 38.25% Leucine 6.75% | PS80 5% | 124 | 60-175 |
| G (VII) | Itraconazole 50% | Sodium sulfate 33.25% Leucine 14.25% | Oleic acid 2.5% | 120 | 60-175 |
| H (VIII) | Itraconazole 70% | Sodium sulfate 13.25% Leucine 13.25% | Oleic acid 3.5% | 120 | 60-175 |
| I | Itraconazole 50% | Magnesium lactate 33.25% Leucine 14.25% | Oleic acid 2.5% | 120 | 60-175 |
| J | Itraconazole 70% | Magnesium lactate 13.25% Leucine 13.25% | Oleic acid 3.5% | 120 | 60-175 |
| K (XI) | Itraconazole 50% | Sodium sulfate 35% Leucine 12.5% | Oleic acid 2.5% | 126 | 60-175 |
| L (XII) | Itraconazole 50% | Sodium sulfate 35% Leucine 10% | PS80 5% | 132 | 60-175 |
| M (XIII) | Itraconazole 50% | Sodium sulfate 35% Leucine 10% | PS80 5% | 198 | 150-250 |
| N (XIV) | Itraconazole 50% | Sodium sulfate 35% Leucine 10% | PS80 5% | 258 | 200-325 |
| O (XV) | Itraconazole 50% | Sodium sulfate 35% Leucine 10% | PS80 5% | 1600 | 1200-1500 |

TABLE 1-continued

| Formulation | Antifungal (wt %) | Excipients (wt %) | Stabilizer (wt %) | Antifungal subparticle size (left column) (Dv50 nm) | and range (right column) (Dv50 nm) |
|---|---|---|---|---|---|
| P (XVI) | Itraconazole 50% | Sodium sulfate 35%, Leucine 10% | PS80 <5% | 1510 | 1200-1500 |
| Q (XVII) | Amphotericin B 50% | Sodium sulfate 35%, Leucine 10% | PS80 5% | 120 | 60-175 |
| R (XVIII) | Amphotericin B 50% | Sodium chloride 35%, Leucine 10% | PS80 5% | 120 | 60-175 |
| S (XIX) | Itraconazole 50% | Sodium sulfate 35%, Leucine 15% | N/A | N/A | N/A |
| XX | Itraconazole 50% | Sodium sulfate 35%, Leucine 15% | N/A | N/A | N/A |
| XXI | Itraconazole 50% | Sodium sulfate 35%, Leucine 10% | PS80 5% | 130 | 60-175 |
| XXII | Itraconazole 50% | Sodium sulfate 35%, Leucine 11.57% | Oleic acid 3.43% | 115 | 60-175 |
| XXIII | Itraconazole 50% | Sodium sulfate 35%, Leucine 13.75% | PS80 1.25% | 1640 | 1200-1500 |
| XXIV | Itraconazole 50% | Sodium sulfate 37%, Leucine 8% | PS80 5% | 130 | 60-175 |
| XXV | Itraconazole 60% | Sodium sulfate 26%, Leucine 8% | PS80 6% | 130 | 60-175 |
| XXVI | Itraconazole 70% | Sodium sulfate 15%, Leucine 8% | PS80 7% | 130 | 60-175 |
| XXVII | Itraconazole 75% | Sodium sulfate 9.5%, Leucine 8% | PS80 7.5% | 130 | 60-175 |
| XXVIII | Itraconazole 80% | Sodium sulfate 4%, Leucine 8% | PS80 8% | 130 | 60-175 |
| XXIX | Itraconazole 80% | Sodium sulfate 10%, Leucine 2% | PS80 8% | 130 | 60-175 |
| XXX | Itraconazole 80% | Sodium sulfate 11%, Leucine 1% | PS80 8% | 130 | 60-175 |

The dry powders and/or respirable dry particles described by any of the ranges or specifically disclosed formulations, characterized in the previous paragraph, may be filled into a receptacle, for example a capsule or a blister. When the receptacle is a capsule, the capsule is, for example, a size 2 or a size 3 capsule, and is preferably a size 3 capsule. The capsule material may be, for example, gelatin or HPMC (Hydroxypropyl methylcellulose), and is preferably HPMC.

The dry powder and/or respirable dry particles described and characterized above may be contained in a dry powder inhaler (DPI). The DPI may be a capsule-based DPI or a blister-based DPI, and is preferably a capsule-based DPI. More preferably, the dry powder inhaler is selected from the RSO1 family of dry powder inhalers (Plastiape S.p.A., Italy). More preferably, the dry powder inhaler is selected from the RSO1 HR or the RSO1 UHR2. Most preferably, the dry powder inhaler is the RSO1 HR.

Methods for Preparing Dry Powders and Dry Particles

The respirable dry particles and dry powders can be prepared using any suitable method, with the proviso that the the dry powder formulation cannot be an extemporaneous dispersion. Many suitable methods for preparing dry powders and/or respirable dry particles are conventional in the art, and include single and double emulsion solvent evaporation, spray drying, spray-freeze drying, milling (e.g., jet milling), blending, solvent extraction, solvent evaporation, phase separation, simple and complex coacervation, interfacial polymerization, suitable methods that involve the use of supercritical carbon dioxide ($CO_2$), sonocrystalliztion, nanoparticle aggregate formation and other suitable methods, including combinations thereof. Respirable dry particles can be made using methods for making microspheres or microcapsules known in the art. These methods can be employed under conditions that result in the formation of respirable dry particles with desired aerodynamic properties (e.g., aerodynamic diameter and geometric diameter). If desired, respirable dry particles with desired properties, such as size and density, can be selected using suitable methods, such as sieving.

Suitable methods for selecting respirable dry particles with desired properties, such as size and density, include wet sieving, dry sieving, and aerodynamic classifiers (such as cyclones).

The respirable dry particles are preferably spray dried. Suitable spray-drying techniques are described, for example, by K. Masters in "Spray Drying Handbook", John Wiley &

Sons, New York (1984). Generally, during spray-drying, heat from a hot gas such as heated air or nitrogen is used to evaporate a solvent from droplets formed by atomizing a continuous liquid feed. When hot air is used, the moisture in the air is at least partially removed before its use. When nitrogen is used, the nitrogen gas can be run "dry", meaning that no additional water vapor is combined with the gas. If desired the moisture level of the nitrogen or air can be set before the beginning of spray dry run at a fixed value above "dry" nitrogen. If desired, the spray drying or other instruments, e.g., jet milling instrument, used to prepare the dry particles can include an inline geometric particle sizer that determines a geometric diameter of the respirable dry particles as they are being produced, and/or an inline aerodynamic particle sizer that determines the aerodynamic diameter of the respirable dry particles as they are being produced.

For spray drying, solutions, emulsions or suspensions that contain the components of the dry particles to be produced in a suitable solvent (e.g., aqueous solvent, organic solvent, aqueous-organic mixture or emulsion) are distributed to a drying vessel via an atomization device. For example, a nozzle or a rotary atomizer may be used to distribute the solution or suspension to the drying vessel. The nozzle can be a two-fluid nozzle, which can be in an internal mixing setup or an external mixing setup. Alternatively, a rotary atomizer having a 4- or 24-vaned wheel may be used. Examples of suitable spray dryers that can be outfitted with a rotary atomizer and/or a nozzle, include, a Mobile Minor Spray Dryer or the Model PSD-1, both manufactured by GEA Niro, Inc. (Denmark), Büchi B-290 Mini Spray Dryer (BÜCHI Labortechnik AG, Flawil, Switzerland), ProCepT Formatrix R&D spray dryer (ProCepT nv, Zelzate, Belgium), among several other spray dryer options. Actual spray drying conditions will vary depending, in part, on the composition of the spray drying solution or suspension and material flow rates. The person of ordinary skill will be able to determine appropriate conditions based on the compositions of the solution, emulsion or suspension to be spray dried, the desired particle properties and other factors. In general, the inlet temperature to the spray dryer is about 90° C. to about 300° C. The spray dryer outlet temperature will vary depending upon such factors as the feed temperature and the properties of the materials being dried. Generally, the outlet temperature is about 50° C. to about 150° C. If desired, the respirable dry particles that are produced can be fractionated by volumetric size, for example, using a sieve, or fractioned by aerodynamic size, for example, using a cyclone, and/or further separated according to density using techniques known to those of skill in the art.

To prepare the respirable dry particles of the invention, generally, an emulsion or suspension that contains the desired components of the dry powder (i.e., a feedstock) is prepared and spray dried under suitable conditions. Preferably, the dissolved or suspended solids concentration in the feedstock is at least about 1 g/L, at least about 2 g/L, at least about 5 g/L, at least about 10 g/L, at least about 15 g/L, at least about 20 g/L, at least about 30 g/L, at least about 40 g/L, at least about 50 g/L, at least about 60 g/L, at least about 70 g/L, at least about 80 g/L, at least about 90 g/L or at least about 100 g/L. The feedstock can be provided by preparing a single solution, suspension or emulsion by dissolving, suspending, or emulsifying suitable components (e.g., salts, excipients, other active ingredients) in a suitable solvent. The solution, emulsion or suspension can be prepared using any suitable methods, such as bulk mixing of dry and/or liquid components or static mixing of liquid components to form a combination. For example, a hydrophilic component (e.g., an aqueous solution) and a hydrophobic component (e.g., an organic solution) can be combined using a static mixer to form a combination. The combination can then be atomized to produce droplets, which are dried to form respirable dry particles. Preferably, the atomizing step is performed immediately after the components are combined in the static mixer. Alternatively, the atomizing step is performed on a bulk mixed solution.

The feedstock can be prepared using any solvent in which the antifungal agent in particulate form has low solubility, such as an organic solvent, an aqueous solvent or mixtures thereof. Suitable organic solvents that can be employed include but are not limited to alcohols such as, for example, ethanol, methanol, propanol, isopropanol, butanols, and others. Other organic solvents include but are not limited to tetrahydrofuran (THF), perfluorocarbons, dichloromethane, chloroform, ether, ethyl acetate, methyl tert-butyl ether and others. Co-solvents that can be employed include an aqueous solvent and an organic solvent, such as, but not limited to, the organic solvents as described above. Aqueous solvents include water and buffered solutions. A preferred solvent is water.

Various methods (e.g., static mixing, bulk mixing) can be used for mixing the solutes and solvents to prepare feedstocks, which are known in the art. If desired, other suitable methods of mixing may be used. For example, additional components that cause or facilitate the mixing can be included in the feedstock. For example, carbon dioxide produces fizzing or effervescence and thus can serve to promote physical mixing of the solute and solvents.

The feedstock or components of the feedstock can have any desired pH, viscosity or other properties. If desired, a pH buffer can be added to the solvent or co-solvent or to the formed mixture. Generally, the pH of the mixture ranges from about 3 to about 8.

Dry powder and/or respirable dry particles can be fabricated and then separated, for example, by filtration or centrifugation by means of a cyclone, to provide a particle sample with a preselected size distribution. For example, greater than about 30%, greater than about 40%, greater than about 50%, greater than about 60%, greater than about 70%, greater than about 80%, or greater than about 90% of the respirable dry particles in a sample can have a diameter within a selected range. The selected range within which a certain percentage of the respirable dry particles fall can be, for example, any of the size ranges described herein, such as between about 0.1 to about 3 microns VMGD.

The suspension may be a nano-suspension, similar to an intermediate for making dry powder containing nano-crystalline drug.

The dry powder may be a drug embedded in a matrix material, such as sodium sulfate and leucine. Optionally, the dry powder may be spray dried such that the dry particles are small, dense, and dispersible.

The dry powders can consist solely of the respirable dry particles described herein without other carrier or excipient particles (referred to as "neat powders"). If desired the dry powders can comprise blends of the respirable dry particles described herein and other carrier or excipient particles, such as lactose carrier particles that are greater than 10 microns, 20 microns to 500 microns, and preferably between 25 microns and 250 microns.

In a preferred embodiment, the dry powders do not contain carrier particles. In one aspect, the crystalline drug particles are embedded in a matrix comprising excipient and/or stabilizer. The dry powder may comprise respirable dry particles of uniform content, wherein each particle contains crystalline drug. Thus, as used herein, "uniform content" means that every respirable particle contains some amount of antifungal agent in crystalline particulate form, stabilizer, and excipient.

The dry powders can comprise respirable dry particles wherein at least 98%, at least 99%, or substantially all of the particles (by weight) contain an antifungal agent.

The dry powders can comprise crystalline drug particles distributed throughout a matrix comprising one or more excipients. The excipients can comprise any number of salts, sugars, lipids, amino acids, surfactants, polymers, or other components suitable for pharmaceutical use. Preferred excipients include sodium sulfate and leucine. The dry powders are typically manufactured by first processing the crystalline drug to adjust the particle size using any number of techniques that are familiar to those of skill in the art (e.g., wet milling, jet milling). The crystalline drug is processed in an antisolvent with a stabilizer to form a suspension. Preferred stabilizers include polysorbate (Tween) 80 and oleic acid. The stabilized suspension of crystalline drug is then spray dried with the one or more additional excipients. The resulting dry particles comprise crystalline drug dispersed throughout an excipient matrix with each dry particle having a homogenous composition.

In a particular embodiment, a dry powder of the present invention is made by starting with crystalline drug (e.g., itraconazole), which is usually obtainable in a micro-crystalline size range. The particle size of the micro-crystalline drug is reduced into the nano-crystalline size using any of a number of techniques familiar to those of skill in the art, including but not limited to, high-pressure homogenization, high-shear homogenization, jet-milling, pin milling, micro-fluidization, or wet milling (also known as ball milling, pearl milling or bead milling). Wet milling is often preferred, as it is able to achieve a wide range of particle size distributions, including those in the nanometer (<1 μm) size domain. What becomes especially important in the sub-micron size domain is the use of surface stabilizing components, such as surfactants (e.g., Tween 80). Surfactants enable the creation of submicron particles during milling and the formation of physically stable suspensions, as they sequester the many high energy surfaces created during milling preventing aggregation and sedimentation. Thus, the presence of the surfactant is important to spray drying homogenous micro-particles as the surfactant allows for the formation of a uniform and stable suspension ensuring compositional homogeneity across particles. The use of surfactant allows for formation of micro-suspension or nano-suspensions. With the surfactant, the nano-crystalline drug (e.g., ITZ) particles are suspended in a stable colloidal suspension in the anti-solvent. The anti-solvent for the drug can utilize water, or a combination of water and other miscible solvents such as alcohols or ketones as the continuous anti-solvent phase for the colloidal suspension. A spray drying feedstock may be prepared by dissolving the soluble components in a desired solvent(s) followed by dispersing the surfactant-stabilized crystalline drug nanosuspension in the resulting feedstock while mixing, although the process is not limited to this specific order of operations.

Methods for analyzing the dry powders and/or respirable dry particles are found in the Exemplification section below.

Therapeutic Use and Methods

The dry powders and/or respirable dry particles of the present invention are suitable for administration to the respiratory tract, for example to a subject in need thereof for the treatment of respiratory (e.g., pulmonary) diseases, such as cystic fibrosis, asthma, especially severe asthma, and severely immunocompromised patients. This treatment is especially useful in treating *aspergillus* infections. This treatment is also useful for treating fungal infections sensitive to itraconazole. Another aspect of the invention is treating allergic bronchopulmonary aspergillosis (ABPA), for example, in patients with pulmonary disease such as asthma or cystic fibrosis.

In other aspects, the invention is a method for the treatment, reduction in incidence or severity, or prevention of acute exacerbations caused by a fungal infection in the respiratory tract, such as an *aspergillus* infection. In another aspect, the invention is a method for the treatment, reduction in incidence or severity, or prevention of exacerbations caused by a fungal infection in the respiratory trat, such as an *aspergillus* infection. In another aspect, the invention is a method for the treatment, reduction in incidence or severity, or prevention of exacerbations caused by allergic bronchopulmonary aspergillosis (ABPA), for example, in patients with pulmonary disease such as asthma or cystic fibrosis.

In other aspects, the invention is a method for relieving the symptoms of a respiratory disease and/or a chronic pulmonary disease, such as cystic fibrosis, asthma, especially severe asthma and severely immunocompromised patients. In another aspect, the invention is a method for relieving the symptoms of allergic bronchopulmonary aspergillosis (ABPA) in these patient populations. In yet another aspect, the invention is a method for reducing inflammation, sparing the use of steroids, or reducing the need for steroidal treatment.

In other aspects, the invention is a method for improving lung function of a patient with a respiratory disease and/or a chronic pulmonary disease, such as such as cystic fibrosis, asthma, especially severe asthma and severely immunocompromised patients. In another aspect, the invention is a method for improving lung function of a patient with allergic bronchopulmonary aspergillosis (ABPA).

The dry powders and/or respirable dry particles can be administered to the respiratory tract of a subject in need thereof using any suitable method, such as instillation techniques, and/or an inhalation device, such as a dry powder inhaler (DPI) or metered dose inhaler (MDI). A number of DPIs are available, such as, the inhalers disclosed is U.S. Pat. Nos. 4,995,385 and 4,069,819, Spinhaler® (Fisons, Loughborough, U.K.), Rotahalers®, Diskhaler® and Diskus® (GlaxoSmithKline, Research Triangle Technology Park, N.C.), FlowCaps® (Hovione, Loures, Portugal), Inhalators® (Boehringer-Ingelheim, Germany), Aerolizer® (Novartis, Switzerland), high-resistance, ultrahigh-resistance and low-resistance RS01 (Plastiape, Italy) and others known to those skilled in the art.

The following scientific journal articles are incorporated by reference for their thorough overview of the following dry powder inhaler (DPI) configurations: 1) Single-dose Capsule DPI, 2) Multi-dose Blister DPI, and 3) Multi-dose Reservoir DPI. N. Islam, E. Gladki, "Dry powder inhalers (DPIs)—A review of device reliability and innovation", International Journal of Pharmaceuticals, 360(2008):1-11. H. Chystyn, "Diskus Review", International Journal of Clinical Practice, June 2007, 61, 6, 1022-1036. H. Steckel, B. Muller, "In vitro evaluation of dry powder inhalers I: drug deposition of commonly used devices", International Journal of Pharmaceuticals, 154(1997):19-29. Some representative capsule-based DPI units are RS-01 (Plastiape, Italy), Turbospin® (PH&T, Italy), Brezhaler® (Novartis, Switzerland), Aerolizer (Novartis, Switzerland), Podhaler® (Novartis, Switzerland), HandiHaler® (Boehringer Ingelheim, Germany), AIR® (Civitas, Mass.), Dose One® (Dose One, Maine), and Eclipse® (Rhone Poulenc Rorer). Some representative unit dose DPIs are Conix® (3M, Minnesota), Cricket® (Mannkind, Calif.), Dreamboat® (Mannkind, Calif.), Occoris® (Team Consulting, Cambridge, UK), Solis® (Sandoz), Trivair® (Trimel Biopharma, Canada), Twincaps® (Hovione, Loures, Portugal). Some representative blister-based DPI units are Diskus® (GlaxoSmithKline (GSK), UK), Diskhaler® (GSK), Taper Dry® (3M, Minnisota), Gemini® (GSK), Twincer® (University of Groningen, Netherlands), Aspirair® (Vectura, UK), Acu-Breathe® (Respirics, Minnesota, USA), Exubra® (Novartis, Switzerland), Gyrohaler® (Vectura, UK), Omnihaler® (Vectura, UK), Microdose® (Microdose Therapeutix, USA), MuWhaler® (Cipla, India) Prohaler® (Aptar), Technohaler® (Vectura, UK), and Xcelovair® (Mylan, Pa.). Some representative reservoir-based DPI units are Clickhaler® (Vectura), Next DPI® (Chiesi), Easyhaler® (Orion), Novolizer® (Meda), Pulmojet® (sanofi-aventis), Pulvinal® (Chiesi), Skyehaler® (Skyepharma), Duohaler® (Vectura), Taifun® (Akela), Flexhaler® (AstraZeneca, Sweden), Turbuhaler® (AstraZeneca, Sweden), and Twisthaler® (Merck), and others known to those skilled in the art.

Generally, inhalation devices (e.g., DPIs) are able to deliver a maximum amount of dry powder or dry particles in a single inhalation, which is related to the capacity of the blisters, capsules (e.g., size 000, 00, OE, 0, 1, 2, 3 and 4, with respective volumetric capacities of 1.37 ml, 950 µl, 770 µl, 680 µl, 480 µl, 360 µl, 270 µl and 200 µl) or other means that contain the dry powders and/or respirable dry particles within the inhaler. Preferably, the blister has a volume of about 360 microliters or less, about 270 microliters or less, or more preferably, about 200 microliters or less, about 150 microliters or less, or about 100 microliters or less. Preferably, the capsule is a size 2 capsule, or a size 4 capsule. More preferably, the capsule is a size 3 capsule. Accordingly, delivery of a desired dose or effective amount may require two or more inhalations. Preferably, each dose that is administered to a subject in need thereof contains an effective amount of respirable dry particles or dry powder and is administered using no more than about 4 inhalations. For example, each dose of dry powder or respirable dry particles can be administered in a single inhalation or 2, 3, or 4 inhalations. The dry powders and/or respirable dry particles are preferably administered in a single, breath-activated step using a passive DPI. When this type of device is used, the energy of the subject's inhalation both disperses the respirable dry particles and draws them into the respiratory tract.

Dry powders and/or respirable dry particles suitable for use in the methods of the invention can travel through the upper airways (i.e., the oropharynx and larynx), the lower airways, which include the trachea followed by bifurcations into the bronchi and bronchioli, and through the terminal bronchioli which in turn divide into respiratory bronchioli leading then to the ultimate respiratory zone, the alveoli or the deep lung. In one embodiment of the invention, most of the mass of respirable dry particles deposit in the deep lung. In another embodiment of the invention, delivery is primarily to the central airways. In another embodiment, delivery is to the upper airways. In a preferred embodiment, most of the mass of the respirable dry particles deposit in the conducting airways.

If desired or indicated, the dry powders and respirable dry particles described herein can be administered with one or more other therapeutic agents. The other therapeutic agents can be administered by any suitable route, such as orally, parenterally (e.g., intravenous, intra-arterial, intramuscular, or subcutaneous injection), topically, by inhalation (e.g., intrabronchial, intranasal or oral inhalation, intranasal drops), rectally, vaginally, and the like. The respirable dry particles and dry powders can be administered before, substantially concurrently with, or subsequent to administration of the other therapeutic agent. Preferably, the dry powders and/or respirable dry particles and the other therapeutic agent are administered so as to provide substantial overlap of their pharmacologic activities.

The dry powders and respirable dry particles described herein are intended to be inhaled as such, and the present invention excludes the use of the dry powder formulation in making an extemporaneous dispersion. An extemporaneous dispersion is known by those skilled in the art as a preparation completed just before use, which means right before the administration of the drug to the patient. As used herein, the term "extemporaneous dispersion" refers to all of the cases in which the solution or suspension is not directly produced by the pharmaceutical industry and commercialized in a ready to be used form, but is prepared in a moment that follows the preparation of the dry solid composition, usually in a moment close to the administration to the patient.

Exemplification

Materials used in the following Examples and their sources are listed below. Sodium chloride, sodium sulfate, polysorbate 80, oleic acid, ammonium hydroxide, mannitol, magnesium lactate, and L-leucine were obtained from Sigma-Aldrich Co. (St. Louis, Mo.), Spectrum Chemicals (Gardena, Calif.), Applichem (Maryland Heights, Mo.), Alfa Aesar (Tewksbury, Mass.), Thermo Fisher (Waltham, Mass.), Croda Chemicals (East Yorkshire, United Kingdom) or Merck (Darmstadt, Germany). Itraconazole was obtained from Neuland (Princeton, N.J.) or SMS Pharmaceutical ltd (Telengana State, India). Amphotericin B was obtained from Synbiotics Ltd (Ahmedabad, India). Ultrapure (Type II ASTM) water was from a water purification system (Millipore Corp., Billerica, Mass.), or equivalent.

Methods:

Geometric of Volume Diameter of Suspensions. Volume median diameter (x50 or Dv50), which may also be referred to as volume median geometric diameter (VMGD), of the active agent suspensions was determined using a laser diffraction technique. The equipment consisted of a Horiba LA-950 instrument outfitted with an automated recirculation system for sample handling and removal or a fixed-volume sample cuvette. The sample to a dispersion media, consisting of either deionized water or deionized water with less than 0.5% of a surfactant such as polysorbate 80 or sodium dodecyl sulfate. Ultrasonic energy can be applied to aid in dispersion of the suspension. When the laser transmission was in the correct range, the sample was sonicated for 60 seconds at a setting of 5. The sample was then measured and the particle size distribution reported.

Geometric or Volume Diameter of Dry Powders. Volume median diameter (x50 or Dv50), which may also be referred to as volume median geometric diameter (VMGD), of the dry powder formulations was determined using a laser diffraction technique. The equipment consisted of a HELOS diffractometer and a RODOS dry powder disperser (Sympatec, Inc., Princeton, N.J.). The RODOS disperser applies a shear force to a sample of particles, controlled by the regulator pressure (typically set at 1.0 bar with maximum orifice ring pressure) of the incoming compressed dry air. The pressure settings may be varied to vary the amount of energy used to disperse the powder. For example, the dispersion energy may be modulated by changing the regulator pressure from 0.2 bar to 4.0 bar. Powder sample is dispensed from a microspatula into the RODOS funnel. The dispersed particles travel through a laser beam where the resulting diffracted light pattern produced is collected, typically using an R1 lens, by a series of detectors. The ensemble diffraction pattern is then translated into a volume-based particle size distribution using the Fraunhofer diffraction model, on the basis that smaller particles diffract light at larger angles. Using this method, the span of the distribution was also determined per the formula (Dv[90]−Dv[10]/Dv [50]. The span value gives a relative indication of the polydispersity of the particle size distribution.

Aerodynamic Performance Via Andersen Cascade Impactor The aerodynamic properties of the powders dispersed from an inhaler device were assessed with an Mk-II 1 ACFM Andersen Cascade Impactor (Copley Scientific Limited, Nottingham, UK) (ACI). The ACI instrument was run in controlled environmental conditions of 18 to 25° C. and relative humidity (RH) between 25 and 35%. The instrument consists of eight stages that separate aerosol particles based on inertial impaction. At each stage, the aerosol stream passes through a set of nozzles and impinges on a corresponding impaction plate. Particles having small enough inertia will continue with the aerosol stream to the next stage, while the remaining particles will impact upon the plate. At each successive stage, the aerosol passes through nozzles at a higher velocity and aerodynamically smaller particles are collected on the plate. After the aerosol passes through the final stage, a filter collects the smallest particles that remain, called the "final collection filter". Gravimetric and/or chemical analyses can then be performed to determine the particle size distribution. A short stack cascade impactor, also referred to as a collapsed cascade impactor, is also utilized to allow for reduced labor time to evaluate two aerodynamic particle size cut-points. With this collapsed cascade impactor, stages are eliminated except those required to establish fine and coarse particle fractions. The impaction techniques utilized allowed for the collection of two or eight separate powder fractions. The capsules (HPMC, Size 3; Capsugel Vcaps, Peapack, N.J.) were filled with powder to a specific weight and placed in a hand-held, breath-activated dry powder inhaler (DPI) device, the high resistance RS01 DPI or the ultra-high resistance UHR2 DPI (both by Plastiape, Osnago, Italy). The capsule was punctured and the powder was drawn through the cascade impactor operated at a flow rate of 60.0 L/min for 2.0 s. At this flowrate, the calibrated cut-off diameters for the eight stages are 8.6, 6.5, 4.4, 3.3, 2.0, 1.1, 0.5 and 0.3 microns and for the two stages used with the short stack cascade impactor, based on the Andersen Cascade Impactor, the cut-off diameters are 5.6 microns and 3.4 microns. The fractions were collected by placing filters in the apparatus and determining the amount of powder that impinged on them by gravimetric measurements or chemical measurements on an HPLC.

Aerodynamic Performance Via Next Generation Impactor. The aerodynamic properties of the powders dispersed from an inhaler device were assessed with a Next Generation Impactor (Copley Scientific Limited, Nottingham, UK) (NGI). For measurements utilizing the NGI, the NGI instrument was run in controlled environmental conditions of 18 to 25° C. and relative humidity (RH) between 25 and 35%. The instrument consists of seven stages that separate aerosol particles based on inertial impaction and can be operated at a variety of air flow rates. At each stage, the aerosol stream passes through a set of nozzles and impinges on a corresponding impaction surface. Particles having small enough inertia will continue with the aerosol stream to the next stage, while the remaining particles will impact upon the surface. At each successive stage, the aerosol passes through nozzles at a higher velocity and aerodynamically smaller particles are collected on the plate. After the aerosol passes through the final stage, a micro-orifice collector collects the smallest particles that remain. Gravimetric and/or chemical analyses can then be performed to determine the particle size distribution. The capsules (HPMC, Size 3; Capsugel Vcaps, Peapack, N.J.) were filled with powder to a specific weight and placed in a hand-held, breath-activated dry powder inhaler (DPI) device, the high resistance RS01 DPI or the ultra-high resistance RS01 DPI (both by Plastiape, Osnago, Italy). The capsule was punctured and the powder was drawn through the cascade impactor operated at a specified flow rate for 2.0 Liters of inhaled air. At the specified flow rate, the cut-off diameters for the stages were calculated. The fractions were collected by placing wetted filters in the apparatus and determining the amount of powder that impinged on them by chemical measurements on an HPLC.

Fine Particle Dose The fine particle dose indicates the mass of one or more therapeutics in a specific size range and can be used to predict the mass which will reach a certain region in the respiratory tract. The fine particle dose can be measured gravimetrically or chemically via either an ACI or NGI. If measured gravimetrically, since the dry particles are assumed to be homogenous, the mass of the powder on each stage and collection filter can be multiplied by the fraction of therapeutic agent in the formulation to determine the mass of therapeutic. If measured chemically, the powder from each stage or filter is collected, separated, and assayed for example on an HPLC to determine the content of the therapeutic. The cumulative mass deposited on each of the stages at the specified flow rate is calculated and the cumulative mass corresponding to a 5.0 micrometer diameter particle is interpolated. This cumulative mass for a single dose of powder, contained in one or more capsules, actuated into the impactor is equal to the fine particle dose less than 5.0 microns (FPD<5.0 microns).

Mass Median Aerodynamic Diameter. Mass median aerodynamic diameter (MMAD) was determined using the information obtained by the Andersen Cascade Impactor (ACI). The cumulative mass under the stage cut-off diameter is calculated for each stage and normalized by the recovered dose of powder. The MMAD of the powder is then calculated by linear interpolation of the stage cut-off diameters that bracket the 50th percentile. An alternative method of measuring the MMAD is with the Next Generation Impactor (NGI). Like the ACI, the MMAD is calculated with the cumulative mass under the stage cut-off diameter is calculated for each stage and normalized by the recovered dose of powder. The MMAD of the powder is then calculated by linear interpolation of the stage cut-off diameters that bracket the 50th percentile.

Emitted Geometric or Volume Diameter. The volume median diameter (Dv50) of the powder after it is emitted from a dry powder inhaler, which may also be referred to as volume median geometric diameter (VMGD), was determined using a laser diffraction technique via the Spraytec diffractometer (Malvern, Inc.). Powder was filled into size 3 capsules (V-Caps, Capsugel) and placed in a capsule based dry powder inhaler (RS01 Model 7 High resistance, Plastiape, Italy), or DPI, and the DPI sealed inside a cylinder. The cylinder was connected to a positive pressure air source with steady air flow through the system measured with a mass flow meter and its duration controlled with a timer controlled solenoid valve. The exit of the dry powder inhaler was exposed to room pressure and the resulting aerosol jet passed through the laser of the diffraction particle sizer (Spraytec) in its open bench configuration before being captured by a vacuum extractor. The steady air flow rate through the system was initiated using the solenoid valve. A steady air flow rate was drawn through the DPI typically at 60 L/min for a set duration, typically of 2 seconds. Alternatively, the air flow rate drawn through the DPI was sometimes run at 15 L/min, 20 L/min, or 30 L/min. The resulting geometric particle size distribution of the aerosol was calculated from the software based on the measured scatter pattern on the photodetectors with samples typically taken at 1000 Hz for the duration of the inhalation. The Dv50, GSD, FPF<5.0 µm measured were then averaged over the duration of the inhalation.

The Emitted Dose (ED) refers to the mass of therapeutic which exits a suitable inhaler device after a firing or dispersion event. The ED is determined using a method based on USP Section 601 Aerosols, Metered-Dose Inhalers and Dry Powder Inhalers, Delivered-Dose Uniformity, Sampling the Delivered Dose from Dry Powder Inhalers, United States Pharmacopeia convention, Rockville, Md., 13th Revision, 222-225, 2007. Contents of capsules are dispersed using either the RS01 HR inhaler at a pressure drop of 4 kPa or a typical flow rate of 60 LPM or the UHR2 RS01 at a pressure drop of 4 kPa and a typical flow rate of 39 LPM. The emitted powder is collected on a filter in a filter holder sampling apparatus. The sampling apparatus is rinsed with a suitable solvent such as water and analyzed using an HPLC method. For gravimetric analysis a shorter length filter holder sampling apparatus is used to reduce deposition in the apparatus and the filter is weighed before and after to determine the mass of powder delivered from the DPI to the filter. The emitted dose of therapeutic is then calculated based on the content of therapeutic in the delivered powder. Emitted dose can be reported as the mass of therapeutic delivered from the DPI or as a percentage of the filled dose.

Thermogravimetric Analysis: Thermogravimetric analysis (TGA) was performed using either the Q500 model or the Discovery model thermogravimetric analyzer (TA Instruments, New Castle, Del.). The samples were either placed into an open aluminum DSC pan or a sealed aluminum DSC pan that was then automatically punched open prior to the time of test. Tare weights were previously recorded by the instrument. The following method was employed: Ramp 5.00° C./min from ambient (−35° C.) to 200° C. The weight loss was reported as a function of temperature up to 140° C. TGA allows for the calculation of the content of volatile compounds within the dry powder. When utilizing processes with water alone, or water in conjunction with volatile solvents, the weight loss via TGA is a good estimate of water content.

X-Ray Powder Diffraction: The crystalline character of the formulations was assessed via powder X-ray diffraction (PXRD). A 20-30 mg sample of material is analyzed in a powder X-ray diffractometer (D8 Discover with LINXEYE detector; Bruker Corporation, Billerica, Mass. or equivalent) using a Cu X-ray tube with 1.5418 A at a data accumulation time 1.2 second/step over a scan range of 5 to 45° 2θ and a step size of 0.02° 2θ.

Itraconazole Content/Purity using HPLC. A high performance liquid chromatography (HPLC) method utilizing a reverse phase C18 column coupled to an ultraviolet (UV) detector has been developed for the identification, bulk content, assay, CUPMD and impurities analysis of PUR1900 formulations. The reverse phase column is equilibrated to 30° C. and the autosampler is set to 5° C. The mobile phases, 20 mM sodium phosphate monobasic at a pH of 2.0 (mobile phase A) and acetonitrile (mobile phase B) are used in a gradient elution from a ratio of 59:41 (A:B) to 5:95 (A:B), over the course of a 19.5 minute run time. Detection is by UV at 258 nm and the injection volume is 10 µL. Itraconazole content in powders are quantified relative to a standard curve.

Identification of known impurities A, B, C, D, E, F and G (shown in monograph Ph. Eur. 01/2011:1335) is confirmed by comparing the retention time of the impurity peaks in the PUR1900 samples to that of the itraconazole USP impurity mix reference standard spiked with impurity A. Unknown impurities are identified and quantified by relative retention time to that of the itraconazole main peak and with area above the limit of detection (LOD). All impurities are measured by area percent, with respect to the itraconazole peak.

Particle Size Reduction. The particle size distribution of the crystalline active agent can be modulated using a number of techniques familiar to those of skill in the art, including but not limited to, high-pressure homogenization, high-shear homogenization, jet-milling, pin milling, microfluidization, or wet milling (also known as ball milling, pearl milling or bead milling). Wet milling is often preferred, as it is able to achieve a wide range of particle size distributions, including those in the nanometer (<1 µm) size domain.

Particle Size Reduction Using Low Energy Wet Milling. One technique for reducing the particle size of the active agent was via low energy wet milling, (also known as roller milling, or jar milling). Suspensions of the active agent were prepared in an anti-solvent, which can be water, or any solvent in which the active agent is not appreciably soluble. Stabilizers, which can be, but are not limited to, non-ionic surfactants or amphiphilic polymers, are then added to the suspension along with milling media, which can be, but are not limited to, spherical with high wear resistance and in the size range from 0.03 to 0.70 millimeters in diameter. The vessels containing the suspensions are then rotated using a jar mill (US Stoneware, East Palestine, Ohio USA) while taking samples periodically to assess particle size (LA-950, HORIBA, Kyoto, Japan). When the particle size is sufficiently reduced, or when a particle size minimum is reached, the suspension is strained through a sieve to remove the milling media, and the product recovered.

Particle Size Reduction Using High Energy Wet Milling. Another technique for reducing the particle size of the active agent was via high-energy wet milling using a rotor-stator, or agitated media mill. Suspensions of the active agent were prepared in an anti-solvent, which can be water, or any solvent in which the active agent is not appreciably soluble. Stabilizers, which can be, but are not limited to, non-ionic surfactants or amphiphilic polymers, are then added to the suspension along with milling media, which can be, but are not limited to, spherical with high wear resistance and in the size range from 0.03 to 0.70 millimeters in diameter. The suspensions are then charged into the mill, which can be operated in either batch or recirculation mode. The process consists of the suspension and milling media being agitated within the milling chamber, which increases the energy input to the system and accelerates the particle size reduction process. The milling chamber and recirculation vessel are jacketed and actively cooled to avoid temperature increases in the product. The agitation rate and recirculation rate of the suspension are controlled during the process. Samples are taken periodically to assess particle size (LA-950, HORIBA, Kyoto, Japan). When the particle size is sufficiently reduced, or when a particle size minimum is reached, the suspension is discharged from the mill.

Particle Size Reduction using Microfluidization. Another technique for reducing the particle size distribution of the active agent was via Microfluidization. Microfluidizer-based processing is a high-shear wet-processing unit operation utilized for particle size reduction of liquids and solids. The unit can be configured with various interaction chambers, which are cylindrical modules with specific orifice and channel designs through which fluid is passed at high pressures to control shear rates. Product enters the unit via the inlet reservoir and is forced into the fixed-geometry interaction chamber at speeds up to 400 msec by a high-pressure pump. It is then effectively cooled, if required, and collected in the output reservoir. The process can be repeated as necessary (e.g. multiple "passes") to achieve the particle size targets. Particle size of the active agent is monitored periodically via laser diffraction (LA-950, HORIBA, Kyoto, Japan). When the particle size is sufficiently reduced, or when a particle size minimum is reached, the suspension is recovered from the unit.

Particle Size Reduction Using Jet Milling Another technique for reducing the particle size distribution of the active agent was via jet milling. Jet mills utilize fluid energy (compressed air or gas) to grind and classify, in a single chamber with no moving parts. Activated by high pressure air, the particles are accelerated into a high speed rotation in a shallow grinding chamber. As the particles impact on one another their size is reduced. Centrifugal force holds larger particles in the grinding rotation area until they have achieved the desired fine particle size. Centripetal force drags the desired particles towards the static classifier where they are allowed to exit upon achieving the correct particle size. The final particle size is controlled by varying the rate of the feed and propellant pressure.

Liquid Feedstock Preparation for Spray Drying. Spray drying homogenous particles requires that the ingredients of interest be solubilized in solution or suspended in a uniform and stable suspension. The feedstock can utilize water, or a combination of water and other miscible solvents such as alcohols or ketones, as the solvent in the case of solutions, or as the continuous phase in the case of suspensions. Feedstocks of the various formulations were prepared by dissolving the soluble components in the desired solvent(s) followed by dispersing the surfactant-stabilized active agent-containing suspension in the resulting solution while mixing, although the process is not limited to this specific order of operations.

Spray Drying Using Niro Spray Dryer. Dry powders were produced by spray drying utilizing a Niro Mobile Minor spray dryer (GEA Process Engineering Inc., Columbia, Md.) with powder collection from a cyclone, a product filter or both. Atomization of the liquid feed was performed using a co-current two-fluid nozzle either from Niro (GEA Process Engineering Inc., Columbia, Md.) or a Spraying Systems (Carol Stream, Ill.) ¼J two-fluid nozzle with gas cap 67147 and fluid cap 2850SS, although other two-fluid nozzle setups are also possible. In some embodiments, the two-fluid nozzle can be in an internal mixing setup or an external mixing setup. Additional atomization techniques include rotary atomization or a pressure nozzle. The liquid feed was fed using gear pumps (Cole-Parmer Instrument Company, Vernon Hills, Ill.) directly into the two-fluid nozzle or into a static mixer (Charles Ross & Son Company, Hauppauge, N.Y.) immediately before introduction into the two-fluid nozzle. An additional liquid feed technique includes feeding from a pressurized vessel. Nitrogen or air may be used as the drying gas, provided that moisture in the air is at least partially removed before its use. Pressurized nitrogen or air can be used as the atomization gas feed to the two-fluid nozzle. The drying gas inlet temperature can range from 70° C. to 300° C. and outlet temperature from 30° C. to 120° C. with a liquid feedstock rate of 10 mL/min to 100 mL/min. The gas supplying the two-fluid atomizer can vary depending on nozzle selection and for the Niro co-current two-fluid nozzle can range from 5 kg/hr to 50 kg/hr or for the Spraying Systems ¼J two-fluid nozzle can range from 30 g/min to 150 g/min. The atomization gas rate can be set to achieve a certain gas to liquid mass ratio, which directly affects the droplet size created. The pressure inside the drying drum can range from +3"WC to −6"WC. Spray dried powders can be collected in a container at the outlet of the cyclone, onto a cartridge or baghouse filter, or from both a cyclone and a cartridge or baghouse filter.

Spray Drying Using Büchi Spray Dryer. Dry powders were prepared by spray drying on a Büchi B-290 Mini Spray Dryer (BÜCHI Labortechnik AG, Flawil, Switzerland) with powder collection from either a standard or High Performance cyclone. The system was run either with air or nitrogen as the drying and atomization gas in open-loop (single pass) mode. When run using air, the system used the Büchi B-296 dehumidifier to ensure stable temperature and humidity of the air used to spray dry. Furthermore, when the relative humidity in the room exceeded 30% RH, an external LG dehumidifier (model 49007903, LG Electronics, Englewood Cliffs, N.J.) was run constantly. When run using nitrogen, a pressurized source of nitrogen was used. Furthermore, the aspirator of the system was adjusted to maintain the system pressure at −2.0" water column. Atomization of the liquid feed utilized a Büchi two-fluid nozzle with a 1.5 mm diameter or a Schlick 970-0 atomizer with a 0.5 mm liquid insert (Düsen-Schlick GmbH, Coburg, Germany). Inlet temperature of the process gas can range from 100° C. to 220° C. and outlet temperature from 30° C. to 120° C. with a liquid feedstock flowrate of 3 mL/min to 10 mL/min. The two-fluid atomizing gas ranges from 25 mm to 45 mm (300 LPH to 530 LPH) for the Büchi two-fluid nozzle and for the Schlick atomizer an atomizing air pressure of upwards of 0.3 bar. The aspirator rate ranges from 50% to 100%.

Stability Assessment: The physicochemical stability and aerosol performance of select formulations were assessed at 2-8° C., 25° C./60% RH, and when material quantities permitted, 40° C./75% RH as detailed in the International Conference on Harmonisation (ICH) Q1 guidance. Stability samples were stored in calibrated chambers (Darwin Chambers Company Models PH024 and PH074, St. Louis. Mo.). Bulk powder samples were weighed into amber glass vials, sealed under 30% RH, and induction-sealed in aluminum pouches (Drishield 3000, 3M, St. Paul, Minn.) with silica desiccant (2.0 g, Multisorb Technologies, Buffalo, N.Y.). Additionally, to assess the stability of the formulations in capsules, the target mass of powder was weighed by hand into a size 3, HPMC capsule (Capsugel Vcaps, Peapack, N.J.)) with a +/−0.2 mg tolerance at 30% RH. Filled capsules were then aliquoted into high-density polyethylene (HDPE) bottles and induction sealed in aluminum pouches with silica desiccant.

Example 1. Dry Powder Formulations of Polysorbate 80-Stabilized Nanocrystalline Itraconazole Containing Sodium Sulfate/Mannitol A. Powder Preparation.

The nanocrystalline itraconazole was prepared by compounding 11.662 g of itraconazole (Neuland lot ITI0114005) in 103.789 g of water and 1.1662 g of polysorbate 80 (Spectrum lot 2DI0112). 129.625 g of 500 µm polystyrene milling media (Dow Chemical, Midland Mich.) was then added to the suspension, and the suspension was milled at 1000 rpm for one hour then 1500 rpm for 30 minutes before being collected. The final median particle size (Dv(50)) of the milled suspension was 124 nm.

Feedstock solutions were prepared and used to manufacture dry powders composed of nanocrystalline itraconazole, polysorbate 80 and other additional excipients. Drug loads of 20 wt % and 50 wt % itraconazole, on a dry basis, were targeted. The feedstock solutions that were used to spray dry particles were made as follows. The required quantity of water was weighed into a suitably sized glass vessel. The excipients were added to the water and the solution allowed to stir until visually clear. The itraconazole-containing suspension was then added to the excipient solution and stirred until visually homogenous. The feedstocks were then spray-dried. Feedstocks were stirred while spray dried. Feedstock masses were 83.3 g, which supported manufacturing campaigns of 15 minutes. Table 2 lists the components of the feedstocks used in preparation of the dry powders.

TABLE 2

Feedstock compositions and Dry Powder Composition (w/w), dry basis

| Formulation | Water (g) | Itraconazole (g) | Polysorbate 80 | Sodium sulfate (g) | Mannitol (g) | Total mass (gm) |
|---|---|---|---|---|---|---|
| I | 80.8450 | 0.50027 | 0.05002 | 0.9782 | 0.9783 | 83.3543 |
| II | 80.8375 | 1.24973 | 0.12497 | 0.5672 | 0.5643 | 83.3413 |

Dry powders of Formulations I and II were manufactured from these feedstocks by spray drying on the Büchi B-290 Mini Spray Dryer (BÜCHI Labortechnik AG, Flawil, Switzerland) with cyclone powder collection. The system was run in open-loop (single pass) mode using nitrogen as the drying and atomization gas. Atomization of the liquid feed utilized a Büchi nozzle with 1.5 mm cap and 0.7 liquid tip. The aspirator of the system was adjusted to maintain the system pressure at −2.0" water column.

The following spray drying conditions were followed to manufacture the dry powders. For Formulations I and II, the liquid feedstock solids concentration was 3.0 wt %, the process gas inlet temperature was 117° C. to 119° C., the process gas outlet temperature was 50° C., the drying gas flowrate was 17.0 kg/hr, the atomization gas flowrate was 30.4 g/min, the atomization gas, and the liquid feedstock flowrate was 6.0 mL/min. The resulting dry powder formulations are reported in Table 3 below.

TABLE 3

Dry Powder composition

| Formulation | Dry Powder Composition (w/w), dry basis |
|---|---|
| I | 20% itraconazole, 39% sodium sulfate, 39% mannitol, 2% polysorbate 80 |

TABLE 3-continued

Dry Powder composition

| Formulation | Dry Powder Composition (w/w), dry basis |
|---|---|
| II | 50% itraconazole, 22.5% sodium sulfate, 22.5% mannitol, 5% polysorbate 80 |

B. Powder Characterization.

The bulk particle size characteristics for the two formulations are found in Table 4. The span at 1 bar of 1.83 and 1.67 for Formulations I and II, respectively, indicates a relatively narrow size distribution. The 1 bar/4 bar dispersibility ratio of 1.07 and 1.12 for Formulations I and II respectively, indicate that they are relatively independent of dispersion energy, a desirable characteristic which allows similar particle dispersion across a range of dispersion energies.

TABLE 4

Bulk particle size

| Formulation | 0.5 bar | | 1 bar | | 4 bar | | 1 bar:4 bar |
|---|---|---|---|---|---|---|---|
| | Dv[50] (µm) | Span | Dv[50] (µm) | Span | Dv[50] (µm) | Span | Dv[50] ratio |
| I | 2.28 | 1.65 | 1.89 | 1.83 | 1.77 | 1.93 | 1.07 |
| II | 2.42 | 1.64 | 2.05 | 1.67 | 1.84 | 1.83 | 1.12 |

The geometric particle size and capsule emitted powder mass (CEPM) measured and/or calculated at 60 liters per minute (LPM) and 20 LPM simulated patient flow rates were measured for the two formulations and reported in Table 5. The small changes in CEPM and geometric size from 60 LPM to 20 LPM indicates that the dry powder formulations are relatively independent of patient inspiratory flowrate, indicating that patients breathing in at varying flow rates would receive a relatively similar therapeutic dose.

TABLE 5

Emitted particle size

| | 20 LPM | | 60 LPM | |
|---|---|---|---|---|
| Formulation | CEPM (%) | Dv[50] (µm) | CEPM (%) | Dv[50] (µm) |
| I | 89.6 | 4.62 | 100.4 | 2.46 |
| II | 42.5 | 8.82 | 97.4 | 2.31 |

The aerodynamic particle size, fine particle fractions and fine particle doses measured and/or calculated with an eight-stage Anderson Cascade Impactor (ACI-8) are reported in Table 6. The fine particle dose for Formulations I and II both indicate a high percentage of the nominal dose which is filled into the capsule reaches the impactor stages (38.8% and 37.1%, respectively) and so would be predicted to be delivered to the lungs. The MMAD of Formulations I and II were 3.59 microns and 3.17 microns, respectively, indicating deposition in the central and conducting airways.

TABLE 6

Aerodynamic particle size

| Formulation | MMAD (μm) | FPD < 5 μm (% nominal dose) |
|---|---|---|
| I | 3.59 | 38.8 |
| II | 3.17 | 37.1 |

The weight loss of Formulations I and II were measured via TGA and were found to be 0.48% and 0.15%, respectively.

The itraconazole content of Formulations I and II were measured with HPLC-UV and are 102.9% and 103.1%, respectively.

The crystallinity of Formulations I and II were assessed via XRD. The diffraction pattern of itraconazole is observed in both formulations, suggesting the milling or spray drying process does not affect the solid-state of itraconazole. Additional peaks observed in the patterns correspond to the additional excipients in the formulations. (FIG. 1)

Formulations I and II were determined to be stable after being stored for six months at 2-8° C. and 25° C./60% RH.

Example 2. Dry Powder Formulations of Polysorbate 80-Stabilized Nanocrystalline Itraconazole Containing Sodium Chloride/Leucine A. Powder Preparation.

The nanocrystalline itraconazole was prepared by compounding 11.662 g of itraconazole (Neuland lot ITI0114005) in 103.789 g of water and 1.1662 g of polysorbate 80 (Spectrum lot 2DI0112). 129.625 g of 500 μm polystyrene milling media (Dow Chemical, Midland Mich.) was then added to the suspension, and the suspension was milled at 1000 rpm for one hour then 1500 rpm for 30 minutes before being collected. The final median particle size (Dv(50)) of the milled suspension was 124 nm.

Feedstock solutions were prepared and used to manufacture dry powders composed of nanocrystalline itraconazole, polysorbate 80 and other additional excipients. Drug loads of 20 wt % and 50 wt % itraconazole, on a dry basis, were targeted. The feedstock solutions that were used to spray dry particles were made as follows. The required quantity of water was weighed into a suitably sized glass vessel. The excipients were added to the water and the solution allowed to stir until visually clear. The itraconazole-containing suspension was then added to the excipient solution and stirred until visually homogenous. The feedstocks were then spray-dried. Feedstocks were stirred while spray dried. Feedstock masses were 83.3 g, which supported manufacturing campaigns of 15 minutes. Table 7 lists the components of the feedstocks used in preparation of the dry powders.

TABLE 7

Feedstock compositions

| Formulation | Water (g) | Itraconazole (g) | Polysorbate 80 (g) | Sodium chloride (g) | Leucine (g) | Total mass (gm) |
|---|---|---|---|---|---|---|
| III | 80.806043 | 0.49887 | 0.0489887 | 1.5548 | 0.3881 | 83.2977 |
| IV | 80.829235 | 1.24915 | 0.124915 | 0.8956 | 0.2210 | 83.3199 |

Dry powders of Formulations I and II were manufactured from these feedstocks by spray drying on the Büchi B-290 Mini Spray Dryer (BÜCHI Labortechnik AG, Flawil, Switzerland) with cyclone powder collection. The system was run in open-loop (single pass) mode using nitrogen as the drying and atomization gas. Atomization of the liquid feed utilized a Büchi nozzle with 1.5 mm cap and 0.7 liquid tip. The aspirator of the system was adjusted to maintain the system pressure at −2.0" water column.

The following spray drying conditions were followed to manufacture the dry powders. For Formulations I and II, the liquid feedstock solids concentration was 3.0%, the process gas inlet temperature was 138° C. to 141° C., the process gas outlet temperature was 60° C., the drying gas flowrate was 17.0 kg/hr, the atomization gas flowrate was 30.4 g/min, the atomization gas, and the liquid feedstock flowrate was 6.0 mL/min. The resulting dry powder formulations are reported in Table 8.

TABLE 8

Dry powder compositions, dry basis

| Formulation | Dry Powder Composition (w/w), dry basis |
|---|---|
| III | 20% itraconazole, 62.4% sodium chloride, 15.6% leucine, 2% polysorbate 80 |
| IV | 50% itraconazole, 36% sodium chloride, 9% leucine, 5% polysorbate 80 |

B. Powder Characterization.

The bulk particle size characteristics for the two formulations are found in Table 9. The span at 1 bar of 1.76 and 1.86 for Formulations III and IV, respectively, indicates a relatively narrow size distribution. The 1 bar/4 bar dispersibility ratio of 1.19 and 1.05 for Formulations III and IV respectively, indicate that they are relatively independent of dispersion energy, a desirable characteristic which allows similar particle dispersion across a range of dispersion energies.

TABLE 9

Bulk particle size

| Formulation | 0.5 bar | | 1 bar | | 4 bar | | 1 bar:4 bar |
|---|---|---|---|---|---|---|---|
| | Dv[50] (μm) | Span | Dv[50] (μm) | Span | Dv[50] (μm) | Span | Dv[50] ratio |
| III | 2.13 | 1.81 | 1.94 | 1.76 | 1.63 | 1.67 | 1.19 |
| IV | 2.07 | 1.81 | 1.93 | 1.86 | 1.85 | 1.81 | 1.05 |

The geometric particle size and capsule emitted powder mass (CEPM) measured and/or calculated at 60 liters per minute (LPM) and 20 LPM simulated patient flow rates were measured for the two formulations and reported in Table 10. The small changes in CEPM and geometric size from 60 LPM to 20 LPM indicates that the dry powder formulations are relatively independent of patient inspiratory flowrate, indicating that patients breathing in at varying flow rates would receive a relatively similar therapeutic dose.

TABLE 10

| | Emitted particle size | | | |
|---|---|---|---|---|
| | 20 LPM | | 60 LPM | |
| Formulation | CEPM (%) | Dv[50] (μm) | CEPM (%) | Dv[50] (μm) |
| III | 98.5 | 3.77 | 99.5 | 2.10 |
| IV | 60.6 | 4.75 | 100.1 | 2.31 |

The aerodynamic particle size, fine particle fractions and fine particle doses measured and/or calculated with an eight-stage Anderson Cascade Impactor (ACI-8) are reported in Table 11. The fine particle dose for Formulation III and IV both indicate a high percentage of the nominal dose which is filled into the capsule reaches the impactor stages (55.5% and 49.4%, respectively) and so would be predicted to be delivered to the lungs. The MMAD of Formulation III and IV were 3.14 microns and 3.30 microns, respectively, indicating deposition in the central and conducting airways.

TABLE 11

| | Aerodynamic particle size | |
|---|---|---|
| Formulation | MMAD (μm) | FPD < 5 μm (% nominal dose) |
| III | 3.14 | 55.5 |
| IV | 3.30 | 49.4 |

The weight loss of Formulations III and IV were measured via TGA and were found to be 0.15% and 0.08%, respectively.

The itraconazole content of Formulations III and IV were measured with HPLC-UV and are 103.7% and 104.9%, respectively.

Figure 2:
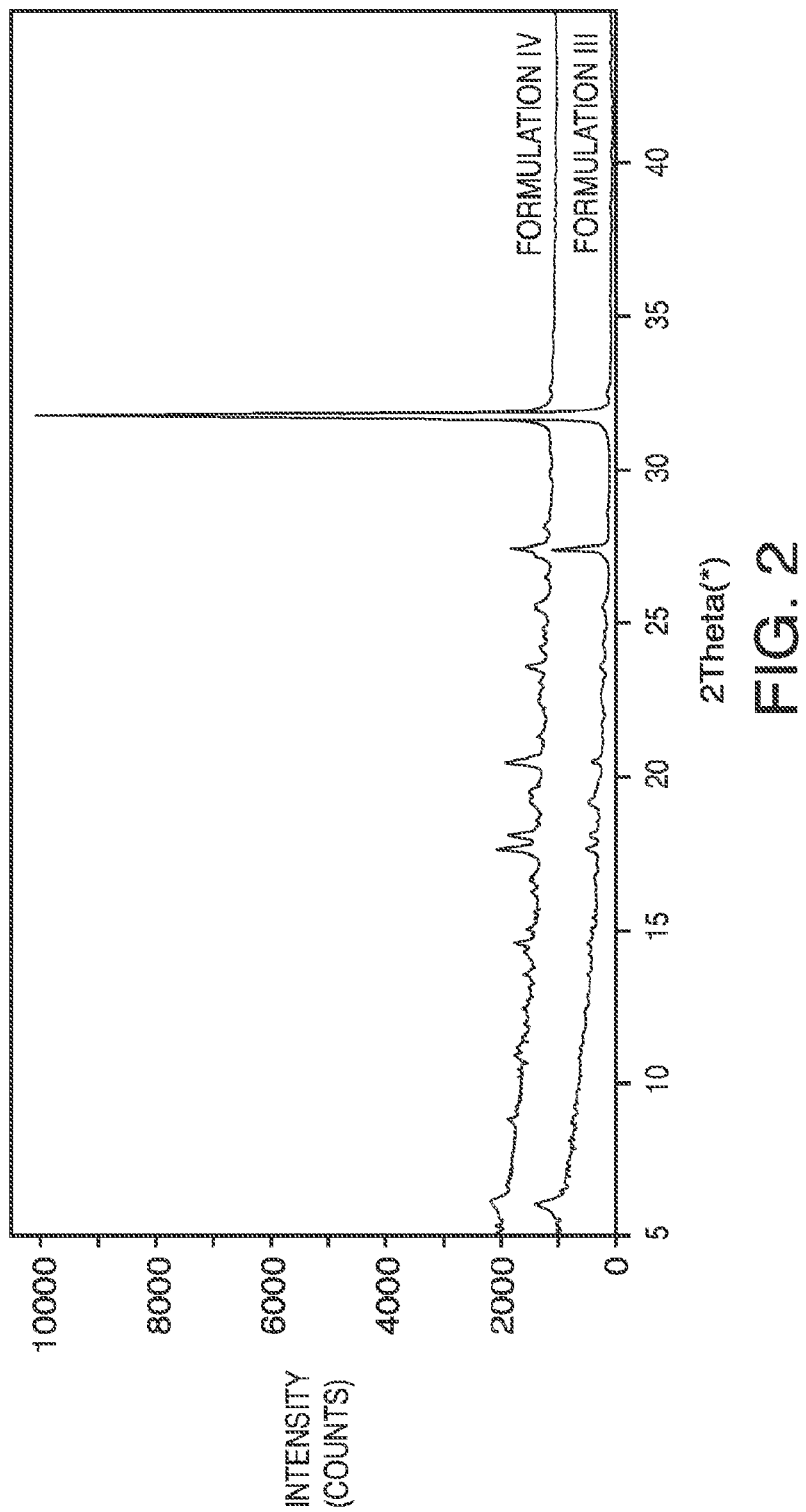
FIG. 2: Particle X-Ray Diffraction plot for Formulations III and IV.

The crystallinity of Formulations III and IV were assessed via XRD. The diffraction pattern of itraconazole is observed in both formulations, suggesting the milling or spray drying process does not affect the solid-state of itraconazole. Additional peaks observed in the patterns correspond to the additional excipients in the formulations. (FIG. 2)

Formulations III and IV were determined to be stable after being stored for six months at 2-8° C. and 25° C./60% RH.

Example 3. Dry Powder Formulations of Polysorbate 80-Stabilized Nanocrystalline Itraconazole Containing Magnesium Lactate/Leucine A. Powder Preparation.

The nanocrystalline itraconazole was prepared by compounding 11.662 g of itraconazole (Neuland lot ITI0114005) in 103.789 g of water and 1.1662 g of polysorbate 80 (Spectrum lot 2DI0112). 129.625 g of 500 μm polystyrene milling media (Dow Chemical, Midland Mich.) was then added to the suspension, and the suspension was milled at 1000 rpm for one hour then 1500 rpm for 30 minutes before being collected. The final median particle size (Dv(50)) of the milled suspension was 124 nm.

Feedstock solutions were prepared and used to manufacture dry powders composed of nanocrystalline itraconazole, polysorbate 80 and other additional excipients. Drug loads of 20 wt % and 50 wt % itraconazole, on a dry basis, were targeted. The feedstock solutions that were used to spray dry particles were made as follows. The required quantity of water was weighed into a suitably sized glass vessel. The excipients were added to the water and the solution allowed to stir until visually clear. The itraconazole-containing suspension was then added to the excipient solution and stirred until visually homogenous. The feedstocks were then spray-dried. Feedstocks were stirred while spray dried. Feedstock masses were 83.3 g, which supported manufacturing campaigns of 15 minutes. Table 12 lists the components of the feedstocks used in preparation of the dry powders.

TABLE 12

| | Feedstock compositions | | | | | |
|---|---|---|---|---|---|---|
| Formulation | Water (g) | Itraconazole (g) | Polysorbate 80 (g) | Magnesium lactate (g) | Leucine (g) | Total mass (gm) |
| V | 80.83964 | 0.5006 | 0.05006 | 2.1096 | 0.2923 | 83.7922 |
| VI | 80.83467 | 1.25021 | 0.125021 | 1.2177 | 0.1718 | 83.5994 |

Dry powders of Formulations V and VI were manufactured from these feedstocks by spray drying on the Büchi B-290 Mini Spray Dryer (BÜCHI Labortechnik AG, Flawil, Switzerland) with cyclone powder collection. The system was run in open-loop (single pass) mode using nitrogen as the drying and atomization gas. Atomization of the liquid feed utilized a Büchi nozzle with 1.5 mm cap and 0.7 liquid tip. The aspirator of the system was adjusted to maintain the system pressure at −2.0" water column.

The following spray drying conditions were followed to manufacture the dry powders. For Formulations V and VI, the liquid feedstock solids concentration was 3.0%, the process gas inlet temperature was 171° C. to 173° C., the process gas outlet temperature was 80° C., the drying gas flowrate was 17.0 kg/hr, the atomization gas flowrate was 30.4 g/min, the atomization gas, and the liquid feedstock flowrate was 6.0 mL/min. The resulting dry powder formulations are reported in Table 13.

TABLE 13

| Dry powder compositions, dry basis | |
|---|---|
| Formulation | Dry Powder Composition (w/w), dry basis |
| V | 20% itraconazole, 66.3% magnesium lactate, 11.7% leucine, 2% polysorbate 80 |
| VI | 50% itraconazole, 38.25% magnesium lactate, 6.75% leucine, 5% polysorbate 80 |

B. Powder Characterization.

The bulk particle size characteristics for the two formulations are found in Table 14. The span at 1 bar of 1.70 and 1.83 for Formulations V and VI, respectively, indicates a relatively narrow size distribution. The 1 bar/4 bar dispersibility ratio of 1.02 and 1.05 for Formulations V and VI respectively, indicate that they are relatively independent of dispersion energy, a desirable characteristic which allows similar particle dispersion across a range of dispersion energies.

TABLE 14

Bulk particle size

| For-mu-lation | 0.5 bar Dv[50] (μm) | Span | 1 bar Dv[50] (μm) | Span | 4 bar Dv[50] (μm) | Span | 1 bar:4 bar Dv[50] ratio |
|---|---|---|---|---|---|---|---|
| V | 2.75 | 1.64 | 2.60 | 1.70 | 2.55 | 1.67 | 1.02 |
| VI | 2.36 | 1.76 | 2.14 | 1.83 | 2.04 | 1.88 | 1.05 |

The geometric particle size and capsule emitted powder mass (CEPM) measured and/or calculated at 60 liters per minute (LPM) and 20 LPM simulated patient flow rates were measured for the two formulations and reported in Table 15. The small changes in CEPM and geometric size from 60 LPM to 20 LPM indicates that the dry powder formulations are relatively independent of patient inspiratory flowrate, indicating that patients breathing in at varying flow rates would receive a relatively similar therapeutic dose.

TABLE 15

Emitted particle size

| | 20 LPM | | 60 LPM | |
|---|---|---|---|---|
| Formulation | CEPM (%) | Dv[50] (μm) | CEPM (%) | Dv[50] (μm) |
| V | 95.2 | 5.21 | 98.5 | 2.77 |
| VI | 93.5 | 3.93 | 98.1 | 2.34 |

The aerodynamic particle size, fine particle fractions and fine particle doses measured and/or calculated with an eight-stage Anderson Cascade Impactor (ACI-8) are reported in Table 16. The fine particle dose for Formulations V and VI both indicate a high percentage of the nominal dose which is filled into the capsule reaches the impactor stages (39.6% and 44.6%, respectively) and so would be predicted to be delivered to the lungs. The MMAD of Formulations V and VI were 3.97 microns and 3.42 microns, respectively, indicating deposition in the central and conducting airways.

TABLE 16

Aerodynamic particle size

| Formulation | MMAD (μm) | FPD < 5 μm (% nominal dose) |
|---|---|---|
| V | 3.97 | 39.6 |
| VI | 3.42 | 44.6 |

The weight loss of Formulations V and VI were measured via TGA and were found to be 5.157% and 3.087%, respectively.

The itraconazole content of Formulations V and VI were measured with HPLC-UV and are 99.7% and 100.6%, respectively.

Figure 3:
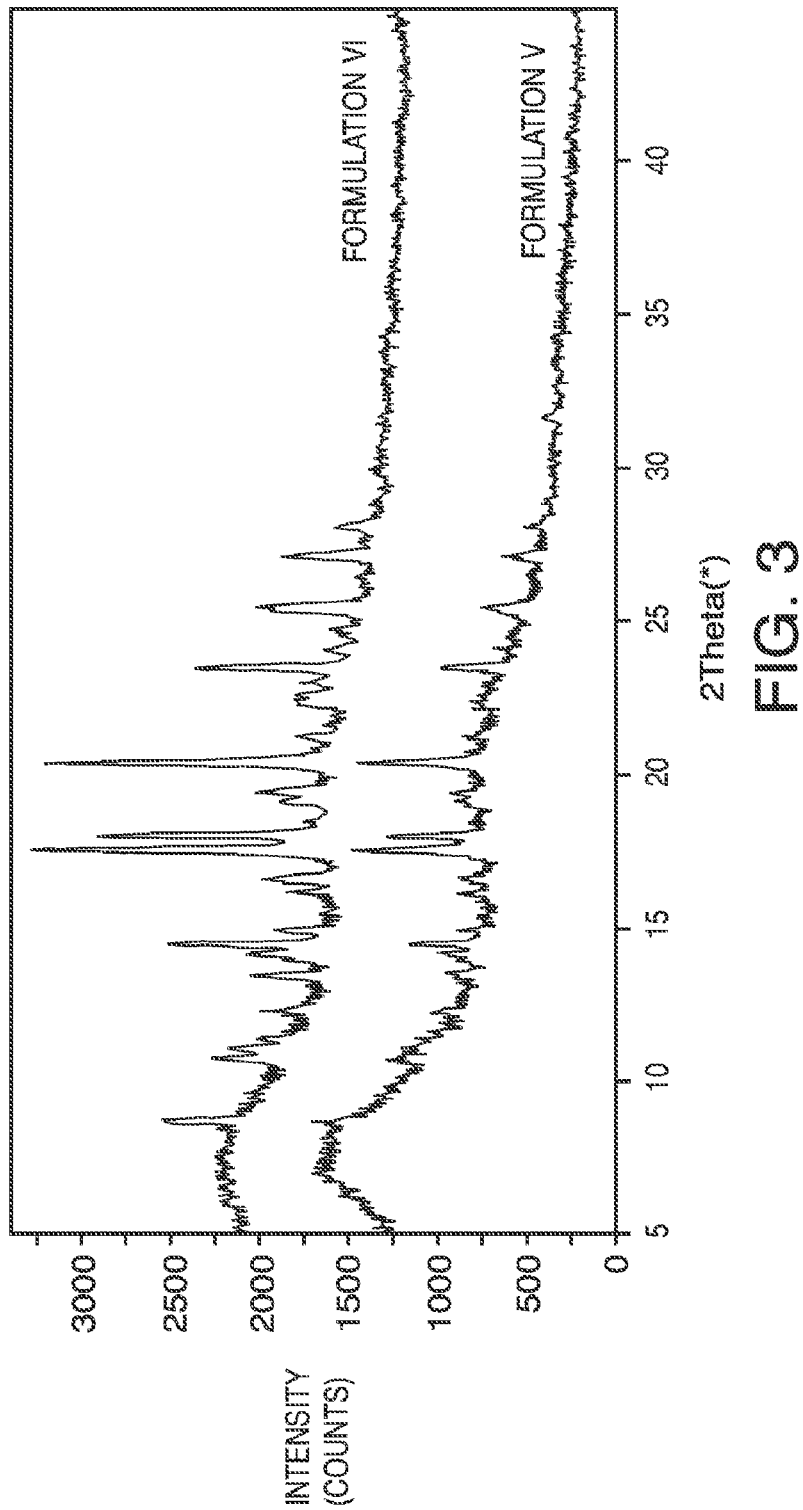
FIG. 3: Particle X-Ray Diffraction plot for Formulations V and VI.

The crystallinity of Formulations V and VI were assessed via XRD. The diffraction pattern of itraconazole is observed in both formulations, suggesting the milling or spray drying process does not affect the solid-state of itraconazole. Additional peaks observed in the patterns correspond to the additional excipients in the formulations. (FIG. 3)

Formulations V and VI were determined to be stable after being stored for six months at 2-8° C. and 25° C./60% RH.

Example 4. Dry Powder Formulations of Oleic Acid-Stabilized Nanocrystalline Itraconazole Containing Sodium Sulfate/Leucine A. Powder Preparation.

The nanocrystalline itraconazole was prepared by compounding 11.646 g of itraconazole (Neuland lot ITI0114005) in 104.233 g of water, 0.582 g of oleic acid (Croda 000705097), and 9.44 g of 10% ammonium hydroxide. 129.625 g of 500 μm polystyrene milling media (Dow Chemical, Midland Mich.) was then added to the suspension, and the suspension was milled at 1000 rpm for one hour and then 1500 rpm for an additional hour before being collected. The final median particle size (Dv(50)) of the milled suspension was 120 nm.

Feedstock solutions were prepared and used to manufacture dry powders composed of nanocrystalline itraconazole, oleic acid and other additional excipients. Drug loads of 50 wt % and 70 wt % itraconazole, on a dry basis, were targeted. The feedstock solutions that were used to spray dry particles were made as follows. The required quantity of water was weighed into a suitably sized glass vessel. The excipients were added to the water and the solution allowed to stir until visually clear. The itraconazole-containing suspension was then added to the excipient solution and stirred until visually homogenous. The feedstocks were then spray-dried. The feedstocks were stirred while spray dried. Feedstock volumes ranged from 100 to 193.3 g, which supported manufacturing campaigns from 16 to 34 minutes. Table 17 lists the components of the feedstocks used in preparation of the dry powders.

TABLE 17

Feedstock compositions

| For-mu-lation | Wa-ter (g) | Itracon-azole (g) | Oleic acid (g) | So-dium sulfate (g) | Leu-cine (g) | Ammo-nium hy-droxide (g) | Total mass (gm) |
|---|---|---|---|---|---|---|---|
| VII | VII | 187.5173 | 2.6775 | 0.1338 | 1.9288 | 0.8267 | 0.2170 |
| VIII | VIII | 96.98351 | 1.93610 | 0.0968 | 0.3988 | 0.3971 | 0.1569 |

Dry powders of Formulations VII and VIII were manufactured from these feedstocks by spray drying on the Büchi B-290 Mini Spray Dryer (BÜCHI Labortechnik AG, Flawil, Switzerland) with cyclone powder collection. The system was run in open-loop (single pass) mode using nitrogen as the drying and atomization gas. Atomization of the liquid feed utilized a Büchi nozzle with 1.5 mm cap and 0.7 liquid tip. The aspirator of the system was adjusted to maintain the system pressure at −2.0″ water column.

The following spray drying conditions were followed to manufacture the dry powders. For Formulations VII and VIII, the liquid feedstock solids concentration was 3.0%, the process gas inlet temperature was 131° C. to 133° C., the process gas outlet temperature was 60° C., the drying gas flowrate was 17.0 kg/hr, the atomization gas flowrate was 30.4 g/min (1.824 kg/hr), and the liquid feedstock flowrate was 6.0 mL/min. The resulting dry powder formulations are reported in Table 18.

TABLE 18

| Formulation | Dry powder compositions, dry basis |
|---|---|
| | Dry Powder Composition (w/w), dry basis |
| VII | 50% itraconazole, 33.25% sodium sulfate, 14.25% leucine, 2.5% oleic acid |
| VIII | 70% itraconazole, 13.25% sodium sulfate, 13.25% leucine, 3.5% oleic acid |

B. Powder Characterization.

The bulk particle size characteristics for the two formulations are found in Table 19. The span at 1 bar of 1.94 and 1.81 for Formulations VII and VIII, respectively, indicates a relatively narrow size distribution. The 1 bar/4 bar dispersibility ratio of 1.22 and 1.11 for Formulations VII and VIII respectively, indicate that they are relatively independent of dispersion energy, a desirable characteristic which allows similar particle dispersion across a range of dispersion energies.

TABLE 19

Bulk particle size

| Formulation | 0.5 bar | | 1 bar | | 4 bar | | 1 bar:4 bar |
|---|---|---|---|---|---|---|---|
| | Dv[50] (μm) | Span | Dv[50] (μm) | Span | Dv[50] (μm) | Span | Dv[50] ratio |
| VII | 2.44 | 1.88 | 2.22 | 1.94 | 1.81 | 1.91 | 1.22 |
| VIII | 2.77 | 1.72 | 2.50 | 1.81 | 2.26 | 1.96 | 1.11 |

The geometric particle size and capsule emitted powder mass (CEPM) measured and/or calculated at 60 liters per minute (LPM) and 20 LPM simulated patient flow rates were measured for the two formulations and reported in Table 20. The small changes in CEPM and geometric size from 60 LPM to 20 LPM indicates that the dry powder formulations are relatively independent of patient inspiratory flowrate, indicating that patients breathing in at varying flow rates would receive a relatively similar therapeutic dose.

TABLE 20

Emitted particle size

| Formulation | 20 LPM | | 60 LPM | |
|---|---|---|---|---|
| | CEPM (%) | Dv[50] (μm) | CEPM (%) | Dv[50] (μm) |
| VII | 97.2 | 3.08 | 97.6 | 2.36 |
| VIII | 95.6 | 3.21 | 98.2 | 2.68 |

The aerodynamic particle size, fine particle fractions and fine particle doses measured and/or calculated with an eight-stage Anderson Cascade Impactor (ACI-8) are reported in Table 21. The fine particle dose for Formulation VII and VIII both indicate a high percentage of the nominal dose which is filled into the capsule reaches the impactor stages (56.0% and 52.6%, respectively) and so would be predicted to be delivered to the lungs. The MMAD of Formulation VII and VIII were 2.77 microns and 3.08 microns, respectively, indicating deposition in the central and conducting airways.

TABLE 21

Aerodynamic particle size

| Formulation | MMAD (μm) | FPD < 5 μm (% nominal dose) |
|---|---|---|
| VII | 2.77 | 56.0 |
| VIII | 3.08 | 52.6 |

The weight loss of Formulations VII and VIII were measured via TGA and were found to be 0.47% and 0.33%, respectively.

The itraconazole content of Formulations VII and VIII were measured with HPLC-UV and are 101.5% and 101.4%, respectively.

Figure 4:
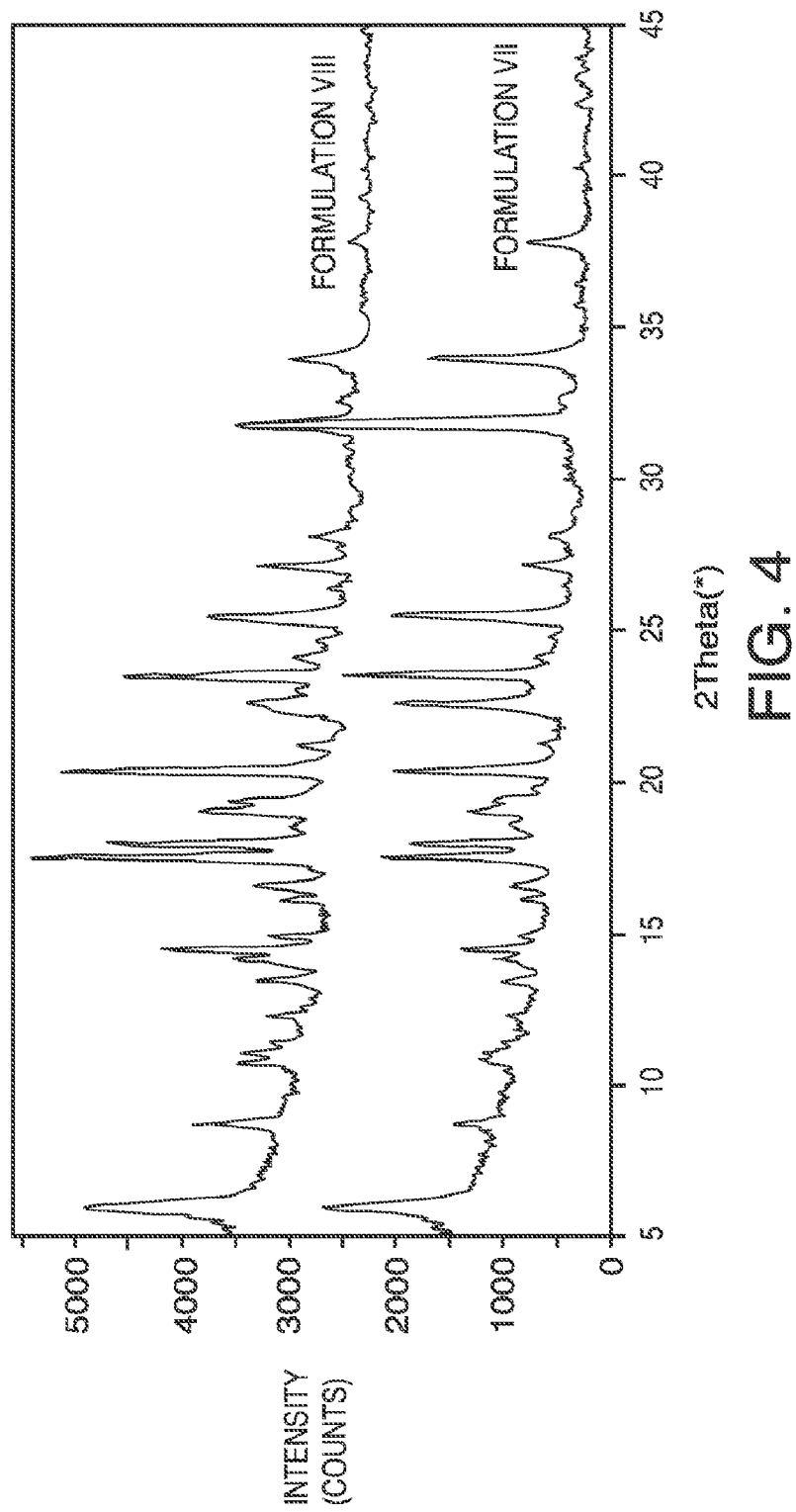
FIG. 4: Particle X-Ray Diffraction plot for Formulations VII and VIII.
Figure 5:
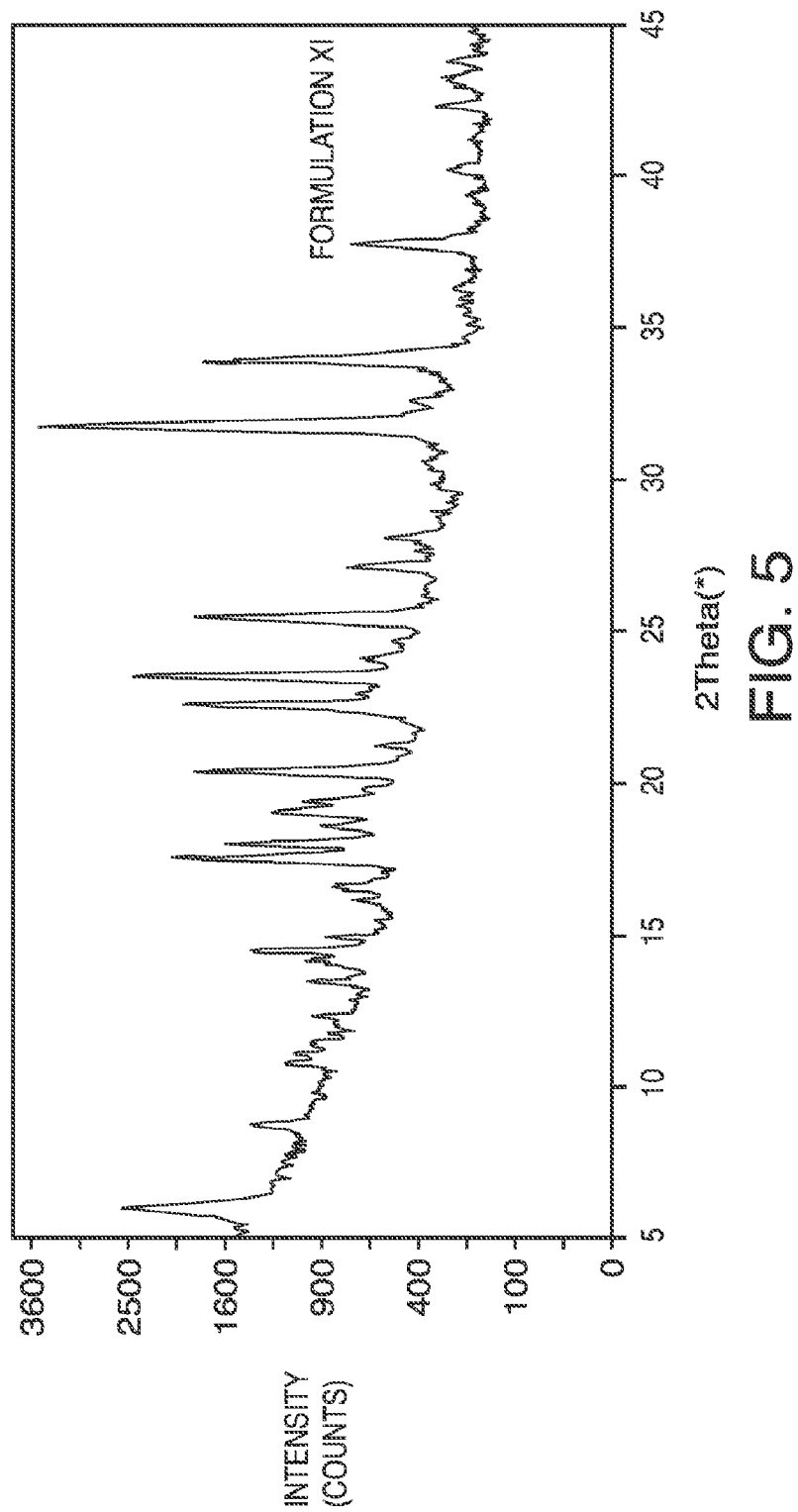
FIG. 5: Particle X-Ray Diffraction plot for Formulations XI.

The crystallinity of Formulations VII and VIII were assessed via XRD. The diffraction pattern of itraconazole is observed in both formulations, suggesting the milling or spray drying process does not affect the solid-state of itraconazole. Additional peaks observed in the patterns correspond to the additional excipients in the formulations. (FIG. 4)

Formulations VII and VIII were determined to be stable after being stored for six months at 2-8° C. and 25° C./60% RH.

Example 5. Reference Liquid Nanocrystalline and Microcrystalline Itraconazole Formulations Liquid formulations of crystalline particulate itraconazole were prepared.

Formulation IX is a micro-suspension of itraconazole with polysorbate 80. The itraconazole concentration in the liquid is 5 mg/mL. The ratio of itraconazole to polysorbate 80 is 10:1 (wgt/wgt). The median size of the itraconazole crystals is 1600 nanometers.

Formulation X is a nano-suspension of itraconazole with polysorbate 80. The itraconazole concentration in the liquid is 5 mg/mL. The ratio of itraconazole to polysorbate 80 is 10:1 (wgt/wgt). The median size of the itraconazole crystals is 132 nanometers.

Example 6. Dry Powder Formulation of Oleic Acid-Stabilized Nanocrystalline Itraconazole Containing Sodium Sulfate/Leucine A. Powder Preparation.

The nanocrystalline itraconazole was prepared by compounding 30.374 g of itraconazole (Neuland ITI0714011) in 87.018 g of water, 1.519 g of oleic acid (Croda 000705097), and 2.585 g ammonium hydroxide (Acros B0522464). 129.625 g of 500 μm polystyrene milling media (Dow Chemical, Midland Mich.) was then added to the suspension, and the suspension was milled at 1800 rpm for two hours before being collected. The final median particle size (Dv(50)) of the milled suspension was 124 nm.

A feedstock solution was prepared and used to manufacture a dry powder composed of nanocrystalline itraconazole, oleic acid and other additional excipients. A drug load of 50 wt % itraconazole, on a dry basis, was targeted. The feedstock solution that was used to spray dry particles were made as follows. The required quantity of water was weighed into a suitably sized glass vessel. The excipients were added to the water and the solution allowed to stir until visually clear. The itraconazole-containing suspension was then added to the excipient solution and stirred until visually homogenous. The feedstock was then spray-dried. Feedstock mass was 1219.4 g, which supported a manufacturing campaign of approximately 3.5 hours. Table 22 lists the components of the feedstock used in preparation of the dry powder.

TABLE 22

Feedstock composition

| Formulation | Water (g) | Itraconazole (g) | Oleic acid (g) | Sodium sulfate (g) | Leucine (g) | Ammonium hydroxide (g) | Total mass (gm) |
|---|---|---|---|---|---|---|---|
| XI | 1181.9273 | 18.3 | 0.915 | 12.8071 | 4.517 | 1.5577 | 1220.08 |

A dry powder of Formulation XI was manufactured from this feedstock by spray drying on the Büchi B-290 Mini Spray Dryer (BÜCHI Labortechnik AG, Flawil, Switzerland) with cyclone powder collection. The system was run in open-loop (single pass) mode using nitrogen as the drying and atomization gas. Atomization of the liquid feed utilized a Büchi nozzle with 1.5 mm cap and 0.7 liquid tip. The aspirator of the system was adjusted to maintain the system pressure at −2.0" water column.

The following spray drying conditions were followed to manufacture the dry powder. For Formulations XI, the liquid feedstock solids concentration was 3.0%, the process gas inlet temperature was 129° C. to 132° C., the process gas outlet temperature was 60° C., the drying gas flowrate was 17.0 kg/hr, the atomization gas flowrate was 30.4 g/min, and the liquid feedstock flowrate was 6.0 mL/min. The resulting dry powder formulation is reported in Table 23.

TABLE 23

Dry powder composition, dry basis

| Formulation | Dry Powder Composition (w/w), dry basis |
|---|---|
| XI | 50% itraconazole, 35% sodium sulfate, 12.5% leucine, 2.5% oleic acid |

B. Powder Characterization.

The bulk particle size characteristics for the formulation are found in Table 24. The span at 1 bar of 2.77 for Formulations XI, indicates a relatively narrow size distribution. The 1 bar/4 bar dispersibility ratio of 1.28 for Formulations XI, indicates the particle size is relatively independent of dispersion energy, a desirable characteristic which allows similar dispersion across a range of dispersion energies.

TABLE 24

Bulk particle size

| Formulation | 0.5 bar | | 1 bar | | 4 bar | | 1 bar:4 bar |
|---|---|---|---|---|---|---|---|
| | Dv[50] (µm) | Span | Dv[50] (µm) | Span | Dv[50] (µm) | Span | Dv[50] ratio |
| XI | 2.96 | 2.53 | 2.46 | 2.77 | 1.92 | 2.48 | 1.28 |

The geometric particle size and capsule emitted powder mass (CEPM) measured and/or calculated at 60 liters per minute (LPM) and 20 LPM simulated patient flow rates were measured for the formulation and reported in Table 25. The small changes in CEPM and geometric size from 60 LPM to 20 LPM indicates that the dry powder formulation is relatively independent of patient inspiratory flowrate, indicating that patients breathing in at varying flow rates would receive a relatively similar therapeutic dose.

TABLE 25

Emitted particle size

| Formulation | 20 LPM | | 60 LPM | |
|---|---|---|---|---|
| | CEPM (%) | Dv[50] (µm) | CEPM (%) | Dv[50] (µm) |
| XI | 98.6 | 4.37 | 99.1 | 3.62 |

The aerodynamic particle size, fine particle fractions and fine particle doses measured and/or calculated with a Next Generation Impactor (NGI) are reported in Table 26. The fine particle dose for Formulation XI indicates a high percentage of the nominal dose which is filled into the capsule reaches the impactor stages (42%) and so would be predicted to be delivered to the lungs. The MMAD of Formulation XI was 3.37 microns, indicating deposition in the central and conducting airways.

TABLE 26

| Aerodynamic particle size | | |
|---|---|---|
| Formulation | MMAD (μm) | FPD < 5 μm (% nominal dose) |
| XI | 3.37 | 42.0 |

The weight loss of Formulation XI was measured via TGA and was found to be 0.31%.

The itraconazole content of Formulation XI was measured with HPLC-UV and is 99.7%.

The crystallinity of Formulation XI was assessed via XRD. The diffraction pattern of itraconazole is observed in the formulation, suggesting the milling or spray drying process does not affect the solid-state of itraconazole. Additional peaks observed in the pattern correspond to the additional excipients in the formulations. (FIG. 5)

Example 7. Dry Powder Formulations of Polysorbate 80-Stabilized Crystalline Itraconazole of Varying Particle Sizes Containing Sodium Sulfate/Leucine A. Powder Preparation.

The nanocrystalline itraconazole for Formulation XII was prepared by compounding 30.090 g of itraconazole (Neuland ITI0114005 and ITI0714011) in 87.262 g of water and 3.009 g of polysorbate 80. 129.625 g of 500 μm polystyrene milling media (Dow Chemical, Midland Mich.) was then added to the suspension, and the suspension was milled at 1800 rpm for one hour before being collected. The final median particle size (Dv(50)) of the milled suspension was 132 nm. This process is called the "Wet milling process #1", hereafter.

The nanocrystalline itraconazole for Formulation XIII was prepared as a suspension comprising 10 wt % itraconazole and 1.0 wt % polysorbate 80 in deionized water. The polysorbate 80 was dissolved in 89.0% DI water via magnetic stir bar, then the itraconazole was slowly added also with a magnetic stir bar. Once all of the itraconazole was suspended the formulation was processed on the M-110P Microfluidizer processor at 30,000 psi for 120 passes using an ice water cooling coil to cool the material during processing. The final median particle size (Dv(50)) of the milled suspension was 198 nm. This process is called the "Microfluidics process #1", hereafter.

The nanocrystalline itraconazole for Formulation XIV was prepared by compounding 30.090 g of itraconazole (Neuland ITI0114005) in 87.26195 g of water and 3.009 g of polysorbate 80. 129.625 g of 500 μm polystyrene milling media (Dow Chemical, Midland Mich.) was then added to the suspension, and the suspension was milled at 1000 rpm for 30 minutes before being collected. The final median particle size (Dv(50)) of the milled suspension was 258 nm. This process is called the "Wet milling process #2", hereafter.

The microcrystalline itraconazole for Formulation XV was prepared using a Qualification Micronizer jet mill (Sturtevant, Hanover, Mass. USA). The feed pressure was set to 90 psig and the grind pressure was set to 40 psig. Itraconazole was continuously fed into the mill until 60.3 g of itraconazole was milled. The final median particle size (Dv(50)) of the milled API was 1600 nm. This process is called the "Jet milling process #1", hereafter. The micronized itraconazole for Formulation XV was then compounded into a suspension consisting of 10 wt % itraconazole and 1.0 wt % polysorbate 80 in deionized water. The batch size was 200 g. The polysorbate 80 was dissolved in 89.0% DI water via magnetic stir bar, then the itraconazole was slowly added and allowed to mix until the suspension was observed to be visually dispersed and homogeneous.

Feedstock solutions were prepared and used to manufacture dry powders composed of crystalline itraconazole, polysorbate 80 and other additional excipients. A drug load of 50 wt % itraconazole, on a dry basis, was targeted. The feedstock solutions that were used to spray dry particles were made as follows. The required quantity of water was weighed into a suitably sized glass vessel. The excipients were added to the water and the solution allowed to stir until visually clear. The itraconazole-containing suspension was then added to the excipient solution and stirred until visually homogenous. The feedstocks were then spray-dried. Feedstocks were stirred while spray dried. Feedstock masses were 166.67 g to 1219.4 g, which supported manufacturing campaigns of 30 minutes to 3.5 hours. Table 27 lists the components of the feedstocks used in preparation of the dry powders.

TABLE 27

Feedstock compositions

| Formulation | Water (g) | Itraconazole (g) | Polysorbate 80 (g) | Sodium sulfate (g) | Leucine (g) | Total mass (gm) |
|---|---|---|---|---|---|---|
| XII | 1183.17 | 18.3 | 1.83 | 12.8009 | 3.662 | 1219.7629 |
| XIII | 161.654 | 2.501 | 0.250 | 1.57553 | 0.67525 | 166.6555 |
| XIV | 1080.13 | 16.70 | 1.670 | 11.69625 | 3.34343 | 1113.5397 |
| XV | 1079.619 | 16.71 | 1.671 | 11.69165 | 3.34353 | 1113.035 |

Dry powders of Formulations XII-XV were manufactured from these feedstocks by spray drying on the Büchi B-290 Mini Spray Dryer (BÜCHI Labortechnik AG, Flawil, Switzerland) with cyclone powder collection. The system was run in open-loop (single pass) mode using nitrogen as the drying and atomization gas. Atomization of the liquid feed utilized a Büchi nozzle with 1.5 mm cap and 0.7 liquid tip. The aspirator of the system was adjusted to maintain the system pressure at −2.0" water column.

The following spray drying conditions were followed to manufacture the dry powder. For Formulations XII, XIV, and XV, the liquid feedstock solids concentration was 3%, the process gas inlet temperature was 127° C. to 140° C., the process gas outlet temperature was 60° C., the drying gas flowrate was 17.0 kg/hr, the atomization gas flowrate was 30.0 g/min, and the liquid feedstock flowrate was 6.0 mL/min. The resulting dry powder formulations are reported in Table 28.

The following spray drying conditions were followed to manufacture the dry powder. For Formulation XIII, the liquid feedstock solids concentration was 3%, the process gas inlet temperature was 134° C., the process gas outlet temperature was 60° C., the drying gas flowrate was 17.0 kg/hr, the atomization gas flowrate was 30.4 g/min, and the liquid feedstock flowrate was 6.0 mL/min. The resulting dry powder formulations are reported in Table 28.

TABLE 28

Dry powder composition, dry basis

| Formulation | Description | Dry Powder Composition (w/w), dry basis |
|---|---|---|
| XII | Wet milling process #1 | 50% itraconazole, 35% sodium sulfate, 10% leucine, 5% polysorbate 80 |
| XIII | Microfluidics process #1 | 50% itraconazole, 35% sodium sulfate, 10% leucine, 5% polysorbate 80 |
| XIV | Wet milling process #2 | 50% itraconazole, 35% sodium sulfate, 10% leucine, 5% polysorbate 80 |
| XV | Jet milling process #1 | 50% itraconazole, 35% sodium sulfate, 10% leucine, 5% polysorbate 80 |

B. Powder Characterization.

The bulk particle size characteristics for the four formulations are found in Table 29. The span at 1 bar of less than 2.10 for Formulations XII-XV indicates a relatively narrow size distribution. The 1 bar/4 bar dispersibility ratio less than 1.25 for Formulations XII-XV indicate that they are relatively independent of dispersion energy, a desirable characteristic which allows similar particle dispersion across a range of dispersion energies.

TABLE 29

Bulk particle size

| Formulation | 0.5 bar Dv[50] (μm) | Span | 1 bar Dv[50] (μm) | Span | 4 bar Dv[50] (μm) | Span | 1 bar:4 bar Dv[50] ratio |
|---|---|---|---|---|---|---|---|
| XII | 3.61 | 2.01 | 3.46 | 2.08 | 3.05 | 2.15 | 1.14 |
| XIII | 2.78 | 1.73 | 2.56 | 1.90 | 2.43 | 1.86 | 1.05 |
| XIV | 4.11 | 2.03 | 3.94 | 2.04 | 3.23 | 2.21 | 1.22 |
| XV | 3.61 | 2.02 | 3.44 | 2.06 | 2.96 | 2.10 | 1.16 |

The geometric particle size and capsule emitted powder mass (CEPM) measured and/or calculated at 60 liters per minute (LPM) and 30 LPM simulated patient flow rates were measured for Formulations XII, XIV, and XV and reported in Table 30. The small changes in CEPM and geometric size from 60 LPM to 30 LPM indicates that the dry powder formulations are relatively independent of patient inspiratory flowrate, indicating that patients breathing in at varying flow rates would receive a relatively similar therapeutic dose. Emitted particle size testing was not performed for Formulation XIII due to lack of sufficient material quantities.

TABLE 30

Emitted particle size

| Formulation | 30 LPM | | 60 LPM | |
| --- | --- | --- | --- | --- |
| | CEPM (%) | Dv[50] (μm) | CEPM (%) | Dv[50] (μm) |
| XII | 99.3 | 4.35 | 99.8 | 3.97 |
| XIII | NT | NT | NT | NT |
| XIV | 99.2 | 5.37 | 99.8 | 4.98 |
| XV | 99.1 | 4.82 | 99.6 | 4.34 |

NT = Not tested

The aerodynamic particle size, fine particle fractions and fine particle doses measured and/or calculated with an eight-stage Anderson Cascade Impactor (ACI-8) or Next Generation Impactor (NGI) are reported in Table 31. The fine particle dose for Formulation XII through XV all indicate that greater than 30% of the nominal dose reaches the impactor stages and so would be predicted to be delivered to the lungs. The MMAD of Formulation XII through XV range from 3.42 to 4.76, indicating deposition in the central and conducting airways.

TABLE 31

Aerodynamic particle size

| Formulation | Test Method | MMAD (μm) | FPD < 5 μm (% nominal dose) |
| --- | --- | --- | --- |
| XII | NGI | 4.22 | 38.3 |
| XIII | NGI | 3.42 | 48.2 |
| XIV | ACI-8 | 4.73 | 30.6 |
| XV | NGI | 4.76 | 33.5 |

The weight loss of Formulations VII and VIII were measured via TGA and are detailed in Table 32.

TABLE 32

Weight loss (%) via TGA

| Formulation | Weight loss via TGA (%) |
| --- | --- |
| XII | 0.10 |
| XIII | 0.18 |
| XIV | 0.08 |
| XV | 0.06 |

The itraconazole content of Formulations VII and VIII were measured with HPLC-UV and are detailed in Table 33.

TABLE 33

Itraconazole content

| Formulation | Itraconazole content (% label claim) |
| --- | --- |
| XII | 100.4 |
| XIII | 101.5 |
| XIV | 101.1 |
| XV | 97.9 |

Figure 6:
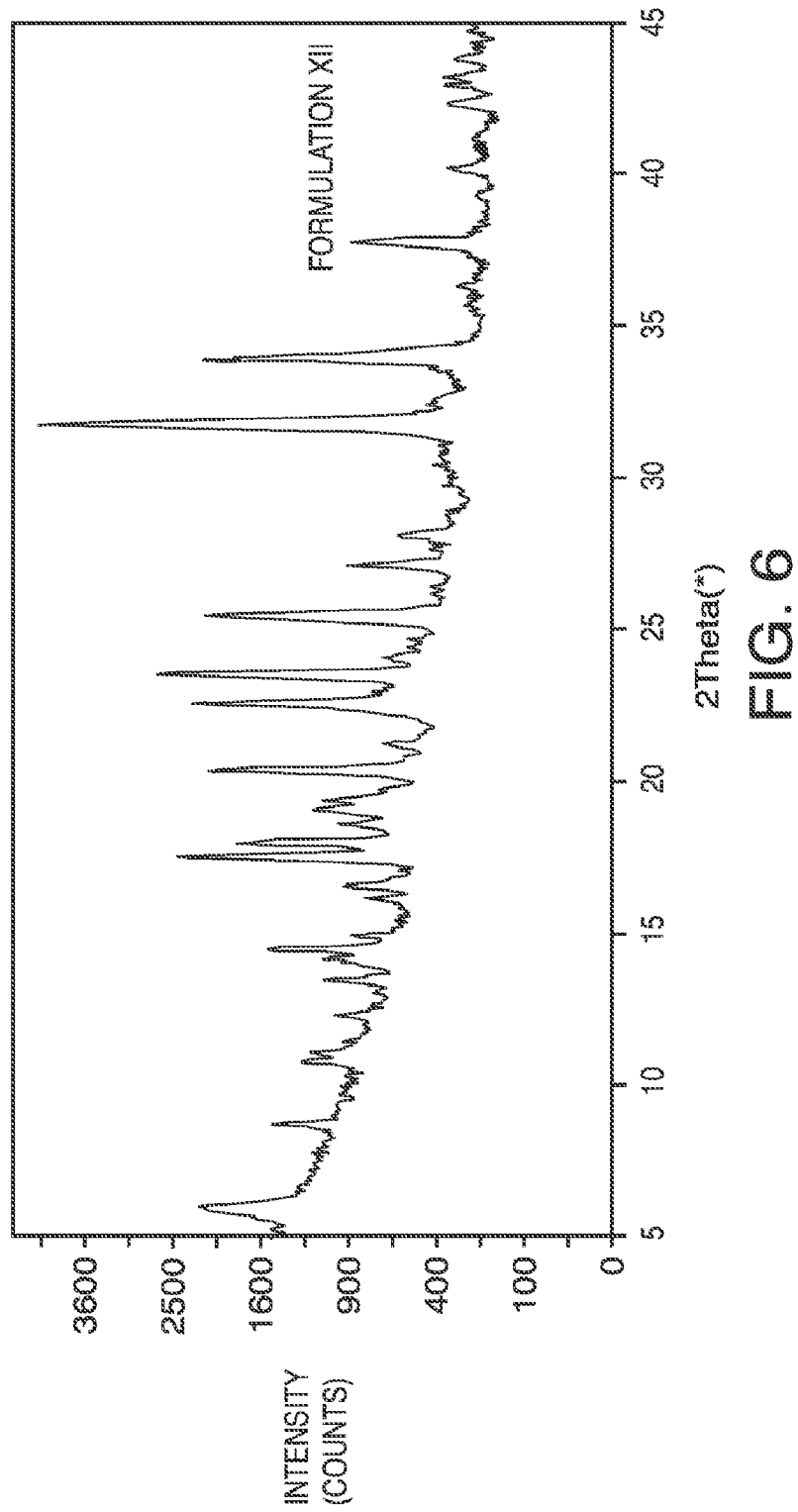
FIG. 6: Particle X-Ray Diffraction plot for Formulations XII.

The crystallinity of Formulation XII was assessed via XRD. The diffraction pattern of itraconazole is observed in the formulation, suggesting the milling or spray drying process does not affect the solid-state of itraconazole. Additional peaks observed in the pattern correspond to the additional excipients in the formulations. (FIG. 6)

Figure 7:
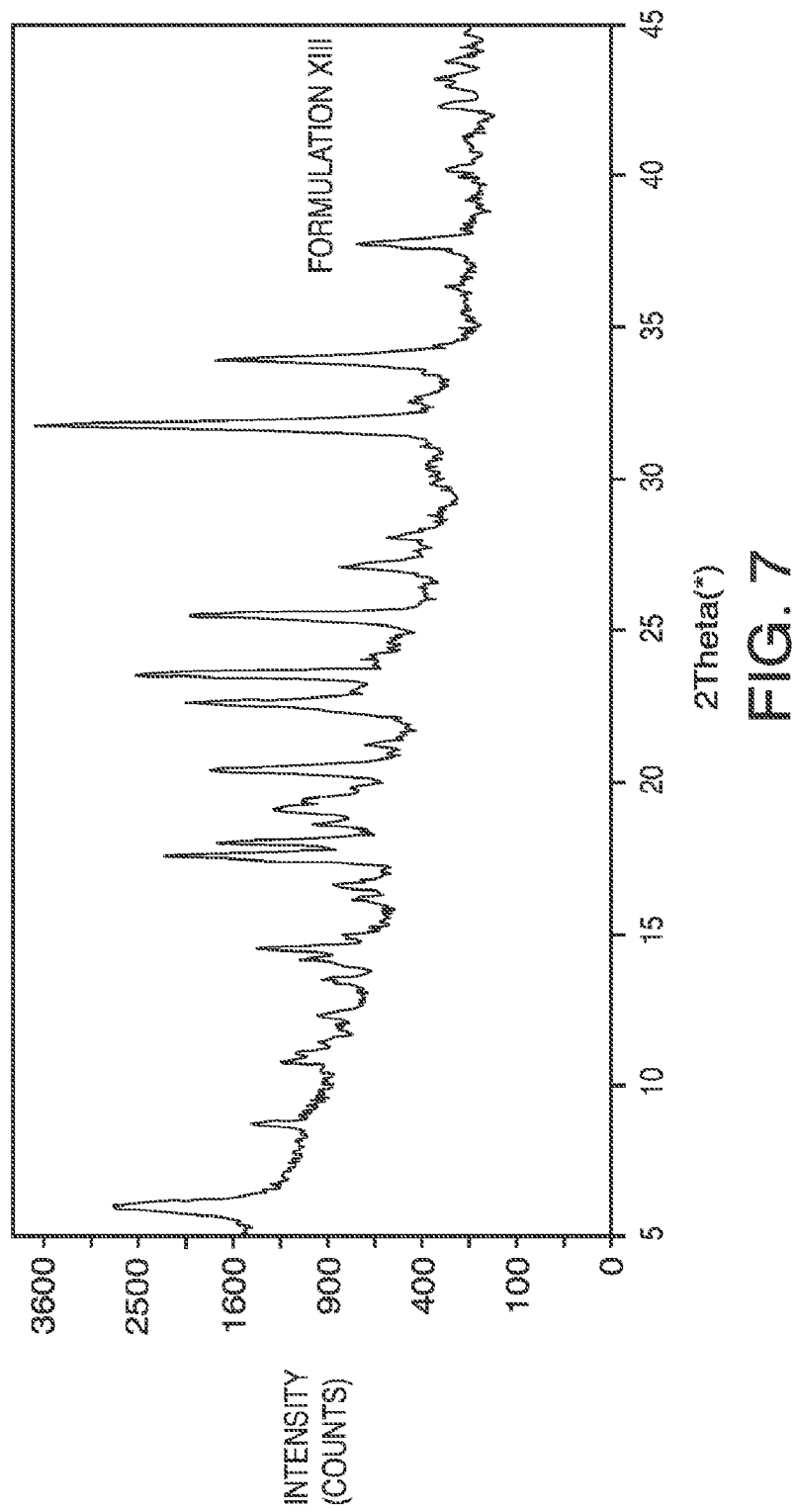
FIG. 7: Particle X-Ray Diffraction plot for Formulations XIII.

The crystallinity of Formulation XIII was assessed via XRD. The diffraction pattern of itraconazole is observed in the formulation, suggesting the milling or spray drying process does not affect the solid-state of itraconazole. Additional peaks observed in the pattern correspond to the additional excipients in the formulations. (FIG. 7)

Figure 8:
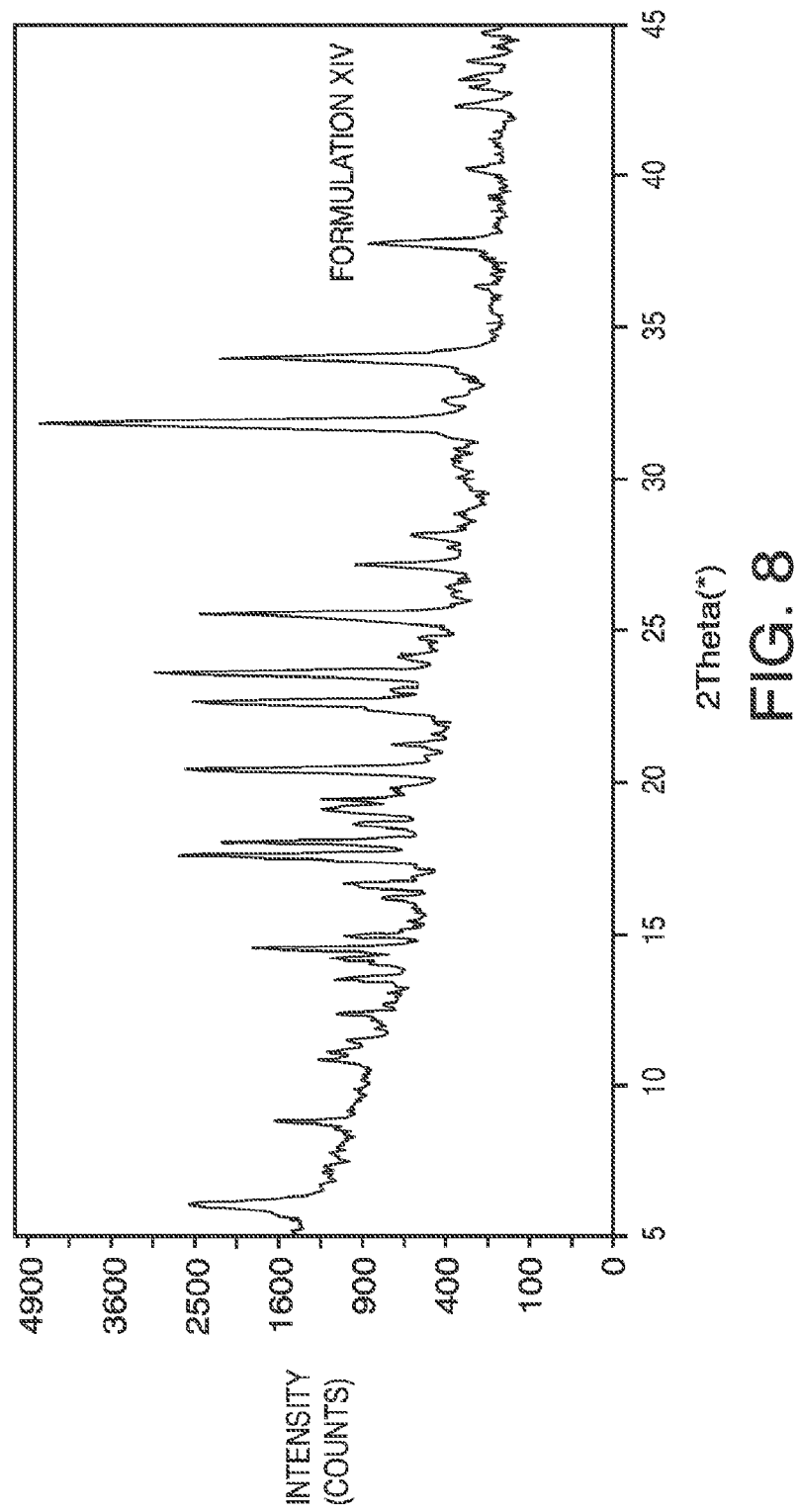
FIG. 8: Particle X-Ray Diffraction plot for Formulations XIV.

The crystallinity of Formulation XIV was assessed via XRD. The diffraction pattern of itraconazole is observed in the formulation, suggesting the milling or spray drying process does not affect the solid-state of itraconazole. Additional peaks observed in the pattern correspond to the additional excipients in the formulations. (FIG. 8)

Figure 9:
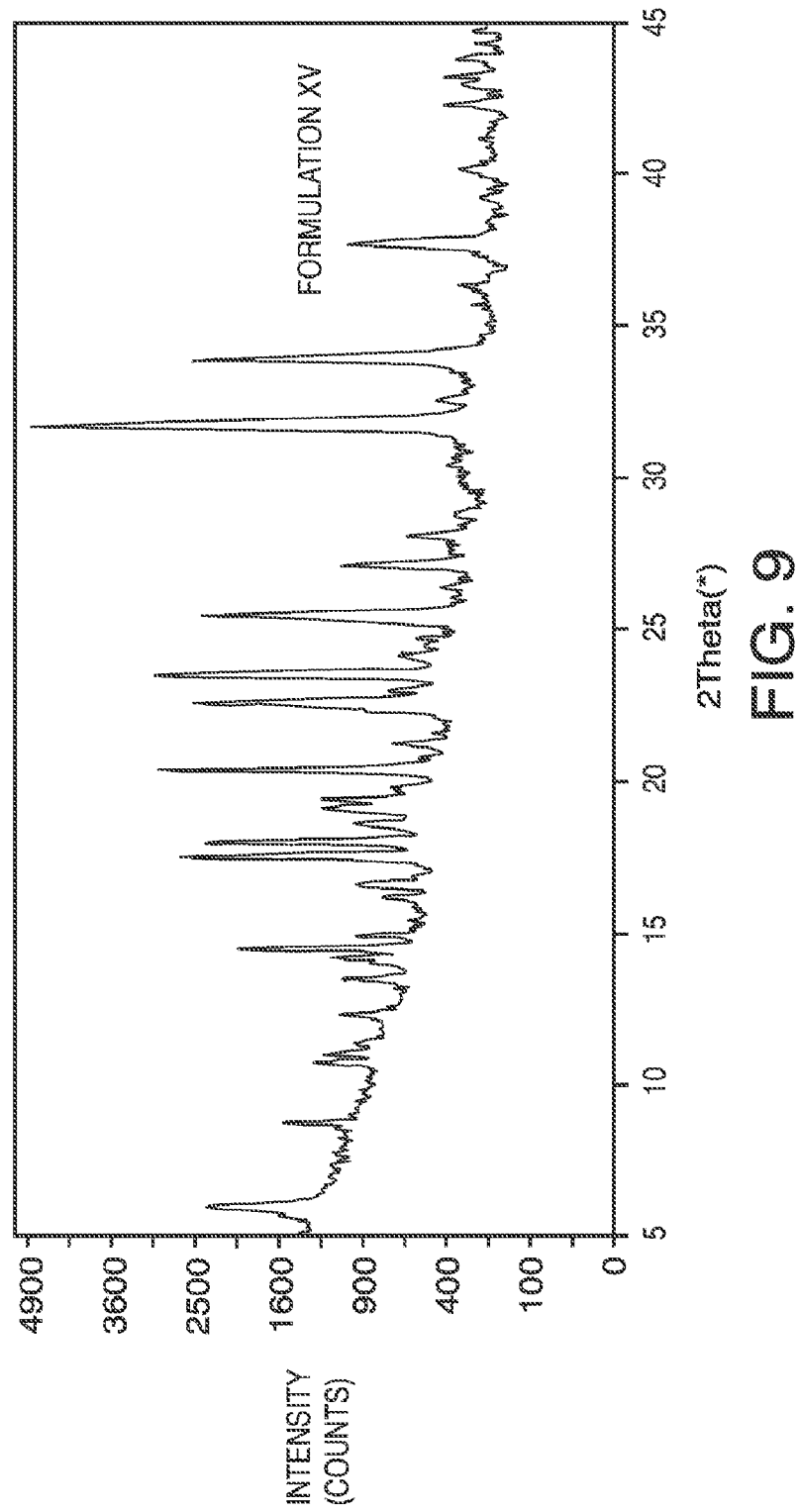
FIG. 9: Particle X-Ray Diffraction plot for Formulations XV.

The crystallinity of Formulation XV was assessed via XRD. The diffraction pattern of itraconazole is observed in the formulation, suggesting the milling or spray drying process does not affect the solid-state of itraconazole. Additional peaks observed in the pattern correspond to the additional excipients in the formulations. (FIG. 9)

Example 8. Dry Powder Formulation of Polysorbate 80-Stabilized Crystalline Itraconazole Containing Sodium Sulfate/Leucine and Reduced Levels of Polysorbate 80

A. Powder Preparation.

The microcrystalline itraconazole for Formulation XVI was prepared using a Qualification Micronizer jet mill (Sturtevant, Hanover, Mass. USA). The feed pressure was set to 90 psig and the grind pressure was set to 40 psig. Itraconazole (SMS Pharma, Lot ITZ-0715005) was continuously fed into the mill until about 60 g of itraconazole was milled. The final median particle size (Dv(50)) of the milled API was about 1510 nm.

The microcrystalline itraconazole for Formulation XVI was then compounded into a suspension consisting of 10 wt % itraconazole and 0.25 wt % polysorbate 80 in deionized water. The batch size was 440 g. The polysorbate 80 was dissolved in 89.75% DI water via magnetic stir bar, then the micronized itraconazole was slowly added and allowed to mix until the suspension was observed to be visually dispersed and homogeneous.

A feedstock solution was prepared and used to manufacture a dry powder composed of nanocrystalline itraconazole, polysorbate 80 and other additional excipients. A drug load of 50 wt % itraconazole, on a dry basis, was targeted. The feedstock solution that was used to spray dry particles were made as follows. The required quantity of water was weighed into a suitably sized glass vessel. The excipients were added to the water and the solution allowed to stir until visually clear. The itraconazole-containing suspension was then added to the excipient solution and stirred until visually homogenous. The feedstock was then spray-dried. The feedstock volume was 3000 g, which supported a manufacturing campaign of approximately one hour. Table 34 lists the components of the feedstock used in preparation of the dry powder.

TABLE 34

Feedstock composition

| Formulation | Water (g) | Itraconazole (g) | Polysorbate 80 (g) | Sodium sulfate (g) | Leucine (g) | Total mass (gm) |
| --- | --- | --- | --- | --- | --- | --- |
| XVI | 2964.2310 | 18.0225 | 0.4500 | 12.6 | 5.1 | 3000.3 |

A dry powder of Formulation XVI was manufactured from this feedstock by spray drying on the Niro Mobile Minor spray dryer (GEA Process Engineering Inc., Columbia, Md.) with bag filter collection. The system was run in open-loop (single pass) mode using nitrogen as the drying and atomization gas. Atomization of the liquid feed utilized a Schlick 940-0 atomizer with a 1.0 mm liquid insert. The aspirator of the system was adjusted to maintain the system pressure at −2.0" water column.

The following spray drying conditions were followed to manufacture the dry powder. For Formulations XVI, the liquid feedstock solids concentration was 1.2%, the process gas inlet temperature was 181° C. to 185° C., the process gas outlet temperature was 65° C., the drying gas flowrate was 80 kg/hr, the atomization gas flowrate was 250 g/min, the atomization gas backpressure at the atomizer inlet was 30.4 psig to 31.4 psig and the liquid feedstock flowrate was 50 mL/min. The resulting dry powder formulation is reported in Table 35.

TABLE 35

Dry powder composition, dry basis

| Formulation | Dry Powder Composition (w/w), dry basis |
|---|---|
| XVI | 50% itraconazole, 35% sodium sulfate, 13.75% leucine, 1.25% polysorbate 80 |

B. Powder Characterization.

The bulk particle size characteristics for the formulation are found in Table 36. The span at 1 bar of 1.93 for Formulations XVII, indicates a relatively narrow size distribution. The 1 bar/4 bar dispersibility ratio of 1.03 for Formulations XVIII, indicates the particle size is relatively independent of dispersion energy, a desirable characteristic which allows similar dispersion across a range of dispersion energies.

TABLE 36

Bulk particle size

| | 0.5 bar | | 1 bar | | 4 bar | | 1 bar:4 bar |
|---|---|---|---|---|---|---|---|
| Formulation | Dv[50] (µm) | Span | Dv[50] (µm) | Span | Dv[50] (µm) | Span | Dv[50] ratio |
| XVI | 2.13 | 1.77 | 2.02 | 1.93 | 1.96 | 1.87 | 1.03 |

The weight loss of Formulation XVI was measured via TGA and was found to be 0.37%.

Figure 10:
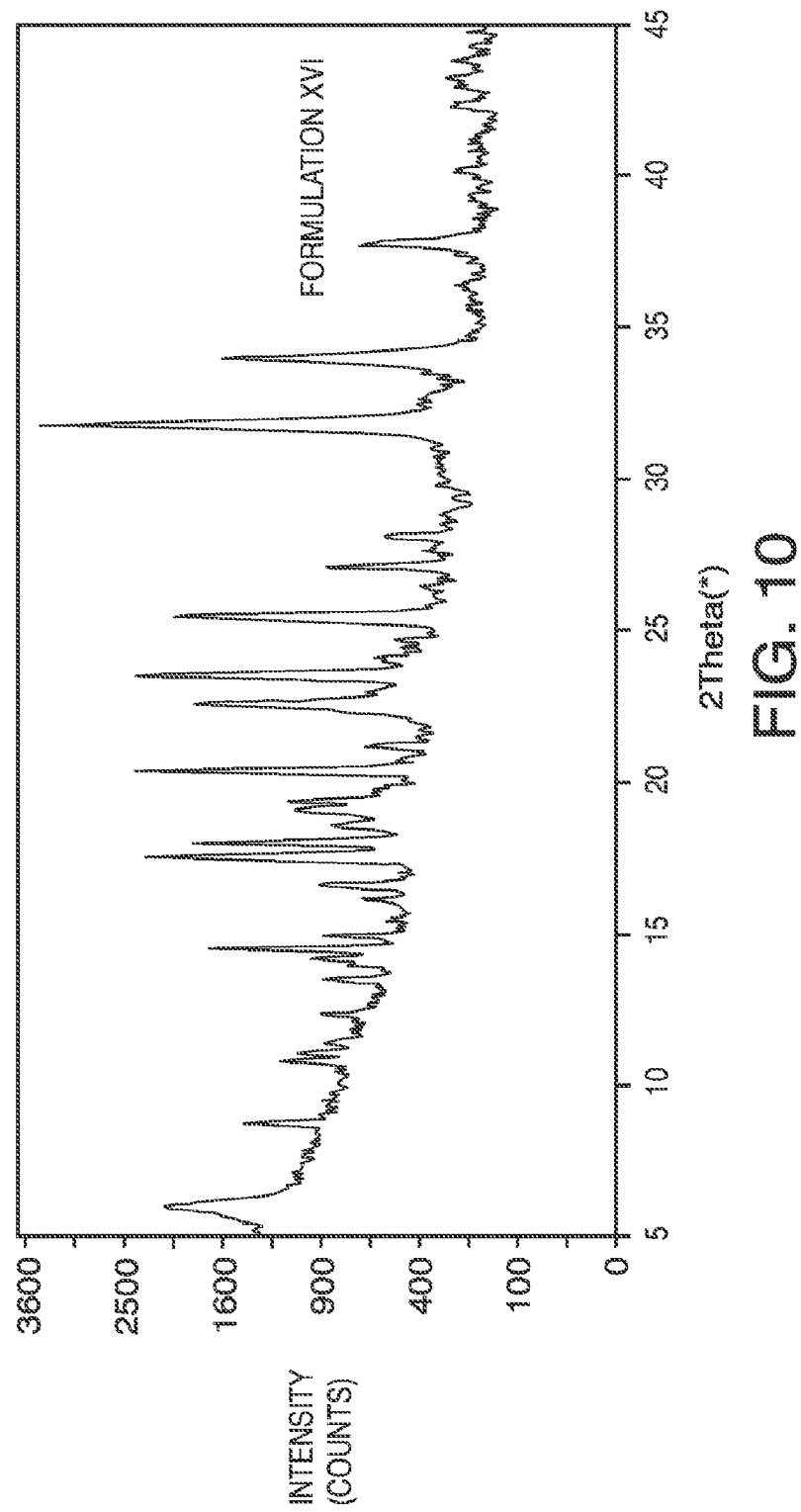
FIG. 10: Particle X-Ray Diffraction plot for Formulations XVI.

The crystallinity of Formulation XVI was assessed via XRD. The diffraction pattern of itraconazole is observed in the formulation, suggesting the milling or spray drying process does not affect the solid-state of itraconazole. Additional peaks observed in the pattern correspond to the additional excipients in the formulations. (FIG. 10)

Example 9. Dry Powder Formulation of Polysorbate 80-Stabilized Nanocrystalline Amphotericin B Containing Sodium Sulfate/Leucine A. Powder Preparation.

The nanocrystalline amphotericin B was prepared by compounding four individual aliquots of 1.9 g of amphotericin B (Synbiotics 15A02NO3) in 16.96 g of water and 0.190 g of polysorbate 80 (Acros Organics, A0365196) in a 30 mL glass jar. 57.88 g of 300 µm yttria-stabilized zirconia (YTZ) ceramic milling media (TOSOH, Japan) was then added to the suspension, and the suspension was milled at 200 rpm for twenty-one hours before being collected. The individual samples were combined to make one lot of suspension The final median particle size (Dv(50)) of the milled suspension was 134 nm.

A feedstock solution was prepared and used to manufacture a dry powder composed of nanocrystalline amphotericin B, polysorbate 80 and other additional excipients. A drug load of 50 wt % amphotericin B, on a dry basis, was targeted. The feedstock solution that was used to spray dry particles were made as follows. The required quantity of water was weighed into a suitably sized glass vessel. The excipients were added to the water and the solution allowed to stir until visually clear. The amphotericin B-containing suspension was then added to the excipient solution and stirred until visually homogenous. The feedstock was then spray-dried. The feedstock volume was 250 g, which supported a manufacturing campaign of approximately 45 minutes. Table 37 lists the components of the feedstock used in preparation of the dry powder.

TABLE 37

Feedstock composition

| Formulation | Water (g) | Amphotericin B (g) | Polysorbate 80 (g) | Sodium sulfate (g) | Leucine (g) | Total mass (gm) |
|---|---|---|---|---|---|---|
| XVII | 245.35 | 2.496 | 0.2496 | 1.76988 | 0.50170 | 250.3672 |

A dry powder of Formulation XVII was manufactured from this feedstock by spray drying on the Büchi B-290 Mini Spray Dryer (BÜCHI Labortechnik AG, Flawil, Switzerland) with cyclone powder collection. The system was run in open-loop (single pass) mode using nitrogen as the drying and atomization gas. Atomization of the liquid feed utilized a Büchi nozzle with 1.5 mm cap and 0.7 mm liquid tip. The aspirator of the system was adjusted to maintain the system pressure at −2.0" water column.

The following spray drying conditions were followed to manufacture the dry powder. For Formulations XVII, the liquid feedstock solids concentration was 2.0%, the process gas inlet temperature was 132° C. to 138° C., the process gas outlet temperature was 60° C., the drying gas flowrate was 17.0 kg/hr, the atomization gas flowrate was 30.4 g/min, and the liquid feedstock flowrate was 6.0 mL/min. The resulting dry powder formulation is reported in Table 38.

TABLE 38

Dry powder composition, dry basis

| Formulation | Dry Powder Composition (w/w), dry basis |
|---|---|
| XVII | 50% amphotericin B, 35% sodium sulfate, 10% leucine, 5% polysorbate 80 |

B. Powder Characterization.

The bulk particle size characteristics for the formulation are found in Table 39. The span at 1 bar of 2.02 for Formulations XVII, indicates a relatively narrow size distribution. The 1 bar/4 bar dispersibility ratio of 1.02 for Formulations XVII, indicates the particle size is relatively independent of dispersion energy, a desirable characteristic which allows similar dispersion across a range of dispersion energies.

TABLE 39

| | Bulk particle size | | | | | | |
|---|---|---|---|---|---|---|---|
| | 0.5 bar | | 1 bar | | 4 bar | | 1 bar:4 bar |
| Formulation | Dv[50] (μm) | Span | Dv[50] (μm) | Span | Dv[50] (μm) | Span | Dv[50] ratio |
| XVII | 3.11 | 1.99 | 3.02 | 2.02 | 2.96 | 2.04 | 1.02 |

The aerodynamic particle size, fine particle fractions and fine particle doses measured and/or calculated with a Next Generation Impactor (NGI) are reported in Table 40. The fine particle dose for Formulation XVII indicates a high percentage of the nominal dose which is filled into the capsule reaches the impactor stages (40.5%) and so would be predicted to be delivered to the lungs. The MMAD of Formulation XVII was 3.90 microns, indicating deposition in the central and conducting airways.

TABLE 40

| | Aerodynamic particle size | |
|---|---|---|
| Formulation | MMAD (μm) | FPD < 5 μm (% nominal dose) |
| XVII | 3.90 | 40.5 |

The weight loss of Formulation XVII was measured via TGA and was found to be 3.58%.

Figure 11:
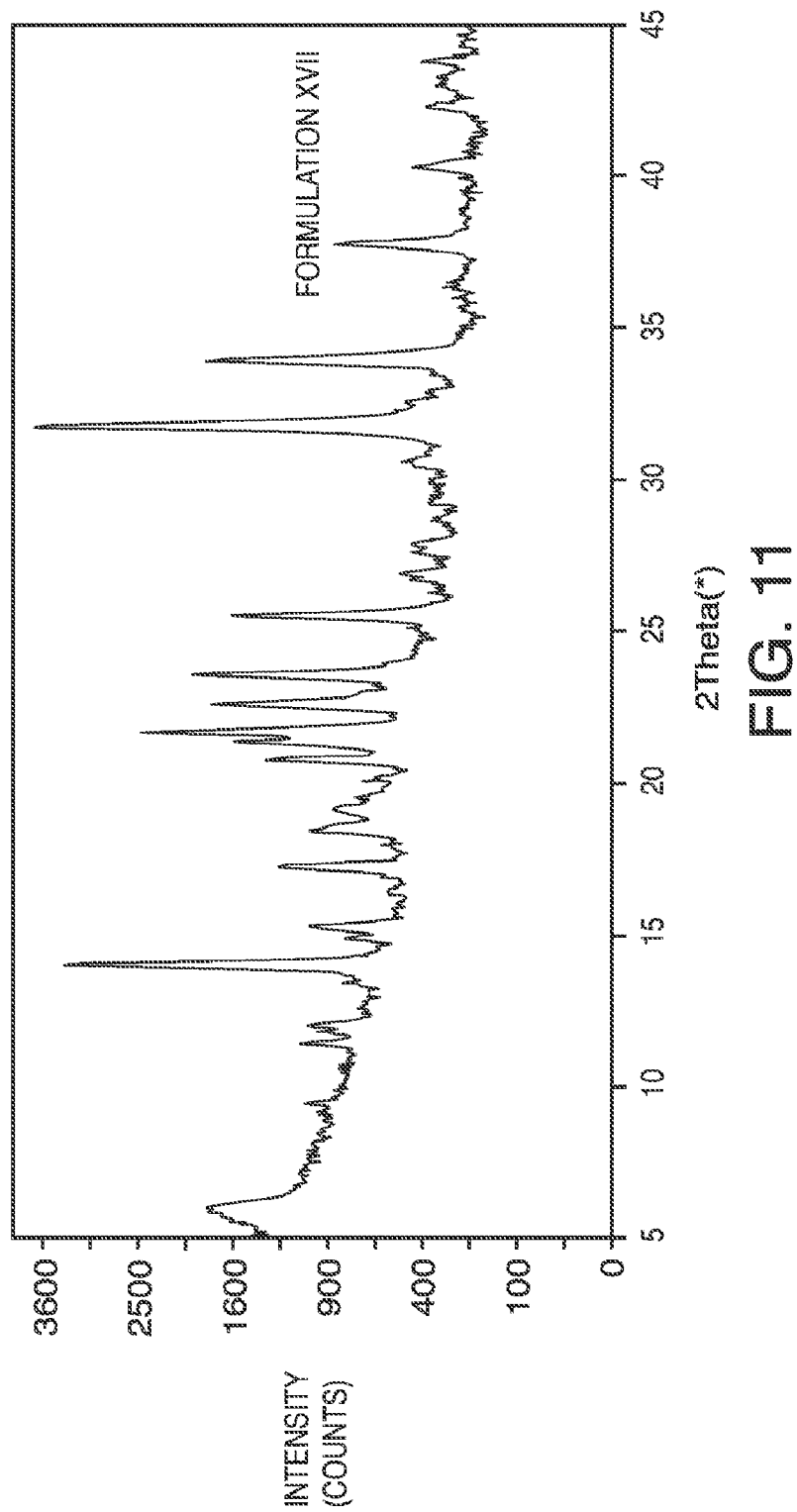
FIG. 11: Particle X-Ray Diffraction plot for Formulations XVII.

The crystallinity of Formulation XVII was assessed via XRD. The diffraction pattern of amphotericin B is observed in the formulation, suggesting the milling or spray drying process does not affect the solid-state of amphotericin B. Additional peaks observed in the pattern correspond to the additional excipients in the formulations. (FIG. 11)

Example 10. Dry Powder Formulation of Polysorbate 80-Stabilized Nanocrystalline Amphotericin B Containing Sodium Chloride/Leucine A. Powder Preparation.

The nanocrystalline amphotericin B was prepared by compounding four individual aliquots of 1.9 g of amphotericin B (Synbiotics 15A02NO3) in 16.96 g of water and 0.190 g of polysorbate 80 (Acros Organics A0365196) in a 30 mL glass jar. 57.88 g of 300 μm yttria-stabilized zirconia (YTZ) ceramic milling media (TOSOH, Japan) was then added to the suspension, and the suspension was milled at 200 rpm for twenty-one hours before being collected. The individual samples were combined to make one lot of suspension The final median particle size (Dv(50)) of the milled suspension was 134 nm.

A feedstock solution was prepared and used to manufacture a dry powder composed of nanocrystalline amphotericin B, polysorbate 80 and other additional excipients. A drug load of 50 wt % amphotericin B, on a dry basis, was targeted. The feedstock solution that was used to spray dry particles were made as follows. The required quantity of water was weighed into a suitably sized glass vessel. The excipients were added to the water and the solution allowed to stir until visually clear. The amphotericin B-containing suspension was then added to the excipient solution and stirred until visually homogenous. The feedstock was then spray-dried. The feedstock volume was 250 g, which supported a manufacturing campaign of approximately 45 minutes. Table 41 lists the components of the feedstock used in preparation of the dry powder.

TABLE 41

| | Feedstock composition | | | | | |
|---|---|---|---|---|---|---|
| Formulation | Water (g) | Amphotericin B (g) | Polysorbate 80 (g) | Sodium chloride (g) | Leucine (g) | Total mass (gm) |
| XVIII | 246.05 | 2.5 | 0.25 | 1.76937 | 0.50332 | 251.07269 |

A dry powder of Formulation XVII was manufactured from this feedstock by spray drying on the Büchi B-290 Mini Spray Dryer (BÜCHI Labortechnik AG, Flawil, Switzerland) with cyclone powder collection. The system was run in open-loop (single pass) mode using nitrogen as the drying and atomization gas. Atomization of the liquid feed utilized a Büchi nozzle with 1.5 mm cap and 0.7 mm liquid tip. The aspirator of the system was adjusted to maintain the system pressure at −2.0″ water column.

The following spray drying conditions were followed to manufacture the dry powder. For Formulations XVIII, the liquid feedstock solids concentration was 2.0%, the process gas inlet temperature was 131° C. to 132° C., the process gas outlet temperature was 60° C., the drying gas flowrate was 17.0 kg/hr, the atomization gas flowrate was 30.4 g/min, and the liquid feedstock flowrate was 6.0 mL/min. The resulting dry powder formulation is reported in Table 42.

TABLE 42

| | Dry powder composition, dry basis |
|---|---|
| Formulation | Dry Powder Composition (w/w), dry basis |
| XVIII | 50% amphotericin B, 35% sodium chloride, 10% leucine, 5% polysorbate 80 |

B. Powder Characterization.

The bulk particle size characteristics for the formulation are found in Table 43. The span at 1 bar of 2.27 for Formulation XVIII, indicates a relatively narrow size distribution. The 1 bar/4 bar dispersibility ratio of 1.01 for Formulation XVIII, indicates the particle size is relatively independent of dispersion energy, a desirable characteristic which allows similar dispersion across a range of dispersion energies.

TABLE 43

| | Bulk particle size | | | | | | |
|---|---|---|---|---|---|---|---|
| | 0.5 bar | | 1 bar | | 4 bar | | 1 bar:4 bar |
| Formulation | Dv[50] (μm) | Span | Dv[50] (μm) | Span | Dv[50] (μm) | Span | Dv[50] ratio |
| XVIII | 2.71 | 2.25 | 2.68 | 2.27 | 2.67 | 2.23 | 1.01 |

The aerodynamic particle size, fine particle fractions and fine particle doses measured and/or calculated with a Next Generation Impactor (NGI) are reported in Table 44. The fine particle dose for Formulation XVIII indicates a high percentage of the nominal dose which is filled into the capsule reaches the impactor stages (47.4%) and so would be predicted to be delivered to the lungs. The MMAD of Formulation XVIII was 3.91 microns, indicating deposition in the central and conducting airways.

TABLE 44

Aerodynamic particle size

| Formulation | MMAD (μm) | FPD < 5 μm (% nominal dose) |
|---|---|---|
| XVIII | 3.91 | 47.4 |

The weight loss of Formulation XVIII was measured via TGA and was found to be 3.35%.

Figure 12:
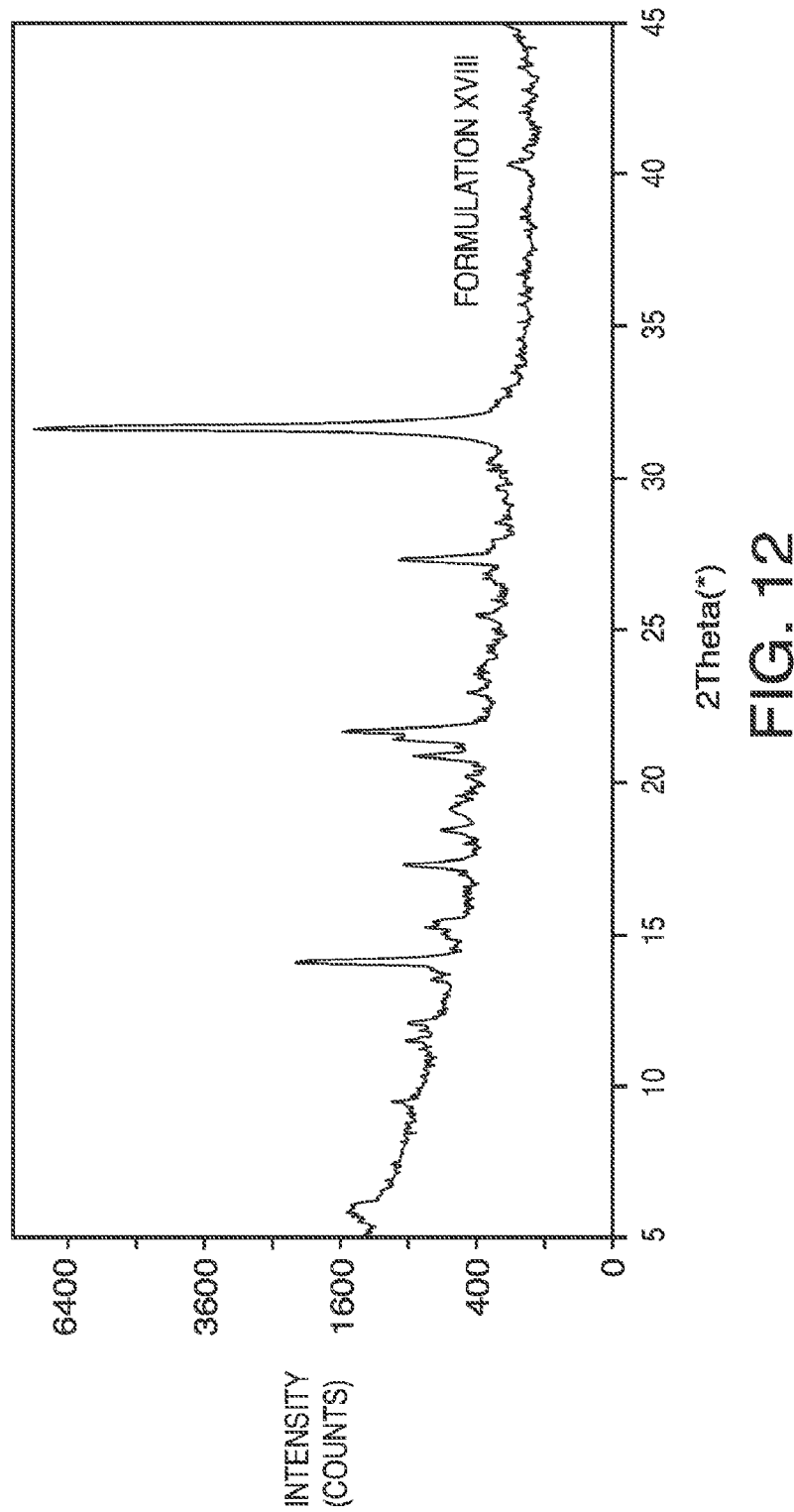
FIG. 12: Particle X-Ray Diffraction plot for Formulations XVIII.

The crystallinity of Formulation XVIII was assessed via XRD. The diffraction pattern of amphotericin B is observed in the formulation, suggesting the milling or spray drying process does not affect the solid-state of amphotericin B. Additional peaks observed in the pattern correspond to the additional excipients in the formulations. (FIG. 12)

Example 11. Spray-Dried Dry Powder Formulation of Itraconazole, Sodium Sulfate and Leucine A. Powder Preparation.

A feedstock solution utilizing a water-tetrahydrofuran (THF) co-solvent system was prepared and used to manufacture a dry powder composed of itraconazole, sodium sulfate and leucine. A drug load of 50 wt % itraconazole, on a dry basis, was targeted. The feedstock solution that was used to spray dry particles was made as follows. The required quantity of water was weighed into a suitably sized glass vessel. The excipients were added to the water and the solution allowed to stir until visually clear. The required amount of THF was weighed into a suitably sized glass vessel. The itraconazole was added to the THF and the solution allowed to stir until visually clear. The itraconazole-containing THF solution was then added to the excipient solution and stirred until visually homogenous. The feedstock was then spray-dried. The feedstock volume was 5 L, which supported a manufacturing campaign of approximately 8.5 hours. Table 45 lists the components of the feedstock used in preparation of the dry powder.

TABLE 45

Feedstock composition

| Formulation | Water (g) | Tetra-hydrofuran (g) | Itraconazole (g) | Sodium sulfate (g) | Leucine (g) | Total mass (gm) |
|---|---|---|---|---|---|---|
| XIX | 2246.1 | 2444.3 | 30.1 | 21.0 | 9.0 | 4750.5 |

A dry powder of Formulation XVII was manufactured from this feedstock by spray drying on the Büchi B-290 Mini Spray Dryer (BÜCHI Labortechnik AG, Flawil, Switzerland) with cyclone powder collection. The system was run in open-loop (single pass) mode using nitrogen as the drying and atomization gas. Atomization of the liquid feed utilized a Büchi nozzle with 1.5 mm cap and 0.7 mm liquid tip. The aspirator of the system was adjusted to maintain the system pressure at −2.0" water column.

The following spray drying conditions were followed to manufacture the dry powder. For Formulations XIX, the liquid feedstock solids concentration was 12.0 g/L, the process gas inlet temperature was 92° C. to 103° C., the process gas outlet temperature was 40° C., the drying gas flowrate was 17.0 kg/hr, the atomization gas flowrate was 2830 g/min, and the liquid feedstock flowrate was 10.0 mL/min. The resulting dry powder formulation is reported in Table 46.

TABLE 46

Dry powder composition, dry basis

| Formulation | Dry Powder Composition (w/w), dry basis |
|---|---|
| XIX | 50% itraconazole, 35% sodium sulfate, 15% leucine |

B. Powder Characterization.

The bulk particle size characteristics for the formulation are found in Table 47. The span at 1 bar of 2.32 for Formulations XIX, indicates a relatively narrow size distribution. The 1 bar/4 bar dispersibility ratio of 1.12 for Formulations XIX, indicates the particle size is relatively independent of dispersion energy, a desirable characteristic which allows similar dispersion across a range of dispersion energies.

TABLE 47

Bulk particle size

| Formulation | 0.5 bar | | 1 bar | | 4 bar | | 1 bar:4 bar |
|---|---|---|---|---|---|---|---|
| | Dv[50] (μm) | Span | Dv[50] (μm) | Span | Dv[50] (μm) | Span | Dv[50] ratio |
| XIX | 2.67 | 2.28 | 2.39 | 2.32 | 2.14 | 2.25 | 1.12 |

The geometric particle size and capsule emitted powder mass (CEPM) measured and/or calculated at 60 liters per minute (LPM) and 30 LPM simulated patient flow rates were measured for the formulation and reported in Table 48. The small changes in CEPM and geometric size from 60 LPM to 20 LPM indicates that the dry powder formulation is relatively independent of patient inspiratory flowrate, indicating that patients breathing in at varying flow rates would receive a relatively similar therapeutic dose.

TABLE 48

Emitted particle size

| Formulation | 30 LPM | | 60 LPM | |
|---|---|---|---|---|
| | CEPM (%) | Dv[50] (μm) | CEPM (%) | Dv[50] (μm) |
| XIX | 98.1 | 3.94 | 99.2 | 3.21 |

The aerodynamic particle size, fine particle fractions and fine particle doses measured and/or calculated with a Next Generation Impactor (NGI) are reported in Table 49. The fine particle dose for Formulation XIX indicates a high percentage of the nominal dose, which is filled into the capsule reaches the impactor stages (41.1%), and so would be predicted to be delivered to the lungs. The MMAD of Formulation XIX was 3.80 microns, indicating deposition in the central and conducting airways.

TABLE 49

Aerodynamic particle size

| Formulation | MMAD (μm) | FPD < 5 μm (% nominal dose) |
|---|---|---|
| XIX | 3.80 | 41.1 |

The weight loss of Formulation XIX was measured via TGA and was found to be 0.37%.

The itraconazole content of Formulation XIX was measured with HPLC-UV and is 99.0%.

Figure 13:
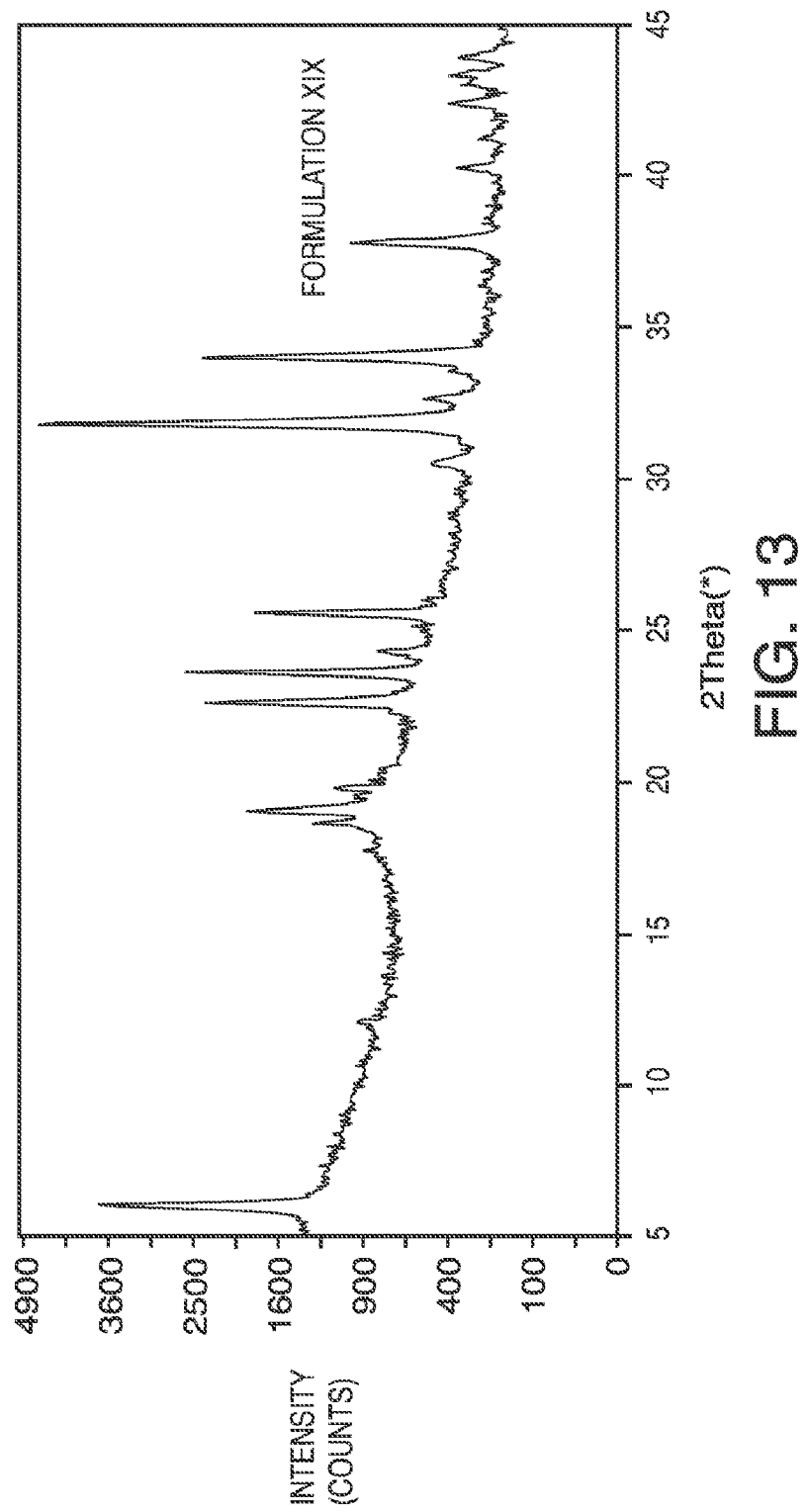
FIG. 13: Particle X-Ray Diffraction plot for Formulations XIX.

The crystallinity of Formulation XIX was assessed via XRD (FIG. 13). No itraconazole peaks are observed, indicating no appreciable levels of itraconazole are present in the formulation. As shown, all peaks observed in the formulation correspond to the excipients. The solid state of the itraconazole in Formulation XIX can therefore be characterized as amorphous.

Example 12. In Vitro Dissolution Study of Dry Powder Formulations Containing Itraconazole A. In Vitro Dissolution Study An in vitro model was utilized to provide a predictive test to understand the dissolution of itraconazole. Drug dissolution is a prerequisite for cellular uptake and/or absorption via the lungs. Hence, the dissolution kinetics of itraconazole plays a key role in determining the extent of its absorption from the respiratory tract. For dry particles containing itraconazole that are delivered to the respiratory tract as an aerosol, the fate of the itraconazole in those particles is dependent on their physicochemical properties. For the itraconazole in the aerosolized dry particles to exert a local effect in the lung, the dry particle must first undergo dissolution for the itraconazole to be present in the lung fluid and tissue to thereby act on a fungal infection. However, once dissolution of the itraconazole into the lung fluid has occurred, the itraconazole may further become available for permeation and systemic absorption. The rate of dissolution of itraconazole was predicted to be proportional to its solubility, concentration in surrounding liquid film and area of solid-liquid interface. Solubility is dependent on compound, formulation and physical form of the drug. The total liquid volume in the lung is 10-30 mL with a lining fluid volume corresponding to ca. 5 $\mu L/cm^2$, which may compromise the solubilization and subsequent absorption of poorly soluble molecules such as itraconazole.

The following in vitro dissolution model was used to understand the dissolution properties of itraconazole containing dry powder aerosols. The aerosol particles were collected at well-defined aerosol particle size distribution (APSD) cut-offs using the Next Generation Impactor (NGI) (Copley Scientific, UK), and then the dissolution behavior simulated using model lung fluid.

A UniDose™ (Nanopharm, Newport, United Kingdom) aerosol dose collection system combined with a modified next generation impactor (NGI) was used to uniformly deposit the impactor stage mass (ISM), which is defined as the dose collected on and below stage 2 of a next generation impactor, onto a suitable filter for subsequent dissolution studies in a USP V—Paddle over disk (POD) apparatus.

B. Materials and Methods for the In Vitro Dissolution Study

The materials used in the study are shown in Table 50. The powder formulations, capsules and packaging materials were equilibrated at 22.5±2.5° C. and 30±5% RH. Formulations were encapsulated into size 3 HPMC capsules under the same conditions. The fill weight for the powder preparations was 10 mg. The formulations were aerosolized from capsules in a unit-dose, capsule-based DPI device (RS01, Plastiape, Osnago, Italy).

One capsule of each formulation was aerosolized at 60 L/min (4 L inhaled volume) using the Plastiape RS01 dry powder inhaler (DPI). The aerosol dose was collected in the UniDose system. One milliliter of the suspension formulations was aerosolized into the cNGI at 15 L/min using a Micro Mist™ Nebuliser (Hudson RCI, Temecula, Calif., USA). The UniDose collection system was used to uniformly deposit the whole impactor stage mass (i.e., below stage 2 of an NGI) onto a glass microfiber filter membrane, which can be seen as where the circles (representing particles or droplets) deposit. The filter was placed into a disk cassette and dissolution studies were undertaken using 500 ml PBS pH 7.4+2.0% SDS in a USP Apparatus II POD (Paddle Over Disk, USP V) at 37° C. For all studies, sink conditions were maintained within the vessel. Samples were taken at specified time points and tested for drug content on an Agilent (Santa Clara, Calif., USA) 1260 Infinity series HPLC. Data has been presented as raw cumulative mass and cumulative mass percentage (%) at 240 minutes (mins).

TABLE 50

Formulations tested.

| Formulation | Description of Itraconazole |
| --- | --- |
| XIX | Dry powder formulation (amorphous itraconazole) |
| XI | Nano formulation with Oleic Acid (Wet milling process #1) - Dry Powder Formulation |
| XII | Nano formulation with Polysorbate 80 (Wet milling process #1) - Dry Powder Formulation |
| X | Liquid Nanosuspension Formulation |
| XIII | Nano formulation with Polysorbate 80 (Microfluidics process #1) - Dry Powder Formulation |
| XIV | Nano formulation with Polysorbate 80 (Wet milling process #2) - Dry Powder Formulation |
| XV | Micro formulation with polysorbate 80 (Jet milling process #1) - Dry Powder Formulation |
| IX | Liquid Microsuspension Formulation |
| Pure ITZ | 100% API of Itraconazole as-received from manufacturer |

C. Results of the UniDose POD Dissolution Studies of the Impactor Stage Mass (ISM) of the Formulations.

Figure 14:
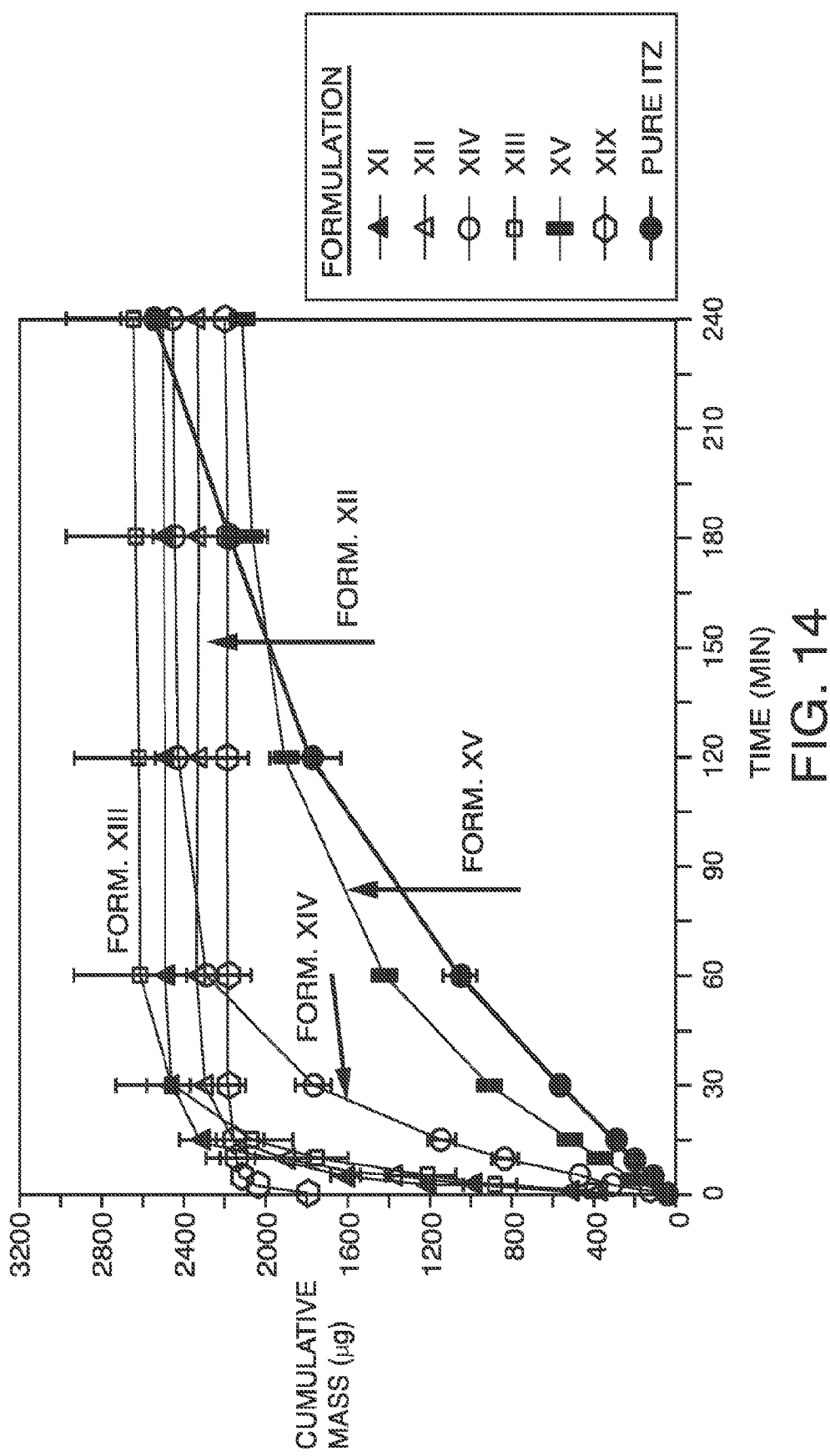
FIG. 14: Cumulative mass dissolution of the ISM collected post-aerosolization of the itraconazole powder formulations from the RS01 at 60 L/min in the UniDose and then POD dissolution testing in a USP Apparatus II set-up.
Figure 15:
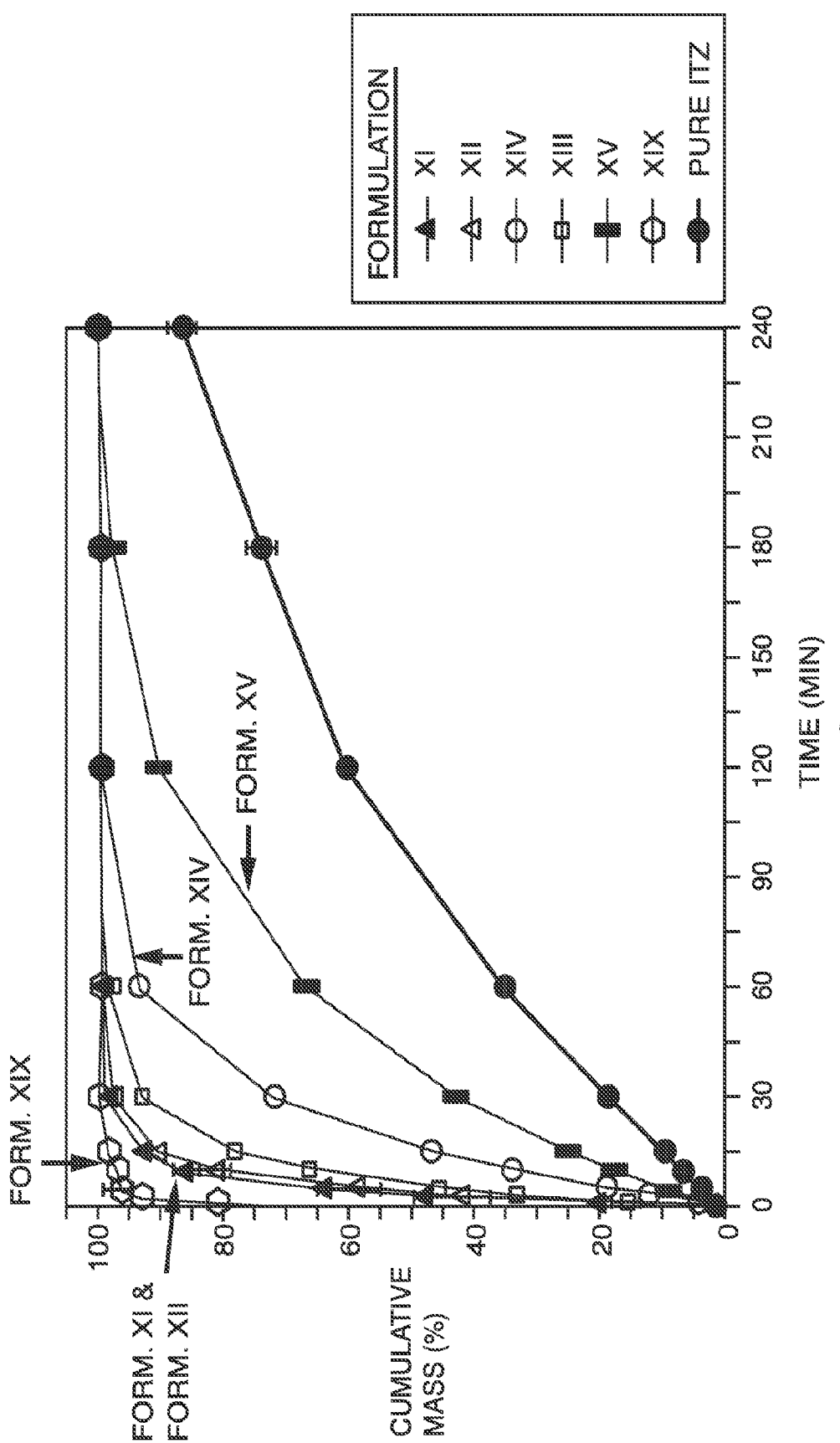
FIG. 15: Cumulative percentage mass dissolution of the ISM collected post-aerosolization of the itraconazole powder formulations from the RS01 at 60 L/min in the UniDose and then POD dissolution testing in a USP Apparatus II set-up.

The raw cumulative mass and percentage cumulative mass dissolution plots of the ISM of formulations are shown in FIGS. 14 and 15, respectively. The UniDose ISM and dissolution half-life of each powder formulation is summarized in Table 50. Particle size of the itraconazole crystal in suspension and the specific surface area (SSA) of the itraconazole crystals estimated using the measured particle size distributions are also shown in Table 51.

Based on the cumulative mass data, the collected ISM of the formulations ranged between 2.1-2.6 mg itraconazole. These data suggested that the aerosolization efficiency of the formulations was approximately 50% based on the nominal dose, since the itraconazole loading in each particle was 50% and the nominal dose was 5 mg of itraconazole (10 mg of powder).

The rate of dissolution of Formulation XIX was the fastest and more than 80% of the drug had dissolved within the first time-point. Due to the rapid dissolution kinetics of formulation XIX it was not possible to calculate the dissolution half-life. The dissolution half-life of the other powder formulations showed the following rank order in their dissolution kinetics:

XI>XII>XIII>XIV>XV>Pure ITZ

Figure 16A:
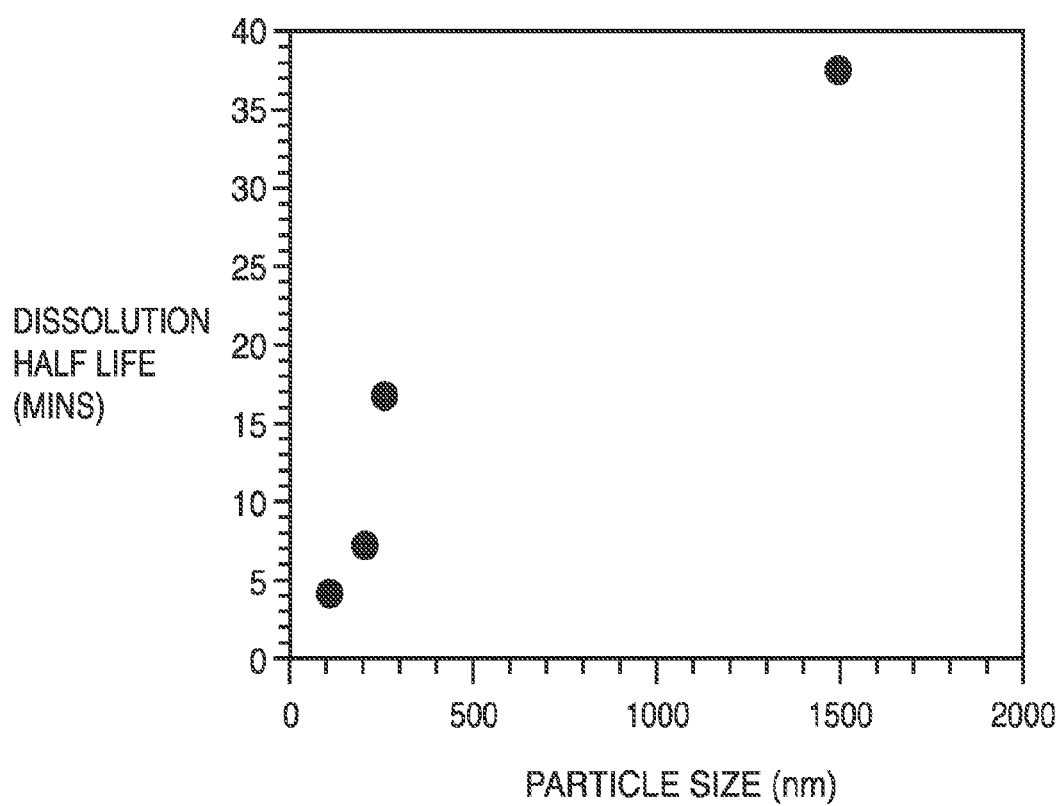
FIG. 16*a*: Relationship between the dissolution half-life and particle size of itraconazole in different powder formulations.
Figure 16B:
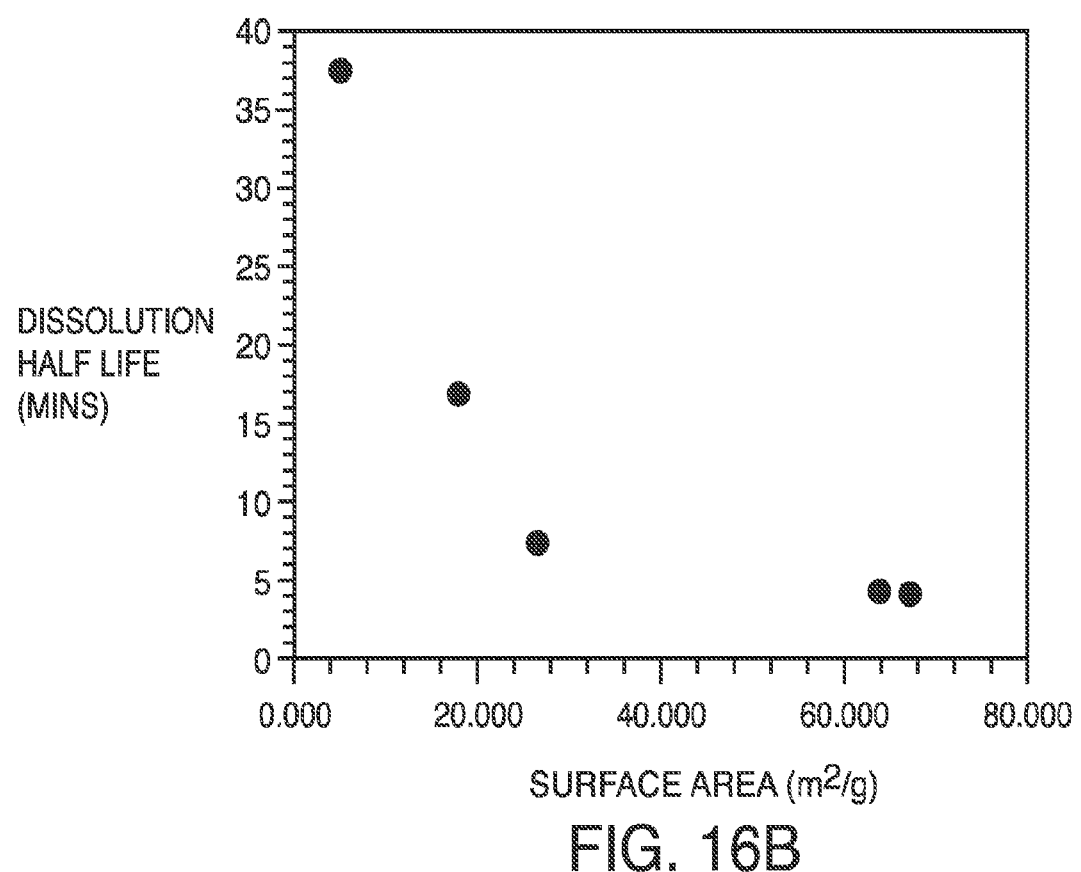
FIG. 16*b*: Relationship between the dissolution half-life and surface area of itraconazole in different powder formulations.

The data shown in FIGS. 14 and 15 was also evaluated for the relationship between the particle size of formulations XI, XII, XIII, XIV, and XV and their respective dissolution half-life, as shown in FIG. 16a. These data suggest a good correlation between the particle size of the itraconazole crystal and the dissolution half-life. FIG. 16b shows the relationship between specific surface area of the itraconazole crystals and dissolution half-life. These data suggest that as the surface area of the particles in the formulation increases that dissolution half-life shortens. These data highlight that that the particle size and thus surface area of the drug substance affects the dissolution behavior of the formulation.

Figure 17:
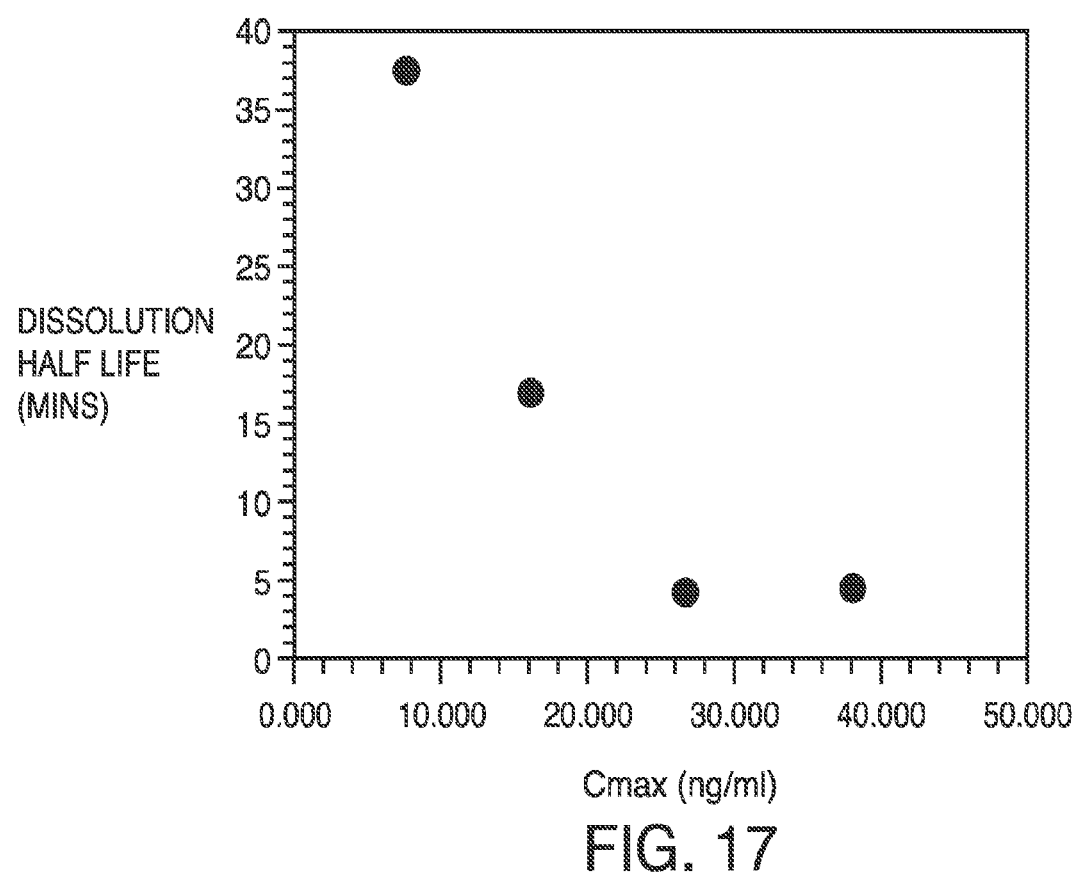
FIG. 17: Relationship between the dissolution half-life and Cmax of itraconazole in different powder formulations.
Figure 18:
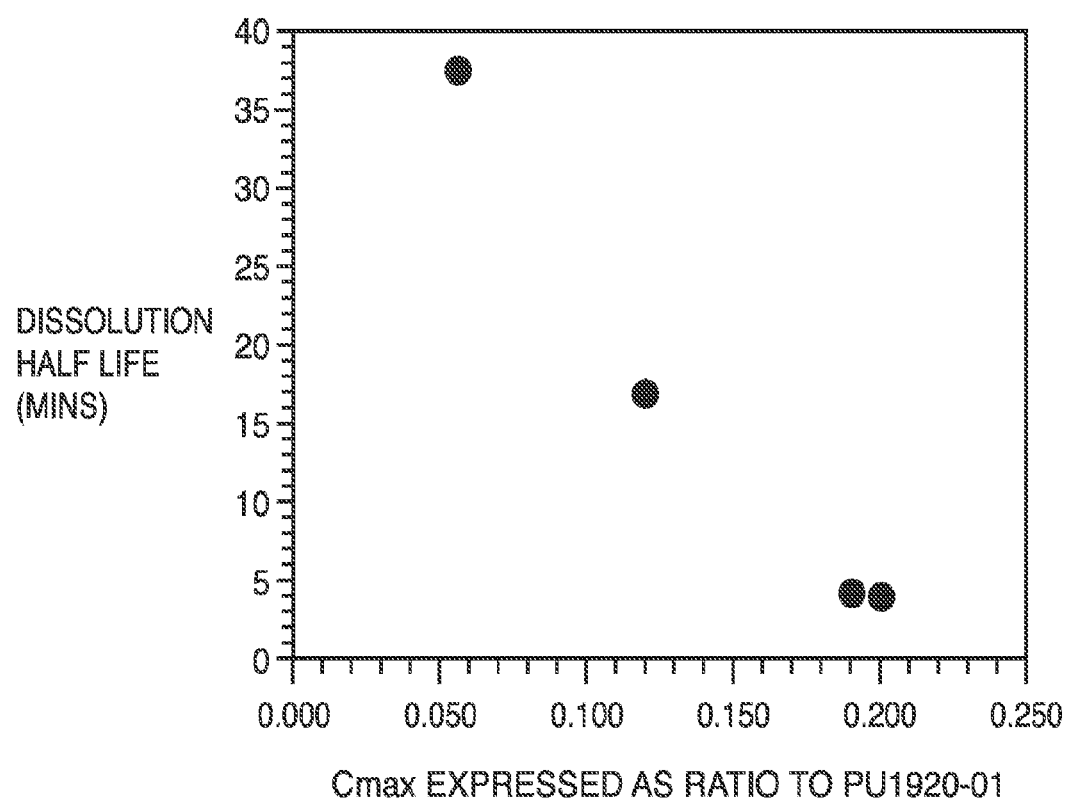
FIG. 18: Relationship between the dissolution half-life and the dose adjusted Cmax of the different powder formulations of itraconazole expressed as a ratio to Formulation XIX.

Based on the pharmacokinetic data shown in Example 14, Formulation XIX had the highest systemic exposure. This correlated with the dissolution data, which suggested that this formulation had rapid dissolution kinetics. The relationship between the dissolution half-life of the other powder formulations and Cmax or Cmax expressed as a ratio of the Cmax response of Formulation XIX are shown in FIGS. 17 and 18, respectively. There was an inverse relationship between the dissolution half-life and Cmax, which suggested that a faster rate of dissolution resulted in higher systemic exposure. The correlation between the Cmax ratio to the systemic response of Formulation XIX with dissolution half-life was stronger. These data suggest that the systemic exposure responses of itraconazole formulations are modulated by their dissolution behavior and in turn the physicochemical properties of the formulations.

TABLE 51

Particle size, UniDose ISM and dissolution half-life of each formulation listed below.

| Formulations | PSD of Itraconazole Crystal (nm) | SSA of Itraconazole Particle (m²/g) | UniDose ISM (mg) | Dissolution Half-Life (mins) |
|---|---|---|---|---|
| XIV | 258 | 18.0 | 2.45 | 16.84 |
| XI | 126 | 67.1 | 2.51 | 4.13 |
| XII | 132 | 64.1 | 2.35 | 4.35 |
| XIII | 198 | 26.6 | 2.65 | 7.39 |
| Pure ITZ | Not Known | Not Known | 2.55 | 101.79 |
| XV | 1600 | 3.86 | 2.12 | 37.53 |
| XIX | Not Applicable | Not Applicable | 2.20 | NA |

Figure 19:
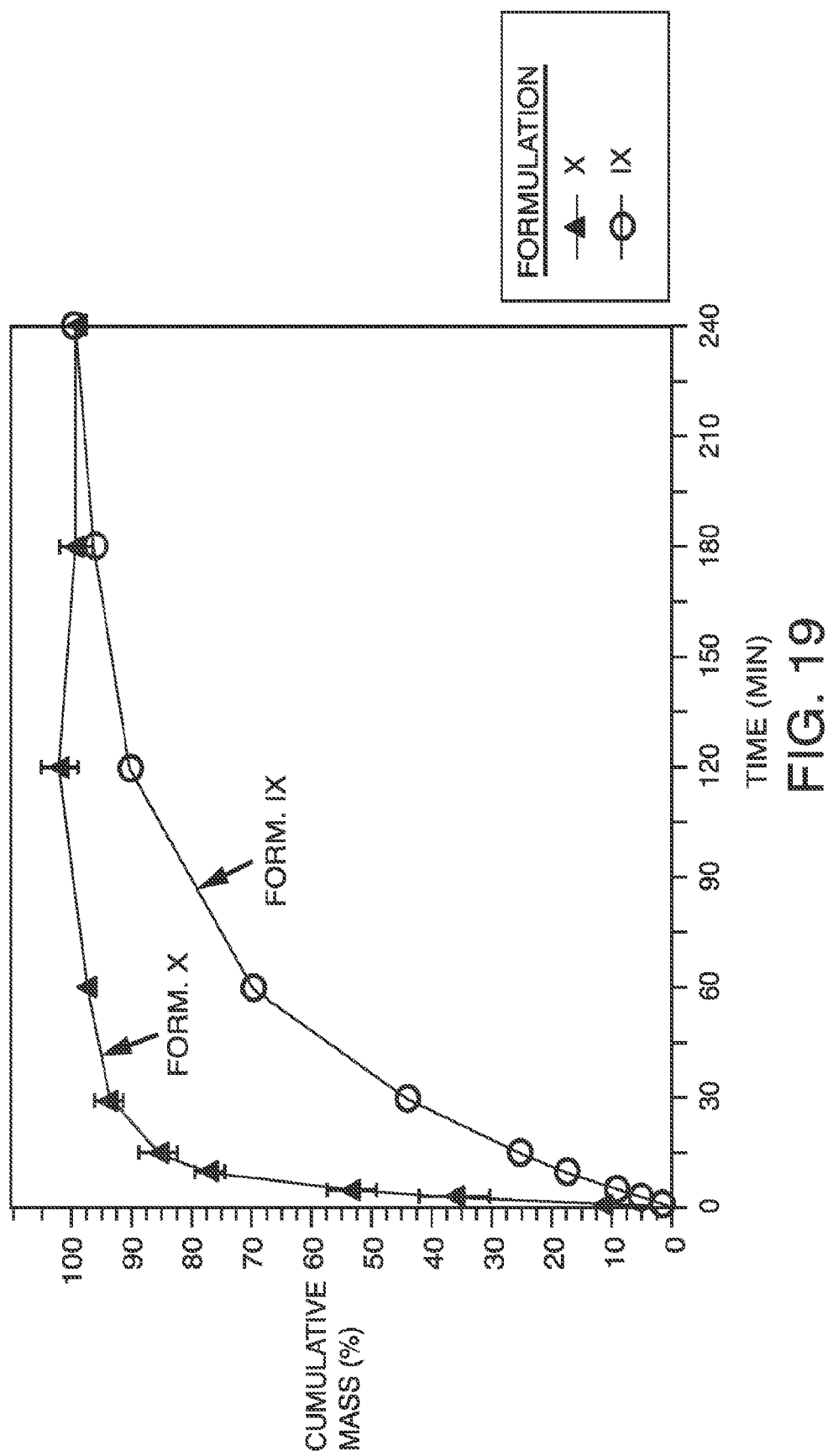
FIG. 19: Cumulative percentage mass dissolution of the ISM collected post-aerosolization of the itraconazole suspension formulations (Formulations XX and XXI) from a Micro Mist nebulizer at 15 L/min in the UniDose and then POD dissolution testing in a USP Apparatus II set-up.

The raw cumulative mass percentage dissolution plots of the ISM of Nano-suspension Formulation and the Micro-suspension Formulation determined by UniDose POD is shown in FIG. 19.

The rate of dissolution of Nano-suspension Formulation was faster than the Micro-suspension Formulation. The dissolution half-life of the Nano-suspension Formulation and the Micro-suspension Formulation were 5.3 and 35.5 mins, respectively.

Example 13. In Vitro Dissolution and Permeability Study of Dry Powder Formulations Containing Crystalline Itraconazole A. In Vitro Dissolution and Permeability Study A bio-relevant dissolution testing system was used based on mimicking the air-liquid interface at the respiratory epithelium interface using a cell-based in vitro method. A modified next generation impactor that incorporated cell culture plates onto collection stages (cNGI) was used to uniformly deposit materials onto the cell cultures. Dissolution and permeation of the drug through the epithelial cell monolayer was measured.

B. Materials and Methods for the In Vitro Dissolution and Permeability Study

Epithelial cell monolayers grown at the air-liquid interface in Snapwell™ (Corning Costar, Mass., USA) permeable insert were integrated into the cNGI. Calu-3 cell line (ATCC, LGC Standards, Teddington, UK) (passage 32-50) were grown in minimum essential medium (MEM) supplemented with non-essential amino acids, 10% (v/v) fetal bovine serum, 1% (v/v) penicillin-streptomycin and 1% (v/v) Fungizone antimycotic and maintained in a humidified atmosphere of 95%/5% Air/$CO_2$, respectively, at 37° C. Cells were seeded on to Snapwell inserts at a density of $5 \times 10^5$ cells.$cm^{-2}$ and cultured under air-interfaced conditions from day 2 in culture for 12 days. The transepithelial electrical resistance (TEER) was measured using an EVOM2 chopstick electrode connected to an EVOM2 Epithelial Voltohmmeter (World Precision Instruments, Hitchin, United Kingdom) and monolayers with a TEER above 450Ω.$cm^2$ were deemed confluent.

Snapwells containing Calu-3 ALI cells were transferred to a modified NGI cup and placed into stage 4 of the NGI (Copley Scientific, Nottingham, UK). A single capsule of the powder formulations was aerosolized into the cNGI at 60 L/min for 4 seconds. One milliliter of the suspension formulations was aerosolized into the cNGI at 15 L/min using a Micro Mist Nebulizer (Hudson RCI, Temecula, Calif., USA).

The materials used in the study are shown in Table 49. The powder formulations, capsules and packaging materials were equilibrated at 22.5±2.5° C. and 30±5% RH. Formulations were encapsulated into size 3 HPMC capsules under the same conditions. The fill weight for the powder preparations was 10 mg. The formulations were aerosolized from capsules in a unit-dose, capsule-based DPI device (RS01, Plastiape, Osnago, Italy). One capsule of each formulation was aerosolized at 60 L/min (4 L inhaled volume) using the Plastiape RS01 dry powder inhaler (DPI).

Post-dosing of the dose on to the Snapwells from stage 4, the Snapwells were transferred to 6-well plates, which contained 2 mL of PBS pH 7.4+2.0% SDS maintained at 37° C. Basolateral samples were taken at different time points and drug content was measured on an Agilent (Santa Clara, Calif., USA) 1260 Infinity series HPLC. Total dose delivered to the cells was measured from the total amount of drug dissolved over the time-course and from lysing cells post experimentation.

Figure 20:
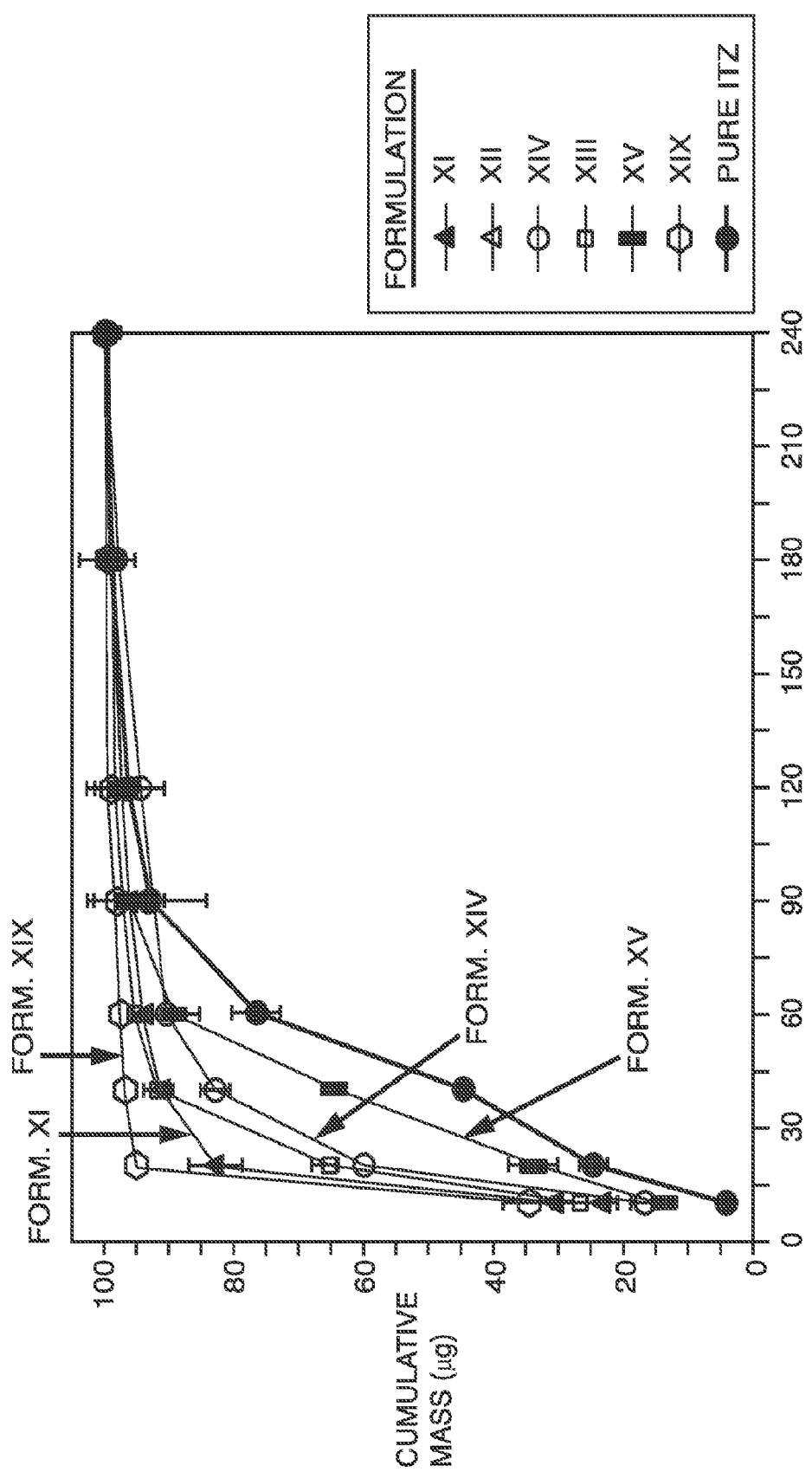
FIG. 20: Cumulative mass percent of the recovered dose from the different powder formulations of itraconazole deposited on stage 4 of the cNGI.

C. Results of the cNGI Integrated Dissolution and Permeability Studies of Powder Formulations of Itraconazole The cumulative mass percent (%) of the total recovered dose plots of the powder formulations of itraconazole delivered to the cells on stage 4 are shown in FIG. 20. These data suggested differences between the dissolution and permeability kinetics of the different formulations. The as-received Pure ITZ had slower dissolution and permeability kinetics than the other formulations, whilst Formulation XIX had the fastest dissolution and permeability kinetics.

To understand the cNGI data for the different formulations, we utilised the data to calculate the rate of diffusion of the drug substance by taking into consideration loaded dose differences. This was done using the following equation:

$$\text{Rate of Diffusion} = \frac{J}{AC_0}$$

where J is the flux (gradient of the cNGI dissolution/permeability profile), A is the area of the barrier and $C_0$ is the loaded dose. These data are summarised in Table 52, which shows that the rate of diffusion for the formulations followed the rank order:

XIX>XI>XII>XIII>XIV>XV>Pure ITZ

TABLE 52

Particle size and rate of diffusion of each powder formulation below.

| Formulations | PSD of Itraconazole Crystal (nm) | Rate of Diffusion (cm/s) |
| --- | --- | --- |
| XI | 126 | 6.11 |
| XII | 132 | 4.88 |
| XIII | 198 | 4.82 |
| Pure ITZ | Not Known | 1.81 |
| XV | 1600 | 2.52 |
| XIX | Not Known | 7.01 |

Figure 21:
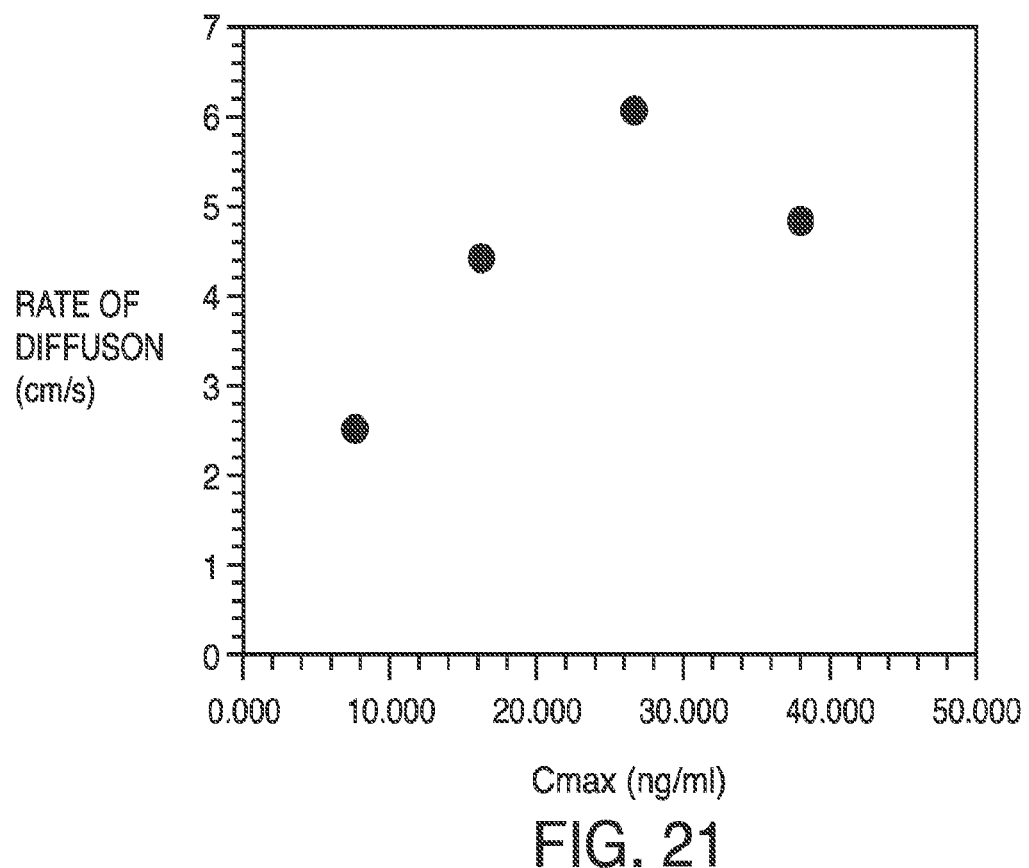
FIG. 21: Relationship between the dissolution half-life and Cmax of itraconazole in different powder formulations.
Figure 22:
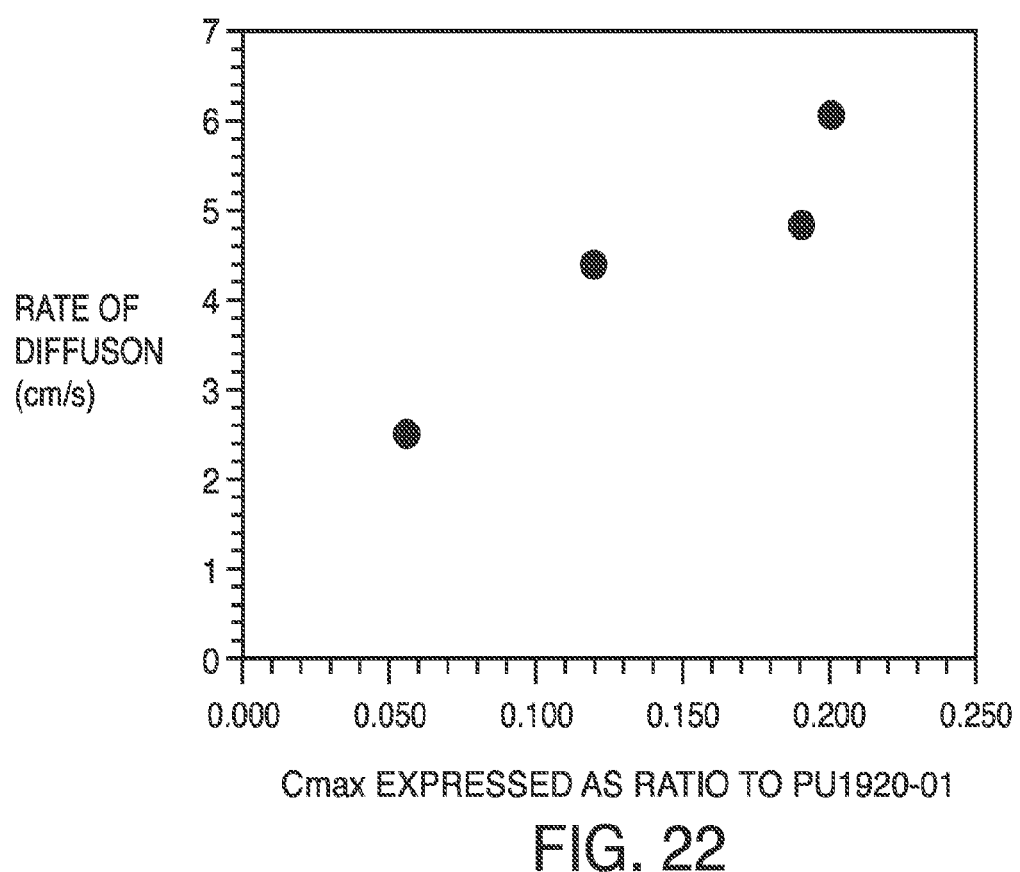
FIG. 22: Relationship between the rate of diffusion and the dose adjusted Cmax of the different powder formulations of itraconazole expressed as a ratio to Formulation XIX.

Based on the pharmacokinetic data shown in Example 14, Formulation XIX had the highest systemic exposure. This correlated with the rate of diffusion of this formulation, which suggested that this formulation had rapid dissolution and permeation kinetics. The relationship between the rate of diffusion of the other powder formulations and Cmax or Cmax expressed as a ratio of the Cmax response of Formulation XIX are shown in FIGS. 21 and 22, respectively. There was a relationship between the rate of diffusion and Cmax, which suggested that a faster rate of diffusion resulted in higher systemic exposure. The correlation between the Cmax ratio to the systemic response of Formulation XIX with the rate of diffusion was stronger.

Figure 23:
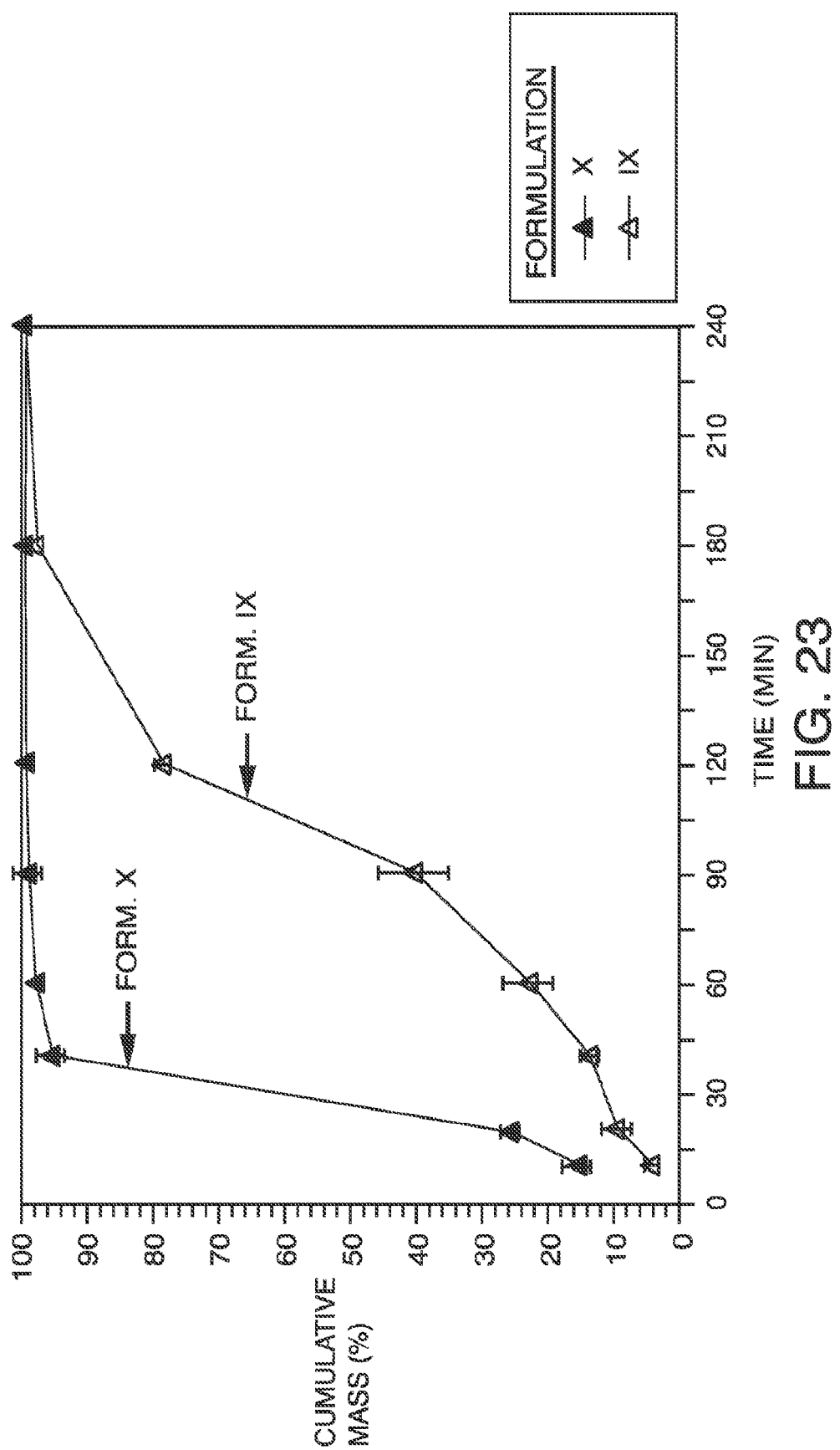
FIG. 23: Cumulative mass percent of the recovered dose from the nebulized suspension formulations of itraconazole (Formulations XX and XXI) deposited on stage 4 of the cNGI.

The raw cumulative mass percentage dissolution plots of the ISM of Nano-suspension Formulation and the Micron-suspension Formulation determined by cNGI is shown in FIG. 23. The cNGI data suggests that the rate of diffusion of the Nano-suspension Formulation was faster than the Micron-suspension Formulation.

Example 14. Single Dose Inhalation PK Study in Rats

A. Materials and Methods

Blood and lung tissue samples were taken from rats following a single inhalation administration of each of five different itraconazole formulations over a 60-minute exposure period in order to assess the systemic exposure of male rats to itraconazole and its metabolite, hydroxy-itraconazole, at a nominal dose level of 5 mg/kg. Plasma concentrations of itraconazole and hydroxy-itraconazole in samples taken at the end of the exposure period, and up to 96 hours after the end of exposure were measured by validated LC-MS/MS methods.

B. Results—Plasma

Maximum mean plasma concentrations ($C_{max}$) of itraconazole and the areas under the mean plasma concentration-time curves estimated up to the time of the last quantifiable sample ($AUC_{last}$) are summarized in Table 53.

TABLE 53

Plasma $C_{max}$ and $AUC_{last}$

| | Itraconazole | | Hydroxy-itraconazole | |
| --- | --- | --- | --- | --- |
| Formulation | $C_{max}$ (ng/mL) | $AUC_{last}$ (ng · h/mL) | $C_{max}$ (ng/mL) | $AUC_{last}$ (ng · h/mL) |
| XIX | 123 | 1170 | 231 | 4950 |
| XII | 38.1 | 921 | 95.1 | 3550 |
| XI | 26.7 | 529 | 101 | 2770 |
| XIV | 16.2 | 353 | 56.2 | 1630 |
| XV | 7.65 | 157 | 38.5 | 1390 |

The ratios of the maximum mean plasma concentrations ($C_{max}$) and areas under the mean plasma concentration-time curves ($AUC_{last}$) in each group relative to the $C_{max}$ and $AUC_{last}$ values for the group receiving Formulation XIX, based on $C_{max}$ and $AUC_{last}$ values corrected for the differences in the doses received, are presented in Table 54.

TABLE 54

Plasma $C_{max}$ and $AUC_{last}$, both relative to Formulation XIX.

| | Itraconazole | | Hydroxy-itraconazole | |
| --- | --- | --- | --- | --- |
| Formulation | $C_{max}$ (ng/mL) | $AUC_{last}$ (ng · h/mL) | $C_{max}$ (ng/mL) | $AUC_{last}$ (ng · h/mL) |
| XIX | 1 | 1 | 1 | 1 |
| XII | 0.19 | 0.49 | 0.25 | 0.44 |
| XI | 0.20 | 0.42 | 0.41 | 0.52 |
| XIV | 0.12 | 0.28 | 0.23 | 0.31 |
| XV | 0.056 | 0.12 | 0.15 | 0.25 |

The rate ($C_{max}$) and extent ($AUC_{last}$) of systemic exposure of rats to itraconazole were highest following exposure to Formulation XIX. $C_{max}$ and $AUC_{last}$ were similar following exposure to Formulation XII and Formulation XI and were slightly lower following exposure to Formulation XIV. $C_{max}$ and $AUC_{last}$ were lowest following exposure to Formulation XV. A similar pattern was observed for the rate and extent of systemic exposure to hydroxy-itraconazole, although $C_{max}$ and $AUC_{last}$ values following exposure to Formulation XII were lower than those following exposure to Formulation XI and slightly higher than following exposure to Formulation XIV.

C. Results—Lung Tissue

Maximum mean lung tissue concentrations ($C_{max}$) of itraconazole and the areas under the mean lung tissue concentration-time curves estimated up to the time of the last quantifiable sample ($AUC_{last}$) are summarized in Table 55.

TABLE 55

Lung Tissue $C_{max}$ and $AUC_{last}$

| | Itraconazole | | Hydroxy-itraconazole | |
| --- | --- | --- | --- | --- |
| Formulation | $C_{max}$ (ng/g) | $AUC_{last}$ (ng · h/g) | $C_{max}$ (ng/g) | $AUC_{last}$ (ng · h/g) |
| XIX | 23600 | 86900 | 733 | 13400 |
| XII | 91300 | 2400000 | 260 | 10100 |
| XI | 66800 | 1090000 | 285 | 6720 |
| XIV | 53500 | 1810000 | 144 | 3970 |
| XV | 36400 | 1600000 | 114 | 3310 |

The ratios of the maximum mean lung tissue concentrations ($C_{max}$) and areas under the mean lung tissue concentration-time curves ($AUC_{last}$) in each group relative to the $C_{max}$ and $AUC_{last}$ values for the group receiving Formulation XIX, based on $C_{max}$ and $AUC_{last}$ values corrected for the differences in the doses received, are presented in Table 56.

TABLE 56

Lung Tissue $C_{max}$ and $AUC_{last}$ both relative to Formulation XIX.

| Formulation | Itraconazole | | Hydroxy-itraconazole | |
| --- | --- | --- | --- | --- |
| | $C_{max}$ ratio | $AUC_{last}$ ratio | $C_{max}$ ratio | $AUC_{last}$ ratio |
| XIX | 1 | 1 | 1 | 1 |
| XII | 2.4 | 17.0 | 0.22 | 0.46 |
| XI | 2.6 | 11.7 | 0.36 | 0.47 |
| XIV | 2.6 | 19.4 | 0.36 | 0.28 |
| XV | 1.4 | 16.5 | 0.14 | 0.22 |

The rate ($C_{max}$) and extent ($AUC_{last}$) of local exposure of the lungs of rats to itraconazole were lowest following exposure to Formulation XIX. $C_{max}$ and $AUC_{last}$ were generally similar following exposure to Formulation XII, Formulation XI and Formulation XIV, although $AUC_{last}$ following exposure to Formulation XII was somewhat lower than that following exposure to the other two formulations. Following exposure to Formulation XV, $C_{max}$ was only slightly higher than that following exposure to Formulation XIX and was lower than the values for the other formulations, while $AUC_{last}$ was higher than that following exposure to Formulation XIX and was broadly similar to that following exposure to the other formulations. The $C_{max}$ and $AUC_{last}$ values for hydroxy-itraconazole were highest following exposure to Formulation XIX, and were lower following exposure to Formulation XII, Formulation XI, Formulation XIV and Formulation XV, but were broadly similar for all four of these formulations.

The ratios of the $AUC_{last}$ values in lung to those the corresponding values in plasma are presented in Table 57.

TABLE 57

Ratios of $AUC_{last}$ for lung tissue to plasma tissue

| | Lung tissue:plasma ratio | |
| --- | --- | --- |
| Formulation | Itraconazole | Hydroxy-itraconazole |
| XIX | 74 | 2.7 |
| XII | 2600 | 2.8 |
| XI | 2100 | 2.4 |
| XIV | 5100 | 2.4 |
| XV | 10000 | 2.4 |

The lung tissue:plasma ratios for itraconazole were lowest following exposure to Formulation XIX, were similar following exposure to Formulation XII and Formulation XI and were somewhat higher following exposure to Formulation XIV. The highest ratio was observed following exposure to Formulation XV. The lung tissue:plasma ratios for hydroxy-itraconazole were similar following exposure to each formulation and were much lower than the ratios observed for itraconazole.

Conclusions

The systemic exposure of rats to itraconzole was highest following administration of Formulation XIX. Systemic exposure was similar following inhalation administration of Formulation XII and Formulation XI and was slightly lower following administration of Formulation XIV. Systemic exposure was lowest following administration of Formulation XV. A similar pattern was observed for systemic exposure to hydroxy-itraconazole, systemic exposure following administration of Formulation XII was lower than that following administration of Formulation XI and slightly higher than that following administration of Formulation XIV.

The local exposure of the lungs of rats to itraconzole was lowest following exposure to Formulation XIX. Local exposure was generally similar following administration of Formulation XII, Formulation XI and Formulation XIV. Following administration of Formulation XV, the maximum concentrations were only slightly higher than those following administration of Formulation XIX and were lower than the values for the other formulations, while $AUC_{last}$ values were higher than that following exposure to Formulation XIX and were broadly similar to those following exposure to the other formulations. Local exposure to hydroxy-itraconazole was highest following administration of Formulation XIX, and was lower following administration of Formulation XII, Formulation XI, Formulation XIV and Formulation XV, but was broadly similar for all four of these formulations.

Example 15. Dry Powder Formulations of Amorphous Itraconazole Prepared for Use in 28-Day Toxicity Studies A. Powder Preparation.

A feedstock solution utilizing a water-tetrahydrofuran (THF) co-solvent system was prepared and used to manufacture a dry powder composed of itraconazole, sodium sulfate and leucine. A drug load of 50 wt % itraconazole, on a dry basis, was targeted. The feedstock solution that was used to spray dry particles was made as follows. The required quantity of water was weighed into a suitably sized glass vessel. The excipients were added to the water and the solution allowed to stir until visually clear. The required amount of THF was weighed into a suitably sized glass vessel. The itraconazole was added to the THF and the solution allowed to stir until visually clear. The itraconazole-containing THF solution was then added to the excipient solution and stirred until visually homogenous. The feedstock was then spray-dried. The individual feedstock volume was 9.5625 L. Fourteen of these feedstocks were prepared for a total of 133.875 L which supported a manufacturing campaign of approximately 30 hours. Table 58 lists the components of each feedstock used in preparation of the dry powder.

TABLE 58

Feedstock composition

| Formulation | Water (g) | Tetrahydrofuran (g) | Itraconazole (g) | Sodium sulfate (g) | Leucine (g) | Total mass (gm) |
| --- | --- | --- | --- | --- | --- | --- |
| XX | 4295.379 | 4676.636 | 57.375 | 40.163 | 17.213 | 9086.766 |

A dry powder of Formulation XX was manufactured from this feedstock by spray drying on the Niro Mobile Minor spray dryer (GEA Process Engineering Inc., Columbia, Md.) with bag filter collection. The system was run in open-loop (single pass) mode using nitrogen as the drying and atomization gas. Atomization of the liquid feed utilized a Niro atomizer with a 1.0 mm liquid insert. The aspirator of the system was adjusted to maintain the system pressure at −2.0" water column.

The following spray drying conditions were followed to manufacture the dry powder. For Formulation XX, the liquid feedstock solids concentration was 12 g/L, the process gas inlet temperature was 120° C. to 140° C., the process gas outlet temperature was 40° C., the drying gas flowrate was 80 kg/hr, the atomization gas flowrate was 352.2 g/min, the atomization gas backpressure at the atomizer inlet was 45 psig to 57 psig and the liquid feedstock flowrate was 75 mL/min. The resulting dry powder formulation is reported in Table 59. The itraconazole in the formulation was amorphous.

TABLE 59

Dry powder composition, dry basis

| Formulation | Dry Powder Composition (w/w), dry basis |
|---|---|
| XX | 50% itraconazole, 35% sodium sulfate, 15% leucine |

B. Powder Characterization.

The bulk particle size characteristics for the formulation are found in Table 60. The span at 1 bar of 1.83 for Formulation XX, indicates a relatively narrow size distribution. The 1 bar/4 bar dispersibility ratio of 1.06 for Formulation XX, indicates the particle size is relatively independent of dispersion energy, a desirable characteristic which allows similar dispersion across a range of dispersion energies.

TABLE 60

Bulk particle size

| | 0.5 bar | | 1 bar | | 4 bar | | 1 bar:4 bar |
|---|---|---|---|---|---|---|---|
| Formulation | Dv[50] (µm) | Span | Dv[50] (µm) | Span | Dv[50] (µm) | Span | Dv[50] ratio |
| XX | 1.84 | 1.83 | 1.58 | 1.81 | 1.50 | 1.82 | 1.06 |

The weight loss of Formulation XX was measured via TGA and was found to be 0.34%.

The itraconazole content of Formulation XX was measured with HPLC-UV and is 100.9% of nominal.

Example 16. Dry Powder Formulations of Crystalline Itraconazole Prepared for Use in 28-Day Toxicity Studies A. Powder Preparation.

The nanocrystalline itraconazole for Formulation XXI was prepared as a suspension comprising 25 wt % itraconazole (SMS Pharma lot ITZ-0715005) and 2.5 wt % polysorbate. The polysorbate 80 was dissolved in 72.5% deionized water via magnetic stir bar, then the itraconazole was added and suspensded by stirring with a magenetic stir bar. Once all of the itraconazole was suspended, the formulation was processed on the Netzsch MiniCer using 0.2 mm grinding media (TOSOH, Tokyo, Japan) with 90% chamber fill. The following conditions were used to manufacture the itraconazole suspension. The mill speed was 3000 RPM, the inlet pump speed was 100 RPM, the recirculating chiller was 10° C., the inlet air pressure was 4.5 bar, and run time was 30-40 minutes. Eight suspensions were processed this way and combined to make the final suspension lot. The final median particle size (Dv(50)) of the milled suspension was 130 nm.

The nanocrystalline itraconazole for Formulation XXII was prepared as a suspension comprising 10 wt % itraconazole and 0.7 wt % oleic acid, 1.5% ammonium hydroxide in deionized water. The oleic acid was dissolved in 87.8 deionized water via magnetic stir bar and then the ammonium hydroxide was added and dissolved via magnetic stir bar. Finally, the itraconazole was added and mixed with a magnetic stir bar to form a suspension. Once all of the itraconazole was suspended, the formulation was processed on the Netzsch MiniCer using 0.5 mm grinding media (TOSOH, Tokyo, Japan) with 90% chamber fill. The following conditions were used to manufacture the itraconazole suspension. The mill speed was 3000 RPM, the inlet pump speed was 100 RPM, the recirculating chiller was 10° C., the inlet air pressure was 4.5 bar, and run time was 200-240 minutes. Eight suspensions were processed this way and combined to make the final suspension lot. The final median particle size (Dv(50)) of the milled suspension was 115 nm.

The microcrystalline itraconazole for Formulation XXIII was prepared using a Qualification Micronizer jet mill (Sturtevant, Hanover, Mass. USA). The feed pressure was set to 85 psig and the grind pressure was set to 45 psig. Itraconazole was continuously fed into the mill until 480.0 g of itraconazole was milled. The final median particle size (Dv(50)) of the milled API was 1640 nm. The micronized itraconazole for Formulation XXIII was then compounded into a suspension consisting of 10 wt % itraconazole and 0.25 wt % polysorbate 80 in deionized water. The batch size was 4800 g. The polysorbate 80 was dissolved in 88.75% deionized water via magnetic stir bar, then the itraconazole was slowly added and allowed to mix until the suspension was observed to be visually dispersed and homogeneous.

Feedstock suspensions were prepared and used to manufacture dry powders composed of crystalline itraconazole, and other additional excipients. A drug load of 50 wt % itraconazole, on a dry basis, was targeted. The feedstock suspensions that were used to spray dry particles were made as follows. The required quantity of water was weighed into a suitably sized glass vessel. The excipients were added to the water and the solution was allowed to stir until visually clear. The itraconazole-containing suspension was then added to the excipient solution and stirred until visually homogenous. The feedstocks were then spray-dried. Feedstocks were stirred while spray dried. The individual feedstock masses for Formulation XXI were 7.5 kg each. Six of these feedstocks were spray dried, which supported a manufacturing campaign of fifteen hours. The individual feedstock masses for Formulation XXII were 6.0 kg each. Three of these feedstocks were spray dried, which supported a manufacturing campaign of six hours. The individual feedstock masses for Formulation XXIII were 8.0 kg each. Four of these feedstocks were spray dried, which supported a manufactured campaign of approximately 11 hours. Table 61 lists the components of the feedstocks used in preparation of the dry powders.

TABLE 61

Feedstock compositions for formulations containing polysorbate 80

| Formulation | Water (g) | Itraconazole (g) | Polysorbate 80 (g) | Sodium sulfate (g) | Leucine (g) | Total mass (gm) |
|---|---|---|---|---|---|---|
| XXI | 7275.0 | 112.5 | 11.25 | 78.75 | 22.5 | 7500.0 |
| XXIII | 7904.0 | 48.0 | 1.2 | 33.6 | 13.2 | 8000.0 |

TABLE 62

Feedstock compositions for formulations containing oleic acid

| Formulation | Water (g) | Itraconazole (g) | Oleic acid (g) | Ammonium hydroxide (g) | Sodium sulfate (g) | Leucine (g) | Total mass (gm) |
|---|---|---|---|---|---|---|---|
| XXII | 5806.74 | 90.00 | 6.18 | 13.38 | 63.00 | 20.82 | 6000.12 |

Dry powders of Formulations XXI-XXIII were manufactured from these feedstocks by spray drying on the Niro Mobile Minor spray dryer (GEA Process Engineering Inc., Columbia, Md.) with bag filter collection. The system was run in open-loop (single pass) mode using nitrogen as the drying and atomization gas. Atomization of the liquid feed utilized a Niro two fluid nozzle atomizer with a 1.0 mm liquid insert. The aspirator of the system was adjusted to maintain the system pressure at −2.0" water column.

The following spray drying conditions were followed to manufacture the dry powders. For Formulations XXI and XXII, the liquid feedstock solids concentration was 3%, the process gas inlet temperature was 170° C. to 190° C., the process gas outlet temperature was 65° C., the drying gas flowrate was 80.0 kg/hr, the atomization gas flowrate was 250.0 g/min, and the liquid feedstock flowrate was 50.0 g/min. The resulting dry powder formulations are reported in Table 64. For Formulation XXIII, the liquid feedstock solids concentration was 1.2%, the process gas inlet temperature was 170-190° C., the process gas outlet temperature was 65° C., the drying gas flowrate was 80.0 kg/hr, the atomization gas flowrate was 250.0 g/min, and the liquid feedstock flowrate was 50.0 g/min. The resulting dry powder formulation is reported in Table 63.

TABLE 63

Dry powder composition, dry basis

| Formulation | Description | Dry Powder Composition (w/w), dry basis |
|---|---|---|
| XXI | Nanocrsytalline, PS 80 stabilizer | 50% Itraconazole, 35% sodium sulfate, 15% leucine, 5.0% polysorbate 80 |
| XXII | Nanocrystalline, oleic acid stabilizer | 50% itraconazole, 35% sodium sulfate, 11.57% leucine, 3.43% oleic acid |
| XXIII | Microcrystalline, PS80 stabilizer | 50% itraconazole, 35% sodium sulfate, 13.75% leucine, 1.25% polysorbate 80 |

B. Powder Characterization.

The bulk particle size characteristics for the three formulations are found in Table 64. The span at 1 bar of less than 2.05 for Formulations XXI-XXIII indicates a relatively narrow size distribution. The 1 bar/4 bar dispersibility ratio less than 1.25 for Formulations XXI-XXIII indicate that they are relatively independent of dispersion energy, a desirable characteristic which allows similar particle dispersion across a range of dispersion energies.

TABLE 64

Bulk particle size

| | 0.5 bar | | 1 bar | | 4 bar | | 1 bar:4 bar |
|---|---|---|---|---|---|---|---|
| Formulation | Dv[50] (μm) | Span | Dv[50] (μm) | Span | Dv[50] (μm) | Span | Dv[50] ratio |
| XXI | 2.35 | 1.86 | 2.10 | 1.97 | 1.94 | 2.10 | 1.08 |
| XXII | 2.33 | 1.90 | 2.13 | 2.01 | 2.00 | 2.07 | 1.07 |
| XXIII | 2.15 | 1.82 | 2.03 | 1.88 | 1.89 | 1.88 | 1.08 |

The weight loss of Formulations XXII-XXIII were measured via TGA and are detailed in Table 65.

TABLE 65

Weight loss (%) via TGA

| Formulation | Weight loss via TGA (%) |
|---|---|
| XXI | 0.45 |
| XXII | 0.32 |
| XXIII | 0.37 |

The itraconazole content of Formulations XXI-XXIII were measured with HPLC-UV and are detailed in Table 66.

TABLE 66

Itraconazole content

| Formulation | Itraconazole content (% label claim) |
|---|---|
| XXI | 98.50 |
| XXII | 100.50 |
| XXIII | 101.20 |

Example 17. 28-Day Inhalation Toxicity Studies A and B in Rats

A. Materials and Methods

In order to assess both the plasma and lung pharmacokinetics as well as the potential for local tissue toxicity, two separate 28-day studies were performed. In the first study, 28-Day Study A, 5 groups of animals were dosed daily for 28 days with either air or placebo controls or one of three doses of Formulation XX. In the second study, 28-Day Study B, 7 groups of rats were dosed with one of three formulations of crystalline nanoparticulate itraconazole, daily for 28 days, or in the case of one group, every three days. Groups and achieved doses are detailed in Tables 67 and 68.

TABLE 67

Dose Groups in 28-Day Study A

| Group No. | Formulation | Achieved Total Delivered API Dose Level (mg/kg) |
|---|---|---|
| 1 | Air Control | 0 |
| 2 | Placebo Control | 0 |
| 3 | XX | 5.8 |
| 4 | XX | 22 |
| 5 | XX | 49 |

TABLE 68

Dose Groups in 28-Day Study B

| Group No. | Formulation | Achieved Total Delivered API Dose Level (mg/kg) |
|---|---|---|
| 1 | XXI | 5.2 |
| 2 | XXI | 14.8 |
| 3 | XXI | 38.3 |
| 4 | XXI x3 days | 14.8 |
| 5 | XXIII | 5.0 |
| 6 | XXIII | 14.5 |
| 7 | XXII | 14.7 |

In both studies, blood and lung tissue samples were taken from rats following the first and last inhalation administration of each formulations in order to assess the lung and systemic exposure and accumulation of itraconazole in male and female rats. In addition, pulmonary tissue samples, including the larynx, trachea, tracheal bifurcation (carina) and lungs, were collected from all animals 24 hours after the last dose in order to assess microscopic pathology changes resulting from the dosing. Plasma and lung concentrations of itraconazole in samples were measured by validated LC-MS/MS methods.

B. Results—Plasma

Maximum mean plasma concentrations ($C_{max}$) of itraconazole and the areas under the mean plasma concentration-time curves estimated up to the time of the last quantifiable sample ($AUC_{0-last}$) on Days 1 and 28 in male and female rats from 28-Day Study A, with amorphous itraconazole, are summarized in Table 69 and from 28-Day Study B, with crystalline itraconazole, are summarized in Table 70.

TABLE 69

Plasma $C_{max}$ and $AUC_{0-last}$ for Itraconazole

| Formulation | Dose level (mg/kg/day) | $C_{max}$ (ng/mL) Day 1 Males | Females | Day 28 Males | Females | $AUC_{0-Tlast}$ (ng·h/mL) Day 1 Males | Females | Day 28 Males | Females |
|---|---|---|---|---|---|---|---|---|---|
| XX | 5.8 | 188 | 283 | 117 | 430 | 1100 | 3840 | 914 | 6310 |
| XX | 22.0 | 348 | 620 | 335 | 1310 | 2710 | 11200 | 2110 | 22200 |
| XX | 49.0 | 510 | 928 | 602 | 2270 | 4990 | 17800 | 3800 | 35200 |

TABLE 70

Plasma $C_{max}$ and $AUC_{0-last}$ for Itraconazole

| Formulation | Dose level (mg/kg/day) | $C_{max}$ (ng/mL) Day 1 Males | Females | Day 28 Males | Females | $AUC_{0-Tlast}$ (ng·h/mL) Day 1 Males | Females | Day 28 Males | Females |
|---|---|---|---|---|---|---|---|---|---|
| XXI | 5.2 | 17.1 | 56.4 | 25.6 | 299 | 263 | 1080 | 376 | 5600 |
| XXI | 14.8 | 32.9 | 119 | 90.4 | 726 | 471 | 2310 | 1540 | 12700 |
| XXI | 38.3 | 110 | 292 | 261 | 1290 | 2020 | 4660 | 5260 | 23900 |
| XXI* | 14.8 | 49.0 | 36.3 | 317 | 339 | 785 | 718 | 2830 | 4920 |
| XXIII | 5.0 | 13.8 | 28.3 | 98.1 | 247 | 204 | 514 | 1020 | 5020 |
| XXIII | 14.5 | 39.6 | 134 | 110 | 550 | 473 | 2390 | 2140 | 11000 |
| XXII | 14.7 | 39.1 | 76.9 | 164 | 526 | 560 | 1330 | 2900 | 11700 |

*Dosed every three days

Despite differences in the absolute achieved doses between the various formulations, it is clear that the peak ($C_{max}$) and total ($AUC_{0-last}$) systemic exposure for PUR1920 is higher than that for any of the crystalline formulations, both after a single dose (Day 1) and repeat dosing (Day 28). Table 71 below summarizes the dose-normalized average C. and $AUC_{0-last}$ for itraconazole for each of the formulations from both 28-day studies using the target dose of 15 mg/kg/day from each study. Normalization was achieved by dividing the exposures measured by the actual achieved dose for each study on each day.

TABLE 71

Dose-normalized plasma $C_{max}$ and $AUC_{0\text{-}last}$ for each of the crystalline formulations.

| | Day 1 | | | | Day 28 | | | |
|---|---|---|---|---|---|---|---|---|
| | $C_{max}$ (ng/mL/) | | $AUC_{0\text{-}last}$ (ng · h/mL) | | $C_{max}$ (ng/mL) | | $AUC_{0\text{-}last}$ (ng · h/mL) | |
| Formulation | M | F | M | F | M | F | M | F |
| XX | 17.40 | 28.18 | 135.50 | 509.09 | 18.61 | 68.95 | 117.22 | 1168.42 |
| XXI | 2.51 | 8.62 | 35.95 | 167.39 | 6.19 | 46.54 | 105.48 | 814.10 |
| XXI x3days | 3.77 | 2.65 | 60.38 | 52.41 | 20.58 | 20.42 | 183.77 | 296.39 |
| XXIII | 1.96 | 5.08 | 28.15 | 134.27 | 7.68 | 43.47 | 138.06 | 658.68 |
| XXII | 2.72 | 5.03 | 38.89 | 86.93 | 10.51 | 31.69 | 185.90 | 704.82 |

The dose normalized $C_{max}$ and $AUC_{0\text{-}last}$ for itraconazole systemic exposure in rats on Day 1 were highest following exposure to Formulation XX. By Day 28, Formulation XX still generally showed higher dose normalized $C_{max}$ and $AUC_{0\text{-}last}$ relative to the crystalline formulation XXI, particularly in females, though the difference was less pronounced with a slightly higher value for $AUC_{0\text{-}last}$ in males for some formulations. These data demonstrate that, for a given achieved delivered lung dose, the systemic exposure that results from inhalation of crystalline formulations is generally less than that for Formulation XX. However, given that the systemic exposure is dependent upon both dissolution rate of the material in the lung and the permeability of the lung tissue, it also demonstrates that, over time, the crystalline formulations do show adequate dissolution and permeation of the tissue to narrow or abolish the difference providing confidence that the crystalline formulations are not simply insoluble deposits in the lung.

C. Results—Lung tissue

The Days 1 and 28 trough mean lung tissue concentrations (23 hours after the end of the previous dose) in each group expressed as ratio to the corresponding mean plasma concentration values at the same time point are presented in Table 72.

TABLE 72

Lung:plasma concentration ratio for each formulation.

| | Day 1 Trough | | Day 28 Trough | |
|---|---|---|---|---|
| Formulation | M | F | M | F |
| XX | 15.9 | 3.7 | 421.6 | 13.8 |
| XXI | 1400 | 818 | 3349 | 1348 |
| XXI x3 d | 897 | 611 | 3783 | 596 |
| XXIII | 15262 | 1500 | 10651 | 3926 |
| XXII | 3543 | 248 | 1201 | 155 |

The lung tissue:plasma ratios for itraconazole were lowest following exposure to Formulation XX and were consistently much higher for all of the crystalline formulations on both Days 1 and 28. These data indicate that the crystalline formulations provide substantially higher lung exposure with less systemic exposure at the doses tested, increasing the exposure at the site of action while minimizing the potential for unwanted effects of systemic exposure.

D. Results—Lung Pathology

In 28-Day study A, Formulation XX-related microscopic findings were present in respiratory tissues at >5 mg/kg/day. Minimal to slight granulomatous inflammation was present at all doses and macrophages and multinucleated giant cells frequently contained intracytoplasmic spicules. At the highest dose, where a 28-day recovery period was included, these only partially recovered. The pathology recorded was considered adverse at all doses due to its dispersed presentation and the fact that it did not fully resolve during the recovery period. The spicular formations noted in the pathology would appear to be itraconazole that, we theorize, are formed when the amorphous material supersaturates the lung lining fluid and interstitial space leading to crystallization of the API after multiple doses. Shorter duration exposure studies with the same formulation showed no such findings.

In 28-Day Study B, Formulations XXI and XXIII were associated with minimal adverse accumulations of foamy macrophages in the lungs only at 40 mg/kg/day with Formulation XXI, the only formulation dosed at that level. There was no clear difference in the incidence and severity of findings between rats dosed with Formulations XXI-XXIII at comparable dose levels. Overall, the No Observed Adverse Effect Level (NOAEL) was approximately 15 mg/kg/day for all three of the crystalline formulations tested.

Pathological findings related to the amorphous compositions in the respiratory tract of rats had a different character from those induced by crystalline formulations, with findings in the latter group more related to a clearance response to accumulated material in the lumen of the airway versus granulomatous inflammation within the mucosa. In addition, amorphous formulation-related findings involved more regions in the respiratory tract and were adverse at a lower dose.

Conclusions

The systemic exposure, i.e., plasma levels of rats to itraconazole was highest following administration of Formulation XX. Systemic exposure was generally less following inhalation administration of Formulations XXI-XXIII, though by Day 28 of dosing the differences were less than after a single dose. Lung exposure, however, was markedly and consistently higher with Formulations XXI-XXIII relative to Formulation XX. When comparing lung and systemic exposure, the ratio for Formulation XX favored lung exposure over systemic. However, the lung:plasma ratio was substantially greater for each of the crystalline formulations, XXI-XXIII. These data indicate that the crystalline formulations provide substantially higher local concentrations of itraconazole, while resulting in the same or less systemic exposure as Formulation XX.

The amorphous nature of the itraconazole in Formulation XX leads to increased solubility and rapid transit through the lung to the systemic circulation as evidenced by the significantly higher systemic exposure on Day 1. Formulation XX dosing also resulted in local toxicity in the form of spicular deposits in the mucosa leading to granulomatous inflammation that was adverse at all doses tested, and as low as 5 mg/kg/day. With the use of crystalline nanoparticles in Formulations XXI-XXIII, the lung retention was substantially greater, leading to higher local exposure than the amorphous formulations with generally the same or less systemic exposure. This change in exposure profile has the advantage of increasing efficacy in the lung with the unwanted effects of systemic itraconazole exposure no worse and possibly minimized further relative to Formulation XX. In addition, Formulations XXI-XXIII showed much lower potential for adverse microscopic pathology findings, despite the substantially higher local exposure.

Summary In-Vitro and In-Vivo Example Summary

The investigation of the effects of the physical form of itraconazole within the dry powder formulations involved an iterative progression through in-vitro dissoluation and permeability studies and in-vivo single and multiple dose pharmacokinetic and toxicity studies. The in-vitro dissolution studies demonstrated that the physical form of itraconazole, as well as the size of crystalline particles within the formulation, play an important role in determining the rate of dissolution as well as the rate at which the delivered material would be expected to pass through the lung and into the systemic circulation. These data demonstrate the ability to control key aspects of both the lung and systemic exposure to allow the modulation of both efficacy as well as potentially the modulation of adverse findings. These in-vitro findings were tested in an in-vivo, single dose inhalation PK study, confirming that, when delivered via inhalation, the powders with crystalline itraconazole nanoparticles resulted in longer lung retention, leading to a higher lung to plasma ratio, as well as reduced peak and total systemic exposure relative to a formulation containing amorphous itraconazole after a single dose. The example summarizing the 28-day inhalation toxicity studies further demonstrated that the different exposure kinetics with amorphous and crystalline itraconazole in the dry powder formulations, in terms of lung and systemic exposure, are retained over multiple days of dosing. In addition, when examining the microscopic pathology effects of the amorphous and crystalline materials after multiple days of dosing, it is clear that differences exist in both the nature and severity of these findings, with the crystalline material showing fewer adverse findings and only at higher lung exposures.

The invention claimed is:

1. A dry powder comprising homogenous respirable dry particles that comprise a) itraconazole in crystalline particulate form, b) a stabilizer, and c) leucine, wherein the crystalline particulate form is in the form of a sub-particle of about 50 nm to about 2,500 nm, wherein the dry powder has a dissolution half-life of 4.13 minutes or greater and less than 16.84 minutes as measured by actuating 10 mg of the dry powder from a size 3 HPMC capsule with an RS01 inhaler at 60 L/min for a total volume of 4 L, collecting the respirable mass onto a glass microfiber filter membrane using a UniDose collection system, and assessing the dissolution profile in a USP V Paddle over Disk apparatus utilizing 500 mL of a pH 7.4 phosphate-buffered saline dissolution media containing 2.0% sodium dodecyl sulfate at 37° C.

2. The dry powder of claim 1, wherein the sub-particle is about 50 nm to about 800 nm (Dv50).

3. The dry powder of claim 1, wherein the itraconazole is present in an amount of about 1% to about 95% by weight.

4. The dry powder of claim 1, wherein the itraconazole is present in an amount of about 40% to about 90% by weight.

5. The dry powder of claim 1, wherein the stabilizer is present in an amount of about 0.05% to about 45% by weight.

6. The dry powder of claim 1, wherein leucine is present in an amount selected from about 1% to about 99% by weight or about 5% to about 50% by weight.

7. The dry powder of claim 1, wherein the dry powder further comprises a monovalent metal cation salt, a divalent metal cation salt, an amino acid, a sugar alcohol, or combinations thereof.

8. The dry powder of claim 1, wherein the dry powder further comprises one or more additional excipients selected from the group consisting of sodium chloride and sodium sulfate.

9. The dry powder of claim 1, wherein the dry powder further comprises magnesium lactate.

10. The dry powder of claim 1, wherein the stabilizer is polysorbate 80 and is present in an amount of 10 wt % or less.

11. The dry powder of claim 1, wherein the stabilizer is oleic acid and is present in an amount of 10 wt % or less.

12. The dry powder of claim 1, wherein the respirable dry particles have a volume median geometric diameter (VMGD) about 10 microns or less, a tap density of between 0.2 g/cc and 1.0 g/cc, an MMAD of between 1 micron and about 5 microns, and a 0.5/4 bar dispersibility ratio (0.5/4 bar) of about 1.5 or less as measured by laser diffraction.

13. The dry powder of claim 1, wherein the dry powder has a FPF of the total dose less than 5 microns of about 25% or more.

14. The dry powder of claim 1, wherein the dry powder is delivered to a patient with a capsule-based passive dry powder inhaler.

15. The dry powder of claim 1, wherein the respirable dry particles have a capsule emitted powder mass of at least 80% when emitted from a passive dry powder inhaler that has a resistance of about 0.036 sqrt(kPa)/liters per minute under the following conditions; an inhalation flow rate of 30 LPM for a period of 3 seconds using a size 3 capsule that contains a total mass of 10 mg, said total mass consisting of the respirable dry particles, and wherein the volume median geometric diameter of the respirable dry particles emitted from the inhaler as measured by laser diffraction is 5 microns or less.

16. A dry powder of claim 1 produced by a process comprising the steps of: spray drying a surfactant-stabilized suspension with optional excipients, wherein dry particles that are compositionally homogeneous are produced.

17. A dry powder comprising homogenous respirable dry particles that comprise a) itraconazole in crystalline particulate form, b) a stabilizer, wherein the stabilizer is polysorbate 80 or oleic acid, and c) one or more excipients, wherein the crystalline particulate form is in the form of a sub-particle of about 50 nm to about 2,500 nm, wherein the dry powder has a dissolution half-life of 4.13 minutes or greater and less than 16.84 minutes as measured by actuating 10 mg of the dry powder from a size 3 HPMC capsule with an RS01 inhaler at 60 L/min for a total volume of 4L, collecting the respirable mass onto a glass microfiber filter membrane using a UniDose collection system, and assessing the dissolution profile via USP V Paddle over Disk (POD) utilizing 500 ml of a pH 7.4 phosphate-buffered saline (PBS) dissolution media containing 2.0% sodium dodecyl sulfate (SDS) at 37° C.

18. A dry powder comprising homogenous respirable dry particles that comprise a) itraconazole in crystalline particulate form, wherein the itraconazole is present in an amount of about 40% to about 90% by weight, b) a stabilizer, and c) leucine, wherein the crystalline particulate form is in the form of a sub-particle of about 50 nm to about 2,500 nm, wherein the dry powder has a dissolution half-life of 4.13 minutes or greater and less than 16.84 minutes as measured by actuating 10 mg of the dry powder from a size 3 HPMC capsule with an RS01 inhaler at 60 L/min for a total volume of 4 L, collecting the respirable mass onto a glass microfiber filter membrane using a UniDose collection system, and assessing the dissolution profile in a USP V-Paddle over Disk apparatus utilizing 500 mL of a pH 7.4 phosphate-buffered saline dissolution media containing 2.0% sodium dodecyl sulfate at 37° C.

19. A method for treating a fungal infection comprising administering to the respiratory tract of a patient in need thereof an effective amount of a dry powder of claim 1.

20. A method for treating a fungal infection in a patient with cystic fibrosis comprising administering to the respiratory tract of the cystic fibrosis patient an effective amount of a dry powder of claim 1.

21. A method for treating a fungal infection in a patient with asthma comprising administering to the respiratory tract of the asthma patient an effective amount of a dry powder of claim 1.

22. A method for treating aspergillosis comprising administering to the respiratory tract of a patient in need thereof an effective amount of a dry powder of claim 1.

23. A method for treating allergic bronchopulmonary aspergillosis (ABPA) comprising administering to the respiratory tract of a patient in need thereof an effective amount of a dry powder of claim 1.

24. A method for treating or reducing the incidence or severity of an acute exacerbation of a respiratory disease comprising administering to the respiratory tract of a patient in need thereof an effective amount of a dry powder of claim 1, wherein the acute exacerbation is a fungal infection.

25. A method for treating a fungal infection in an immunocompromised patient comprising administering to the respiratory tract of the immunocompromised patient an effective amount of a dry powder of claim 1.

\* \* \* \* \*